US011135586B2

(12) United States Patent
Tang et al.

(10) Patent No.: US 11,135,586 B2
(45) Date of Patent: Oct. 5, 2021

(54) FLUORINATED PICKERING EMULSION

(71) Applicants: The Board of Trustees of the Leland Stanford Junior University, Palo Alto, CA (US); The Governors of the University of Alberta, Edmonton (CA)

(72) Inventors: Sindy Tang, Stanford, CA (US); Ming Pan, Stanford, CA (US); Fengjiao Lyu, Stanford, CA (US); Ratmir Derda, Edmonton (CA)

(73) Assignees: The Board of Trustees of the Leland Stanford Junior University, Stanford, CA (US); The Governors of the University of Alberta, Edmonton (CA)

( * ) Notice: Subject to any disclaimer, the term of this patent is extended or adjusted under 35 U.S.C. 154(b) by 0 days.

(21) Appl. No.: 14/922,018

(22) Filed: Oct. 23, 2015

(65) Prior Publication Data

US 2016/0114325 A1 Apr. 28, 2016

Related U.S. Application Data

(60) Provisional application No. 62/191,880, filed on Jul. 13, 2015, provisional application No. 62/068,510, filed on Oct. 24, 2014.

(51) Int. Cl.
*B01L 3/00* (2006.01)
*C07F 7/08* (2006.01)
*C01B 33/18* (2006.01)
*C12Q 1/18* (2006.01)
*G01N 15/14* (2006.01)
*B82Y 40/00* (2011.01)
*B82Y 30/00* (2011.01)
*G01N 15/10* (2006.01)

(52) U.S. Cl.
CPC ... *B01L 3/502761* (2013.01); *B01L 3/502769* (2013.01); *B01L 3/502784* (2013.01); *C01B 33/18* (2013.01); *C07F 7/081* (2013.01); *C12Q 1/18* (2013.01); *G01N 15/1404* (2013.01); *G01N 15/1484* (2013.01); *B01L 2200/0615* (2013.01); *B01L 2200/0647* (2013.01); *B01L 2200/0668* (2013.01); *B01L 2200/16* (2013.01); *B01L 2300/165* (2013.01); *B82Y 30/00* (2013.01); *B82Y 40/00* (2013.01); *C01P 2004/62* (2013.01); *C01P 2004/64* (2013.01); *G01N 2015/1006* (2013.01)

(58) Field of Classification Search
CPC ............ B01L 3/502784; G01N 15/1404
See application file for complete search history.

(56) References Cited

U.S. PATENT DOCUMENTS

2003/0224174 A1 12/2003 White et al.
2008/0134939 A1* 6/2008 Arpac ............... B82Y 30/00
106/287.23
2010/0215894 A1 8/2010 Iverson et al.
2010/0215961 A1 8/2010 Aubry et al.
2013/0064776 A1 3/2013 El Harrak et al.
2013/0210680 A1* 8/2013 Derda ............... C12N 15/1037
506/26
2014/0106165 A1 4/2014 Johnston et al.
2014/0187664 A1 7/2014 Malloggi et al.
2014/0238263 A1* 8/2014 Scheonfisch ............ B05D 1/02
106/2
2014/0287243 A1 9/2014 Weber et al.

FOREIGN PATENT DOCUMENTS

WO WO-2014/059415 A1 4/2014

OTHER PUBLICATIONS

Pazokifard et al. "Fluoroalkylsilane treatment of TiO2 nanoparticles in difference pH values: Characterization and mechanism" Advanced Powder Technology 23 (2012) 428-436.*
Wang et al. "One-step coating of fluoro-containing silica nanoparticles for universal generation of surface superhydrophobicity" Chem. Commun., 2008, 877-879.*
Zhang, Hong, Sijia Wang, and Stephen G. Weber. "Nanocomposite Teflon AF 2400 films as tunable platforms for selective transport." Analytical chemistry 84.22 (2012): 9920-9927. (Year: 2012).*
Brassard, J-D. et al. (2001) "Synthesis of Monodisperse Fluorinated Silica Nanoparticles and Their Superhydrophoic Thin Films," ACS Appl. Mater. Interfaces 3(9):3583-3588.
Lee, K.J. et al. (2011) "Recent advances with anisotropic particles," Current Opinion in Colloid & Interface Science 16:195-202.
Ogawa, S. et al. (2014) "Liquid Marbles Supported by Monodisperse Poly(methylsilsesquioxane) Particles," Langmuir 30:9071-9075.
Pan, M. et al. (2014) "Fluorinated pickering emulsions impede interfacial transport and form rigid interface for the growth of anchorage-dependent cells," ACS Appl. Mater. Interfaces 6:21446-21453.

(Continued)

Primary Examiner — Robert J Yamasaki
(74) Attorney, Agent, or Firm — Foley & Lardner LLP

(57) ABSTRACT

Described here is a composition comprising amphiphilic silica nanoparticles, wherein the silica nanoparticles are partially fluorinated. Also described here is a method for droplet-based assay, comprising dispersing at least one aqueous droplet in a continuous fluorous phase in a microfluidic channel, wherein at least one amphiphilic silica nanoparticle is absorbed to the interface of the continuous fluorous phase and the aqueous droplet, and wherein the silica nanoparticle is partially fluorinated. Further described here is a method for droplet-based assay, comprising dispersing at least one aqueous phase droplet in a continuous fluorous phase in a microfluidic channel, wherein the continuous fluorous phase comprises at least one partially fluorinated amphiphilic particle adsorbed to an interface of the continuous fluorous phase and the aqueous phase droplet, and wherein the aqueous phase droplet comprises at least one hydrophilic polymer adsorbed to the amphiphilic particle at the interface.

14 Claims, 31 Drawing Sheets

(56) References Cited

OTHER PUBLICATIONS

Pan, M. et al. (2014) "The Use of Pickering Emulsion for Mitigating Dye Leakage in Droplet Microfluidics," 18th International Conference on Miniaturized Systems for Chemistry and Life Sciences, Oct. 26-30, 2014, San Antonio, TX:76-78.

Pan, M. et al. (2015) "Fluorinated pickering emulsions with nonadsorbing interfaces for droplet-based enzymatic assays," Anal. Chem. 87:7938-7943.

Pustovit, V.N. et al. (2012) "Fluorescence quenching near small metal nanoparticles," The Journal of Chemical Physics 136:20471.

Rosenfeld, L. et al. (2014) "Review and analysis of performance metrics of droplet microfluidics systems," Microfluid Nanofluid 16:921-939.

Wang, H. et al. (2008) "One-step coating of fluoro-containing silica nanoparticles for universal generation of surface superhydrophobicity," Chem. Commun. 2008:877-879.

Wang, J-T. et al. (2011) "Fabrication of Advanced Particles and Particle-Based Materials Assisted by Droplet-Based Microfluidics," Small 7(13):1728-1754.

Yildirim, A. et al. (2011) "One-Pot Preparation of Fluorinated Mesoporous Silica Nanoparticles for Liquid Marble Formation and Superhydrophobic Surfaces," ACS Appl. Mater. Interfaces 3:1804-1808.

Zhao, Y. et al. (2013) "Bioinspired Multifunctional Janus Particles for Droplet Manipulation," J. Am. Chem. Soc. 135:54-57.

Zhu, Y. et al. (2014) "Synthesis of Latex Particles with a Complex Structure as an Emulsifier of Pickering High Internal Phase Emulsions," Ind. Eng. Chem. Res. 53:4642-4649.

Extended European Search Report for European Patent Application No. 15852737.4, dated Jun. 18, 2018.

Communication Pursuant to Article 94(3) EPC issued in EP Application No. 15852737.4 dated Sep. 18, 2018, 2 pages.

Extended European Search Report issued in EP Application No. 19165777.4 dated May 15, 2019, 9 pages.

Communication Pursuant to Article 94(3) EPC on EP 19165777.4 dated Dec. 17, 2020 (6 pages).

* cited by examiner

FLUORINATED PICKERING EMULSION

CROSS-REFERENCE TO RELATED APPLICATIONS

This application claims the benefit of U.S. Provisional Patent Application No. 62/068,510 filed Oct. 24, 2014 and U.S. Provisional Patent Application No. 62/191,880 filed Jul. 13, 2015, the contents of which are incorporated herein by reference in their entireties.

BACKGROUND

Droplet microfluidics, in which droplets act as individual reactors, has allowed drastic improvements in the throughput of biochemical processes including digital PCR, directed evolution of enzymes and screening of antibiotics. The key assumption in droplet-based assays is that reagents remain isolated in individual droplets, and cannot diffuse across the interface between a drop and the continuous phase. The continuous phase is typically a fluorinated oil due to its gas permeability, chemical inertness, and low toxicity to cells. As the fluorous phase is immiscible with both the aqueous and organic phases, it is generally assumed that the transport of molecules among drops is insignificant. It has been observed, however, that small and hydrophobic fluorescent molecules (e.g., resorufin) diffused and leaked out of aqueous drops through a continuous phase of fluorinated solvents (e.g., 2-(Trifluoromethyl)-3-ethoxydodecafluorohexane ("HFE-7500") or 1,1,2,2,3,3,4,4,4-Nonafluoro-N,N-bis(1, 1,2,2,3,3,4,4,4-nonafluorobutyl)butan-1-amine, 1, 1,2,2,3,3, 4,4,4-nonafluoro-N-(1,1,2,2,3,3,4,4,4-nonafluorobutyl)-N-(trifluoromethyl)butan-1-amine ("FC-40") containing nonionic fluorosurfactant made of poly(ethylene glycol)-perfluorinated polyether ("PEG-PFPE") amphiphilic block copolymer (also referred to as "EA-surfactant" from RainDance Technologies). The leakage process occurred over tens of seconds to a few hours. Such leakage has detrimental effects on the accuracy of the assay. The transport of molecules in reverse micelles formed by surfactant molecules present in the continuous phase has been confirmed to play a significant role. The use of surfactant concentrations below the critical micelle concentration would mitigate such leakage. Drops would become increasingly prone to coalescence, however, if low concentrations of surfactants are used. Additives such as bovine serum albumin and sugars have been added to the aqueous phase to increase the retention of molecules in drops. Hydrophilic groups (e.g., sulfonates) have also been incorporated into small molecules (e.g., coumarin) to eliminate its leakage out of the drops. Introduction of polar hydrophilic groups inevitably decreases the hydrophobicity and cell-permeability of the substrates. For cell viability substrates that hinge on cell-permeability, such change is counterproductive as it can inactivate the substrates.

Another key limitation of surfactant-based droplet systems is its incompatibility with the culture of anchorage-dependent cells. These cells divide when they are attached to a rigid substrate that can resist sustained contractive forces by cells. Interfaces laded with surfactants are not sufficiently rigid to support the growth of these cells. To provide anchorage support for cells, drops were previously pinned to a solid surface to allow cells to attach to a rigid support. Alternatively, surfactants that were covalently linked to gold nanoparticles modified with integrin-binding cyclic RGD peptide were synthesized. The synthesis of such surfactants was complex. In addition, it was unclear whether the rigidity of the water-oil interface was sufficient for cell proliferation. Cells actively sense the stiffness of the substrate and can undergo cell death if the substrate is too soft. Despite some indication of adhesion of cells to nanoparticle-stabilized interfaces, the proliferation of anchorage-dependent cells at water-oil interfaces has not been demonstrated.

Thus, there is a need for emulsifiers that can: 1) stabilize aqueous or organic drops, 2) minimize leakage without the need to modify the content and chemistry of the aqueous or organic phase, 3) provide a sufficiently rigid interface for the attachment and growth of anchorage-dependent cells, and 4) provide a non-adsorbing and non-denaturing interface for droplet-based protein assays such as enzymatic assays.

SUMMARY

One aspect of some embodiments of the invention described herein relates to a composition comprising one or more amphiphilic particles (e.g., nanoparticles and/or microparticles), wherein the amphiphilic particles are partially fluorinated. The partially fluorinated amphiphilic particles include both homogeneous particles and Janus particles where the surface has two or more distinct physical and/or chemical properties.

In some embodiments, the amphiphilic particles are ceramic nanoparticles or microparticles, metal nanoparticles or microparticles, polymeric nanoparticles or microparticles, or semiconductor nanoparticles or microparticles, or a combination thereof. In some embodiments, the amphiphilic particles are silica nanoparticles or microparticles. In some embodiments, other particles that have functionalizable surfaces and can be rendered amphiphilic are also compatible with embodiments of the invention described herein, such as particles made from noble metals, semiconductors or organic polymers.

In some embodiments, at least 50% (e.g., by number or weight), at least 70%, at least 80%, at least 90%, or at least 95% of the nanoparticles and/or microparticles of the composition are amphiphilic particles. In some embodiments, at least 50% (e.g., by number or weight), at least 70%, at least 80%, at least 90%, or at least 95% of the nanoparticles and/or microparticles of the composition are amphiphilic silica nanoparticles.

The amphiphilic nature of the particles described herein (e.g., silica nanoparticles) is evident from the three phase contact angle $\theta$ when they are placed at an interface of a fluorous oil phase and a water phase (see FIG. 17). In some embodiments, the amphiphilic particles have a contact angle $\theta$ of about 90° to 150° at an interface of a fluorous oil phase and a water phase. In some embodiments, the amphiphilic particles have a contact angle $\theta$ of about 90° to 135° at an interface of a fluorous oil phase and a water phase. In some embodiments, the amphiphilic particles have a contact angle $\theta$ of about 90° to 120° at an interface of a fluorous oil phase and a water phase. In some embodiments, the amphiphilic particles have a contact angle $\theta$ of about 100° to 110° at an interface of a fluorous oil phase and a water phase.

In some embodiments, at least 50%, at least 70%, at least 80%, at least 90%, or at least 95% of the amphiphilic particles of the composition, when placed at an interface of a fluorous oil phase and a water phase, have a contact angle $\theta$ of about 90° to 150°. In some embodiments, at least 50%, at least 70%, at least 80%, at least 90%, or at least 95% of the amphiphilic particles of the composition, when placed at an interface of a fluorous oil phase and a water phase, have a contact angle $\theta$ of about 90° to 135°. In some embodiments, at least 50%, at least 70%, at least 80%, at least 90%, or at least 95% of the amphiphilic particles of the composition, when placed at an interface of a fluorous oil phase and a water phase, have a contact angle θ of about 90° to 120°. In some embodiments, at least 50%, at least 70%, at least 80%, at least 90%, or at least 95% of the amphiphilic particles of the composition, when placed at an interface of a fluorous oil phase and a water phase, have a contact angle θ of about 100° to 110°.

In some embodiments, the amphiphilic particle has at least one lateral dimension of 0.001-1000 microns. In some embodiments, the amphiphilic particle has at least one lateral dimension of 0.01-100 microns. In some embodiments, the amphiphilic particle has at least one lateral dimension of 0.1-10 microns. In some embodiments, the amphiphilic particle has at least one lateral dimension of 1-5000 nm. In some embodiments, the amphiphilic particle has at least one lateral dimension of 10-950 nm. In some embodiments, the amphiphilic particle has at least one lateral dimension of 20-200 nm. In some embodiments, the amphiphilic particle has at least one lateral dimension of 200-800 nm. In some embodiments, the amphiphilic particle has a size that will not cause clogging in microfluidic devices and/or sedimentations (for prolonged time) in syringes, such as 50-200 nm. In some embodiments, same mass of particles gives higher concentration in terms of particle number per volume. Microparticles larger than 5 microns can also be used.

In some embodiments, the amphiphilic particle comprises fluorinated groups covalently bonded on the surface of the particle. In some embodiments, the amphiphilic particle comprises fluorinated hydrocarbon groups bonded on the surface of the particle, such as fluorinated alkyl groups bonded on the surface of the particle. Examples of fluorinated hydrocarbon groups include C1-C20, C2-C20, C5-C20, C10-C20, C1-C15, C2-C15, C5-C15, C10-C15, C1-C10, C2-C10, C5-C10, and C5-C8 hydrocarbon groups, substituted with 1 or more, 2 or more, 3 or more, 4 or more, 5 or more, 6 or more, 7 or more, 8 or more, 9 or more, 10 or more, 11 or more, 12 or more, or 13 or more fluorine atoms per hydrocarbon group. Other types of halogenated hydrocarbon groups are also contemplated. In some embodiments, the amphiphilic particle is partially derivatized with at least one partially fluorinated or perfluorinated alkyl-silane. In some embodiments, the amphiphilic particle is partially derivatized with at least one partially fluorinated or perfluorinated alkyl-silane comprising a linear carbon chain. In some embodiments, the amphiphilic particle is partially derivatized with 1H, 1H, 2H, 2H-perfluorooctyltriethoxysilane (FAS) on the surface.

In some embodiments, the amphiphilic particle comprises hydrophilic groups, in addition to or in place of fluorinated groups, covalently bonded on the surface of the particle. In some embodiments, the amphiphilic particle comprises amine groups covalently bonded on the surface of the particle. In some embodiments, the amphiphilic particle comprises other chemical groups covalently bonded on the surface of the particle, including but not restricted to —OH, —COOH, —NH$_2$, —CxHy, —SO$_3$H, fluorophores such as fluorescein, rhodamine, macromolecules such as biotin, streptavidin, and polyethylene glycol (PEG).

In some embodiments, the amphiphilic particles on average have at least 30% of their outer surface areas fluorinated/derivatized. In some embodiments, the amphiphilic particles on average have at least 40% of their outer surface areas fluorinated/derivatized. In some embodiments, the amphiphilic particles on average have at least 50% of their outer surface areas fluorinated/derivatized. In some embodiments, the amphiphilic particles on average have at least 60% of their outer surface areas fluorinated/derivatized. In some embodiments, the amphiphilic particles on average have at least 70% of their outer surface areas fluorinated/derivatized. In some embodiments, the amphiphilic particles on average have at least 80% of their outer surface areas fluorinated/derivatized. In some embodiments, the amphiphilic particles on average have at least 90% of their outer surface areas fluorinated/derivatized. In some embodiments, the amphiphilic particles have up to 100% of their outer surface areas fluorinated/derivatized. The partially fluorinated amphiphilic particles include both homogeneous particles and Janus particles where the surface has two or more distinct physical and chemical properties.

In some embodiments, the composition comprises a mixture of amphiphilic particles having different sizes and chemistry.

In some embodiments, the amphiphilic particles have high temperature stability, and hence suitable for applications that requires heating, such as PCR. In some embodiments, the amphiphilic particles are substantially stable after heating at 95° C. for at least 20 minutes, or at least 30 minutes, or at least 60 minutes. In some embodiments, the amphiphilic particles are substantially stable after heating at 150° C. for at least 20 minutes, or at least 30 minutes, or at least 60 minutes. In some embodiments, the amphiphilic particles are substantially stable after heating at 200° C. for at least 20 minutes, or at least 30 minutes, or at least 60 minutes.

In some embodiments, the amphiphilic particles have a spherical shape. In some embodiments, the amphiphilic particles have an elliptical shape. In some embodiments, the amphiphilic particles have a rod-like shape. In some embodiments, the amphiphilic particles have a plate-like shape.

In some embodiments, the composition comprises a fluorous phase comprising at least one fluorinated solvent, wherein the amphiphilic particles (e.g., silica nanoparticles) are dispersed in the fluorinated solvent. In some embodiments, the composition consists essentially of or consists of the fluorous phase comprising the fluorinated solvent(s) and the amphiphilic particles.

In some embodiments, the fluorous phase comprises at least one fluorocarbon represented by $C_xF_yH_zX_m$ where X can be any element (including but not restricted to N and O), and x, y, z, and m are positive integers. In some embodiments, the fluorous phase comprises HFE-7500 ($C_9H_5OF_{15}$), HFE-7600 ($C_8H_6OF_{12}$), FC-40 ($C_{21}F_{48}N_2$), perfluorohexane ($C_6F_{14}$), and/or perfluoromethyldecalin (PFMD or $C_{11}F_{20}$) as the fluorinated solvent. The fluorinated solvent is not particularly limited but can include a diverse range of fluorinated compounds having distinct physical properties. In some embodiments, the fluorinated solvent comprises a polar, partially fluorinated solvent with low viscosity, such as hydrofluoroethers like HFE-7500 and HFE-7600. In some embodiments, the fluorinated solvent comprises a polar, perfluorinated solvent with high viscosity, such as FC-40. In some embodiment, the fluorinated solvent comprises a non-polar, perfluorinated solvent with low viscosity, such as $C_6F_{14}$. In some embodiments, the fluorinated solvent comprises a non-polar perfluorinated solvent with high viscosity, such as perfluoromethyldecalin ("PFMD").

In some embodiments, the composition comprises a fluorocarbon phase comprising at least one fluorinated solvent and a second phase comprising a fluid immiscible with the fluorinated solvent, wherein the amphiphilic particles (e.g., silica nanoparticles) are absorbed to the interface of the fluorocarbon phase and the second phase.

In some embodiments, the composition comprising an emulsion comprising (a) a continuous phase, and (b) at least one dispersed phase droplet dispersed in the continuous phase. In some embodiments, the composition comprising an emulsion comprising (a) a continuous fluorophilic phase, and (b) at least one dispersed aqueous or lipophilic phase dispersed in the continuous fluorophilic phase.

In some embodiments, the dispersed phase has an average diameter greater than or equal to about 50 nm and less than or equal to about 1000 microns. In some embodiments, the dispersed phase has an average diameter of no more than about 1000 microns. In some embodiments, the dispersed phase has an average diameter greater than or equal to about 50 nm. In some embodiments, the dispersed phase comprises an aqueous solution comprising a biological molecule. In some embodiments, the biological molecule comprises a nucleic acid. In some embodiments, the biological molecule comprises an oligonucleotide. In some embodiments, the dispersed phase does not coalesce for at least 30 minutes at 25° C. and 1 atm. In some embodiments, the dispersed phase comprises buffers, salts, nutrients, therapeutic agents, drugs, hormones, antibodies, analgesics, anticoagulants, anti-inflammatory compounds, antimicrobial compositions, cytokines, growth factors, interferons, lipids, oligonucleotides polymers, polysaccharides, polypeptides, protease inhibitors, cells, nucleic acids, RNA, DNA, vasoconstrictors or vasodilators, vitamins, minerals, or stabilizers. In some embodiments, a chemical and/or biological reaction is performed in the dispersed phase.

In some embodiments, the composition comprises a fluorocarbon phase comprising at least one fluorinated solvent and an aqueous or organic phase, wherein the amphiphilic particles (e.g., silica nanoparticles) are absorbed to the interface of the fluorocarbon phase and the aqueous or organic phase.

In some embodiments, the aqueous phase has an average diameter greater than or equal to about 50 nm and less than or equal to about 1000 microns. In some embodiments, the aqueous phase has an average diameter of no more than about 1000 microns. In some embodiments, the aqueous phase has an average diameter greater than or equal to about 50 nm. In some embodiments, the aqueous phase comprises an aqueous solution comprising a biological molecule. In some embodiments, the biological molecule comprises a nucleic acid. In some embodiments, the biological molecule comprises an oligonucleotide. In some embodiments, the aqueous phase does not coalesce for at least 30 minutes at 25° C. and 1 atm. In some embodiments, the aqueous phase comprises buffers, salts, nutrients, therapeutic agents, drugs, hormones, antibodies, analgesics, anticoagulants, anti-inflammatory compounds, antimicrobial compositions, cytokines, growth factors, interferons, lipids, oligonucleotides polymers, polysaccharides, polypeptides, protease inhibitors, cells, nucleic acids, RNA, DNA, vasoconstrictors or vasodilators, vitamins, minerals, or stabilizers. In some embodiments, a chemical and/or biological reaction is performed in the aqueous phase.

In some embodiments, the composition comprising an emulsion comprising (a) a continuous fluorocarbon phase, and (b) at least one aqueous or organic phase droplet dispersed in the continuous fluorocarbon phase.

In some embodiments, the composition comprising an emulsion comprising (a) a continuous aqueous phase, and (b) at least one fluorocarbon phase droplet dispersed in the continuous aqueous phase.

In some embodiments, the composition comprises a fluorocarbon phase comprising at least one fluorinated solvent and a hydrocarbon phase, wherein the amphiphilic particles (e.g., silica nanoparticles) are absorbed to the interface of the fluorocarbon phase and the hydrocarbon phase.

In some embodiments, the composition comprising an emulsion comprising (a) a continuous fluorocarbon phase, and (b) at least one hydrocarbon phase droplet dispersed in the continuous fluorocarbon phase.

In some embodiments, the composition comprising an emulsion comprising (a) a continuous hydrocarbon phase, and (b) at least one fluorocarbon phase droplet dispersed in the continuous hydrocarbon phase.

In some embodiments, the composition comprises a fluorocarbon phase comprising at least one fluorinated solvent and a gas phase, wherein the amphiphilic particles (e.g., silica nanoparticles) are absorbed to the interface of the fluorocarbon phase and the gas phase.

In some embodiments, the composition comprising an emulsion comprising (a) a continuous fluorocarbon phase, and (b) at least one gas phase bubble dispersed in the continuous fluorocarbon phase.

In some embodiments, the composition comprises a gas phase encapsulated by a layer of the amphiphilic particles (e.g., silica nanoparticles). In some embodiments, the composition is used as an ultrasound contrast agent.

In some embodiments, the composition comprises a liquid phase encapsulated by a layer of the amphiphilic particles (e.g., silica nanoparticles). In some embodiments, the composition comprises a liquid marble. In some embodiments, the composition is used for gas sensing and gas storage.

In some embodiments, the composition comprises a solid phase encapsulated by a layer of the amphiphilic particles (e.g., silica nanoparticles). In some embodiments, the composition is used for gas sensing and gas storage.

In some embodiments, the dispersed phase (e.g., aqueous or organic phase) comprises at least one reporting molecule capable of generating a detectable signal. In some embodiments, the dispersed phase comprises at least one fluorescent molecule. In some embodiments, the dispersed phase comprises green fluorescent protein (GFP) and/or resorufin.

In some embodiments, the dispersed phase (e.g., aqueous or organic phase) comprises at least one cell. In some embodiments, the cell is anchored to the amphiphilic particle (e.g., silica nanoparticle) at the interface of the fluorous phase and the aqueous or organic phase. In some embodiments, the cell is capable of spreading and proliferating. In some embodiments, the cell is an eukaryotic cell which does not grow in suspensions or in surfactant-stabilized emulsions, but is capable of growing in the emulsion described herein comprising amphiphilic particles. In some embodiments, the invention relates to an emulsion for growing anchorage dependent cells. In some embodiments, the invention relates to an assay that detect differences in growth of anchorage dependent cells (e.g., cytotoxicity, drug toxicity, proliferation, differentiation, etc.).

In some embodiments, the amphiphilic particles described herein are biocompatible with bacteria, mammalian cells, protozoans, and phage. In some embodiments, the amphiphilic particles described herein are biocompatible with adhesion and growth of different types of anchorage dependent cells (e.g., fibroblast, cancer cells, etc.).

In some embodiments, the emulsion drops do not break up or coalesce upon washing off the excess nanoparticles in the continuous phase (e.g., replacing the continuous phase with neat fluorinated oil), incubation at room temperature for at least 24 hours and reinjection through a narrow constriction.

In some embodiments, the emulsion drops are stable at high temperature under PCR experimental condition (e.g., up to 95° C.).

In some embodiments, the amphiphilic particles and combinations thereof described herein provide sufficient stabilization against coalescence of droplets, without interfering with processes that can be carried out inside the droplets.

In some embodiments, the emulsion effectively prevents leakage of fluorophores and fluorogenic substrates (e.g., resorufin, fluorescein, resazurin, 4-methylumbelliferone, etc.) from the dispersed phase to the continuous phase. In some embodiments, after 1 day of incubation at 20° C., less than 30% of the resorufin would leak from the dispersed phase to the continuous phase. In some embodiments, after 1 day of incubation at 20° C., less than 20% of the resorufin would leak from the dispersed phase to the continuous phase. In some embodiments, after 1 day of incubation at 20° C., less than 10% of the resorufin would leak from the dispersed phase to the continuous phase. In some embodiments, after 1 day of incubation at 1° C., less than 5% of the resorufin would leak from the dispersed phase to the continuous phase. In some embodiments, after 1 day of incubation at 20° C., less than 1% of the resorufin would leak from the dispersed phase to the continuous phase.

In some embodiments, the emulsion described herein is made by microfluidics. In some embodiments, the emulsion described herein is made by a homogenizer. In some embodiments, the emulsion described herein is made by shaking.

Another aspect of some embodiments of the invention described herein relates to a droplet microfluidic device comprising the amphiphilic particle (e.g., silica nanoparticle) containing composition. In some embodiment, the droplet microfluidic device comprises a microfluidic channel, wherein amphiphilic particle (e.g., silica nanoparticle) containing composition is present in the microfluidic channel.

Another aspect of some embodiments of the invention described herein relates to a stable emulsion comprising (a) a continuous fluorous phase, (b) at least one aqueous or organic phase droplet dispersed in the continuous fluorous phase, and (c) at least one amphiphilic particle (e.g., silica nanoparticle) absorbed to the interface of the fluorous phase and the aqueous or organic phase, wherein the silica nanoparticle is partially fluorinated. In some embodiments, the emulsion drops do not break up or coalesce upon washing off the excess nanoparticles in the continuous phase (e.g., replacing the continuous phase with neat fluorinated oil), incubation at room temperature for at least 24 hours and reinjection through a narrow constriction. In some embodiments, the emulsion drops are stable at high temperature under PCR experimental condition.

Another aspect of some embodiments of the invention described herein relates to a method for droplet-based assay, comprising dispersing at least one aqueous or organic phase droplet in a continuous fluorous phase in a microfluidic channel, wherein at least one amphiphilic particle (e.g., silica nanoparticle) is absorbed to the interface of the continuous fluorous phase and the aqueous or organic phase droplet, and wherein the silica nanoparticle is partially fluorinated. In some embodiments, the amphiphilic particles are first dispersed in the fluorous phase before absorbing to the interface of the fluorous phase and the aqueous or organic phase. In some embodiments, the amphiphilic particles are first dispersed in the aqueous or organic phase before absorbing to the interface of the fluorous phase and the aqueous or organic phase.

Another aspect of some embodiments of the invention described herein relates to a method for droplet-based assay, comprising emulsifying an aqueous or organic phase droplet using amphiphilic particles (e.g., silica nanoparticles), wherein the amphiphilic particles are absorbed to the interface of the aqueous or organic phase droplet and a continuous fluorous phase.

Another aspect of some embodiments of the invention described herein relates to a method for making an amphiphilic particle (e.g., silica nanoparticle) composition, comprising reacting the particles with at least one fluorinating agent to obtain a composition comprising amphiphilic particles, wherein at least 50%, at least 70%, at least 80%, at least 90%, or at least 95% of the particles in the composition obtained have a contact angle θ of about 90° to 150°, about 90° to 135°, about 90° to 120, or about 100° to 110° when placed at an interface of a fluorous oil phase and a water phase.

In order to maintain protein activity such as enzymatic activity and assay accuracy, an approach is developed that prevents non-specific adsorption and subsequent degradation of proteins, and the leakage of fluorophores used in fluorogenic substrates. The Pickering emulsion system described above can be modified by introducing hydrophilic polymers such as polyethylene glycol (PEG) into the dispersed phase, while F—SiO2 NPs are pre-dispersed in the continuous phase. As drops are generated, the F—SiO2 NPs adsorb to the water-oil interface and the hydrophilic polymers adsorb onto the surface of the F—SiO2 NPs from within the drops. For example, partially fluorinated silica nanoparticles and microparticles adsorbed with PEG are referred to as "$PEG_{ads}$-F—$SiO_2$NPs." Alternatively, particles covalently grafted with hydrophilic polymers can be dispersed into the continuous phase. For example, partially fluorinated silica nanoparticles and microparticles covalently grafted with PEG are referred to as "$PEG_{covalent}$-F—SiO2 NPs."

Accordingly, one aspect of some embodiments of the invention described herein relates to a method for droplet-based assay, comprising dispersing at least one aqueous phase droplet in a continuous fluorous phase in a microfluidic channel, wherein the continuous fluorous phase comprises at least one partially fluorinated amphiphilic particle (e.g., nanoparticle or microparticle) adsorbed to an interface of the continuous fluorous phase and the aqueous phase droplet, and wherein the aqueous phase droplet comprises at least one hydrophilic polymer adsorbed to the amphiphilic particle at the interface (e.g., $PEG_{ads}$-F—$SiO_2$NPs). The amphiphilic particle encompasses both homogeneous particles and Janus particles where the surface has two or more distinct physical and chemical properties.

Alternatively, another aspect of some embodiments of the invention described herein relates to a method for droplet-based assay, comprising dispersing at least one aqueous phase droplet in a continuous fluorous phase in a microfluidic channel, wherein the continuous fluorous phase comprises at least one partially fluorinated amphiphilic particle (e.g., nanoparticle or microparticle) adsorbed to an interface of the continuous fluorous phase and the aqueous phase droplet, and wherein the amphiphilic particle is covalently grafted with at least one hydrophilic polymer (e.g., $PEG_{covalent}$-F—SiO2 NPs). The amphiphilic particle encompasses both homogeneous particles and Janus particles where the surface has two or more distinct physical and chemical properties.

In some embodiments, the hydrophilic polymer is polyethylene glycol (PEG). Other embodiments of the hydrophilic polymers include polyelectrolytes and non-ionic polymers such as homopolymers (e.g., polyethers, Polyacrylamide (PAM), Polyethylenimine (PEI), Poly (acrylic acid), Polymethacrylate and Other Acrylic Polymers, Poly(vinyl alcohol) (PVA), Poly(vinylpyrrolidone) (PVP)), and block co-polymers.

In some embodiments, the hydrophilic polymer is covalently grafted onto the amphiphilic particle. In some embodiments, the hydrophilic polymer is not covalently linked to the amphiphilic particle.

In some embodiments, the amphiphilic particle is a silica particle. In some embodiments, besides silica particle, other particles that have functionalizable surfaces and can be rendered amphiphilic are also compatible with embodiments of the invention described herein, such as particles made from noble metals, semiconductors or organic polymers. Silica is one preferred choice because it has versatile surface functionality and is economical, biocompatible and optically inactive.

In some embodiments, the amphiphilic particle has at least one lateral dimension of 1-5000 nm. In some embodiments, the amphiphilic particle has at least one lateral dimension of 10-950 nm. In some embodiments, the amphiphilic particle has at least one lateral dimension of 20-200 nm. In some embodiments, the amphiphilic particle has at least one lateral dimension of 200-800 nm. In some embodiments, the amphiphilic particle has a size that will not cause clogging in microfluidic devices and/or sedimentations (for prolonged time) in syringes, such as 50-200 nm. In some embodiments, same mass of particles gives higher concentration in terms of particle number per volume. Microparticles larger than 5 microns can also be used.

In some embodiments, the amphiphilic particle comprises fluorinated groups covalently bonded on the surface of the particle. In some embodiments, the amphiphilic particle comprises fluorinated hydrocarbon groups bonded on the surface of the particle, such as fluorinated alkyl groups bonded on the surface of the particle. Examples of fluorinated hydrocarbon groups include C1-C20, C2-C20, C5-C20, C10-C20, C1-C15, C2-C15, C5-C15, C10-C15, C1-C10, C2-C10, C5-C10, and C5-C8 hydrocarbon groups, substituted with 1 or more, 2 or more, 3 or more, 4 or more, 5 or more, 6 or more, 7 or more, 8 or more, 9 or more, 10 or more, 11 or more, 12 or more, or 13 or more fluorine atoms per hydrocarbon group. Other types of halogenated hydrocarbon groups are also contemplated. In some embodiments, the amphiphilic particle is partially derivatized with at least one partially fluorinated or perfluorinated alkyl-silane. In some embodiments, the amphiphilic particle is partially derivatized with at least one partially fluorinated or perfluorinated alkyl-silane comprising a linear carbon chain. In some embodiments, the amphiphilic particle is partially derivatized with 1H, 1H, 2H, 2H-perfluorooctyltriethoxysilane (FAS) on the surface.

In some embodiments, the amphiphilic particles have high temperature stability, and hence suitable for applications that requires heating, such as PCR. In some embodiments, the amphiphilic particles are substantially stable after heating at 95° C. for at least 20 minutes, or at least 30 minutes, or at least 60 minutes. In some embodiments, the amphiphilic particles are substantially stable after heating at 150° C. for at least 20 minutes, or at least 30 minutes, or at least 60 minutes. In some embodiments, the amphiphilic particles are substantially stable after heating at 200° C. for at least 20 minutes, or at least 30 minutes, or at least 60 minutes.

The amphiphilic nature of the silica particles described herein is evident from the three phase contact angle θ when the silica particles are placed at an interface of a fluorous oil phase and a water phase. In some embodiment, the silica particles have a contact angle θ of about 90° to 150° at an interface of a fluorous oil phase and a water phase. In some embodiment, the silica particles have a contact angle θ of about 90° to 135° at an interface of a fluorous oil phase and a water phase. In some embodiment, the silica particles have a contact angle θ of about 90° to 120° at an interface of a fluorous oil phase and a water phase. In some embodiment, the silica particles have a contact angle θ of about 100° to 110° at an interface of a fluorous oil phase and a water phase.

In some embodiments, at least 50%, at least 70%, at least 80%, at least 90%, or at least 95% of the silica particles in the fluorous phase, when placed at an interface of a fluorous oil phase and a water phase, have a contact angle θ of about 90° to 150°. In some embodiments, at least 50%, at least 70%, at least 80%, at least 90%, or at least 95% of the silica particles in the fluorous phase, when placed at an interface of a fluorous oil phase and a water phase, have a contact angle θ of about 90° to 135°. In some embodiments, at least 50%, at least 70%, at least 80%, at least 90%, or at least 95% of the silica particles in the fluorous phase, when placed at an interface of a fluorous oil phase and a water phase, have a contact angle θ of about 90° to 120°. In some embodiments, at least 50%, at least 70%, at least 80%, at least 90%, or at least 95% of the silica particles in the fluorous phase, when placed at an interface of a fluorous oil phase and a water phase, have a contact angle θ of about 100° to 110°.

In some embodiments, the fluorous phase comprises at least one fluorinated solvent. In some embodiments, the fluorous phase comprises HFE-7500, HFE-7600, FC-40, perfluorohexane ($C_6F_{14}$), and/or perfluoromethyldecalin (PFMD) as the fluorinated solvent. The fluorinated solvent is not particularly limited but can include a diverse range of fluorinated compounds having distinct physical properties. In some embodiments, the fluorinated solvent comprises a polar, partially fluorinated solvent with low viscosity, such as HFE-7500 and 7600. In some embodiments, the fluorinated solvent comprises a polar, perfluorinated solvent with high viscosity, such as FC-40. In some embodiments, the fluorinated solvent comprises a non-polar, perfluorinated solvent with low viscosity, such as $C_6F_{14}$. In some embodiments, the fluorinated solvent comprises a non-polar perfluorinated solvent with high viscosity, such as PFMD.

In some embodiments, the aqueous phase comprises at least one reporting molecule capable of generating a detectable signal. In some embodiments, the aqueous phase comprises at least one fluorescent molecule. In some embodiments, the aqueous phase comprises at least one protein (e.g., enzymes, antibodies, hormones, structural proteins, and membrane proteins).

In some embodiments, the aqueous phase comprises 0.01 mg/mL or more, or 0.02 mg/mL or more, or 0.05 mg/mL or more, or 0.1 mg/mL or more, or 0.2 mg/mL or more, or 0.5 mg/mL or more, or 1 mg/mL or more, or 2 mg/mL or more, or 5 mg/mL or more, or 10 mg/mL or more of a hydrophilic polymer (e.g., PEG). In some embodiments, the aqueous phase comprises an effective amount of a hydrophilic polymer (e.g., PEG) for preventing non-specific adsorption of proteins and enzymes to the droplet interface and to maintain their activities.

In some embodiments, the hydrophilic polymer-adsorbed amphiphilic particles are non-adsorbing and non-denaturing to proteins (e.g., enzymes, antibodies, hormones, structural proteins, and membrane proteins). In some embodiments, the hydrophilic polymer-grafted amphiphilic particles are non-adsorbing and non-denaturing to proteins (e.g., enzymes, antibodies, hormones, structural proteins, and membrane proteins).

Another aspect of some embodiments of the invention described herein relates to a Pickering emulsion comprising a continuous fluorous phase and at least one aqueous phase droplet dispersed therein, wherein the continuous fluorous phase comprises at least one partially fluorinated amphiphilic particle (e.g., nanoparticle or microparticle) adsorbed to an interface of the continuous fluorous phase and the aqueous phase droplet, and wherein the aqueous phase droplet comprises at least one hydrophilic polymer adsorbed to the amphiphilic particle at the interface (e.g., $PEG_{ads}$-F—$SiO_2NPs$).

Another aspect of some embodiments of the invention described herein relates to a Pickering emulsion comprising a continuous fluorous phase and at least one aqueous phase droplet dispersed therein, wherein the continuous fluorous phase comprises at least one partially fluorinated amphiphilic particle (e.g., nanoparticle or microparticle) adsorbed to an interface of the continuous fluorous phase and the aqueous phase droplet, and wherein the amphiphilic particle is covalently grafted with at least one hydrophilic polymer (e.g., $PEG_{covalent}$-F—$SiO_2NPs$).

Another aspect of some embodiments of the invention described herein relates to a droplet microfluidic device comprising a microfluidic channel, wherein microfluidic channel comprises a continuous fluorous phase and at least one aqueous phase droplet dispersed therein, wherein the continuous fluorous phase comprises at least one partially fluorinated amphiphilic particle (e.g., nanoparticle or microparticle) adsorbed to an interface of the continuous fluorous phase and the aqueous phase droplet, and wherein the aqueous phase droplet comprises at least one hydrophilic polymer adsorbed to the amphiphilic particle at the interface (e.g., $PEG_{ads}$-F—$SiO_2NPs$).

Another aspect of some embodiments of the invention described herein relates to a droplet microfluidic device comprising a microfluidic channel, wherein microfluidic channel comprises a continuous fluorous phase and at least one aqueous phase droplet dispersed therein, wherein the continuous fluorous phase comprises at least one partially fluorinated amphiphilic particle (e.g., nanoparticle or microparticle) adsorbed to an interface of the continuous fluorous phase and the aqueous phase droplet, and wherein the amphiphilic particle is covalently grafted with at least one hydrophilic polymer (e.g., $PEG_{covalent}$-F—$SiO_2NPs$).

The amphiphilic particles and fluorinated emulsions described herein have many applications. In some embodiments, the amphiphilic particles and fluorinated emulsions described herein are used for chemical reactions. In some embodiments, the dispersed phase droplets are used as reactors to synthesize other materials. In some embodiments, the fluorinated emulsions are used for organic or inorganic reactions. In some embodiments, the amphiphilic particles can be a support for a catalyst. In some embodiments, the amphiphilic particles themselves can be the catalyst for the reaction.

In some embodiments, the amphiphilic particles and fluorinated emulsions described herein are used for biochemical assays. In some embodiments, the amphiphilic particles and fluorinated emulsions described herein are used for cell-based assays (e.g., detection of bacteria, cell mechanics study, cell-based fermentation of yeasts, cell-based fermentation for the production of biofuels, etc.). In some embodiments, the amphiphilic particles and fluorinated emulsions described herein are used for small-molecule assays (e.g., drug screening, dose response, IC50, toxicity, antibiotic resistance, etc.). In some embodiments, the amphiphilic particles and fluorinated emulsions described herein are used for protein-based assays (e.g., enzymes, antibody, structure proteins, etc.). In some embodiments, the amphiphilic particles and fluorinated emulsions described herein are used for nucleic acid-based assays (e.g., PCR, LAPM, oligonucleotide, etc.).

These and other features, together with the organization and manner of operation thereof, will become apparent from the following detailed description when taken in conjunction with the accompanying drawings.

DETAILED DESCRIPTION

Fluorinated Pickering Emulsion

Described here are the design, synthesis, and application of amphiphilic silica nanoparticles to stabilize aqueous drops in fluorinated oils for applications in droplet microfluidics. The use of nanoparticles addresses two key limitations of current systems where drops are stabilized by surfactants: 1) the mitigation of undesirable inter-drop molecular transport which has severely compromised the accuracy of droplet assays. As particles are irreversibly adsorbed at the liquid-liquid interface and do not form micelles, one pathway through which molecules could leak is eliminated. 2) The biocompatibility with the growth of bacteria, and importantly the proliferation of adherent mammalian cells by providing a rigid solid-like interface to which cells could adhere and spread. The latter capability is not possible in surfactant-stabilized drops. The particles described herein thus address multiple limitations of surfactants commonly used in current droplet systems, and can allow new applications for high-fidelity assays and for the culture of anchorage dependent cells in droplet microfluidics.

One aspect of some embodiments of the invention described here relate to amphiphilic silica nanoparticles obtained by modifying the surface hydrophobicity of silica nanoparticles using silane chemistry to render the particles amphiphilic (i.e., partially wetted by the aqueous phase and partially wetted by the fluorous phase). The particles are initially dispersed in a continuous phase of fluorinated oils. In the presence of an aqueous phase, the particles adsorb spontaneously to the aqueous-fluorous interface. This approach has four key advantages: 1) The synthesis of silica nanoparticles and the modification of their surface chemistry are less burdensome compared with the synthesis of surfactants. The amphiphilic particles can be optimized to stabilize aqueous drops in multiple fluorinated oils (including HFE-7500, FC-40, and perfluoromethyldecalin (PFMD), whereas existing block copolymer surfactants are not all soluble in perfluorinated oils. 2) As the particles are initially dispersed in the continuous phase, they do not interfere with the reagents inside the aqueous drops. The generation of monodisperse drops can be performed using standard flow-focusing nozzles. 3) Particles are non-toxic to bacteria and mammalian cells. 4) The rigid solid-like interface given by the nanoparticles provides a favorable substrate for the attachment and spreading of adherent cells.

Silica nanoparticles are chosen instead of metallic nanoparticles here as the latter quench fluorescence from fluorophores that could be encapsulated inside the drops. The amphiphilic fluorinated SiO$_2$ nanoparticles are referred herein as "F—SiO$_2$ NPs".

Figure 1:
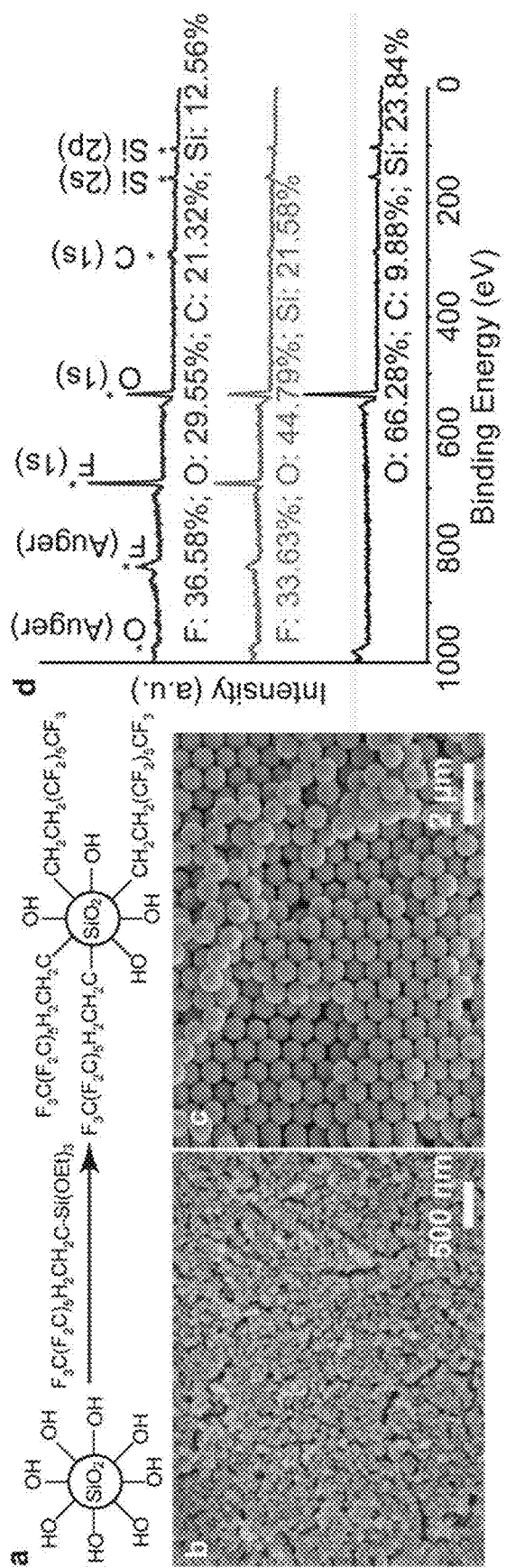
FIG. 1 shows: (a) Scheme of the fluorination process of $SiO_2$ NPs to form F—$SiO_2$ NPs. SEM images of F—$SiO_2$ NPs with diameters of approximately (b) 80 nm, and (c) 780 nm. (d) X-ray photoelectron spectra (XPS) of three particle samples having increasing degree of fluorination. Bottom curve: pristine $SiO_2$ before fluorination. Middle curve: F—$SiO_2$ NPs after 60 min of fluorination where the initial 1H-1H-2H-2H perfluorooctyl triethoxysilane (FAS) concentration was at $[FAS]_0$=118.7 mM. Top curve: F—$SiO_2$ NPs after 60 min of fluorination where $[FAS]_0$=502.3 mM. These three spectra correspond to samples A, B, and C in FIG. 8 respectively; the synthesis details of which are in Table 3.
Figure 7:
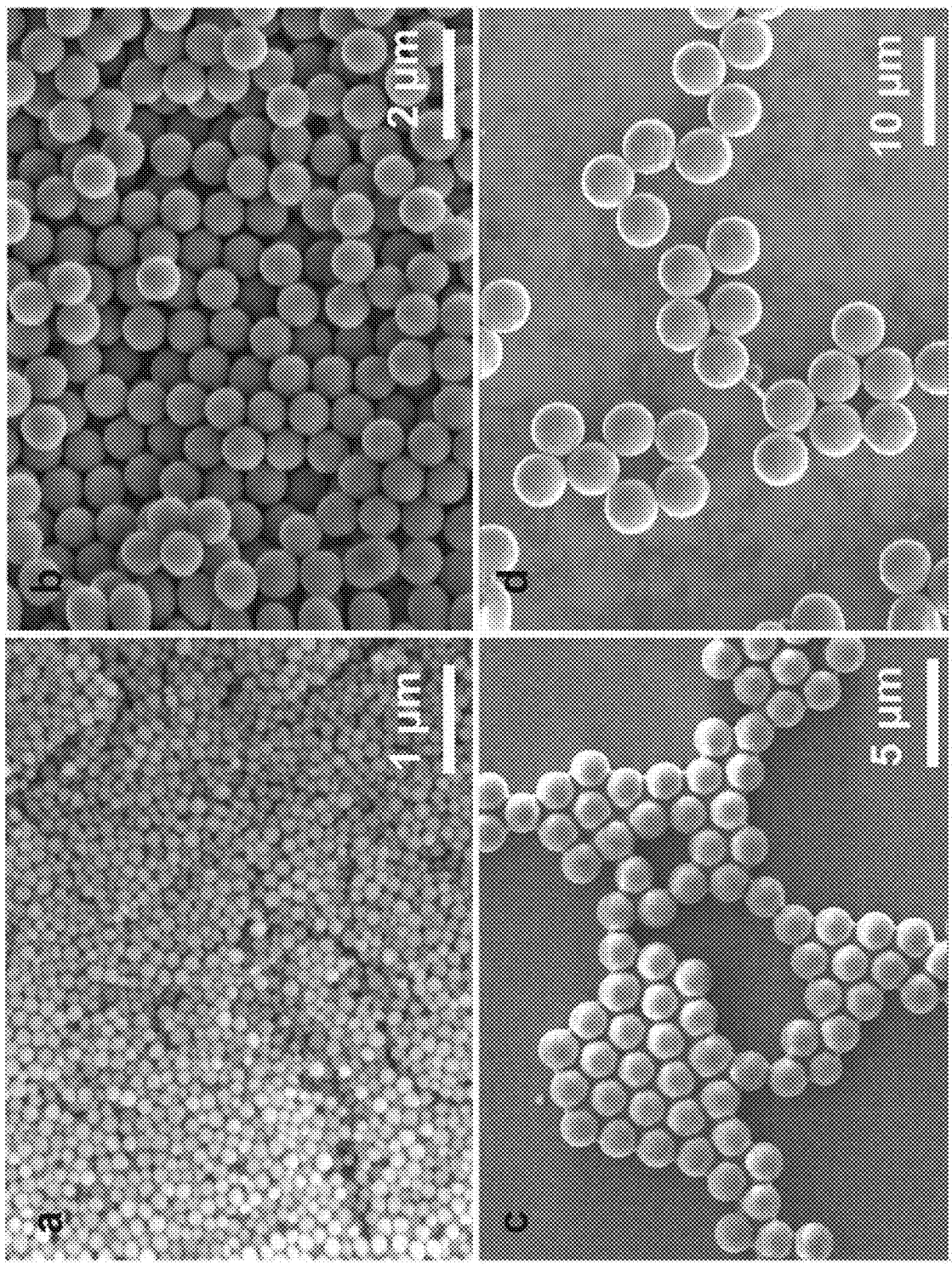
FIG. 7 shows SEM images of F—SiO$_2$ particles generated by fluorination of hydrophilic silica spheres having various sizes: (a) 150 nm, (b) 780 nm, (c) 2.01 µm, and (d) 5.20 µm respectively.

F—SiO$_2$ NPs were generated from the fluorination of pre-synthesized pristine SiO$_2$ NPs with diameters ranging from 50 nm to 1 μm. The SiO$_2$ NPs were either synthesized using Stober method, or purchased and used after centrifugation. The initial size of these SiO$_2$ NPs determined the final size of the F—SiO$_2$ NPs as the fluorination process did not change the size of the particles. The SiO$_2$ NPs were initially hydrophilic and dispersible in the aqueous phase. Particle surface fluorophilicity was increased by reacting the particles with 1H, 1H, 2H, 2H-perfluorooctyltriethoxysilane (FAS) to partially derivatize the silanol groups on the surface of pristine SiO$_2$ NPs (FIG. 1a). Details of the synthesis and fluorination are described in the working example section. FIGS. 1b and 7 show SEM images of the particles, either synthesized in house or purchased, after the fluorination process. X-ray photoelectron spectroscopy confirmed that the particles contained fluorinated groups after the fluorination process (FIG. 1c).

Figure 8:
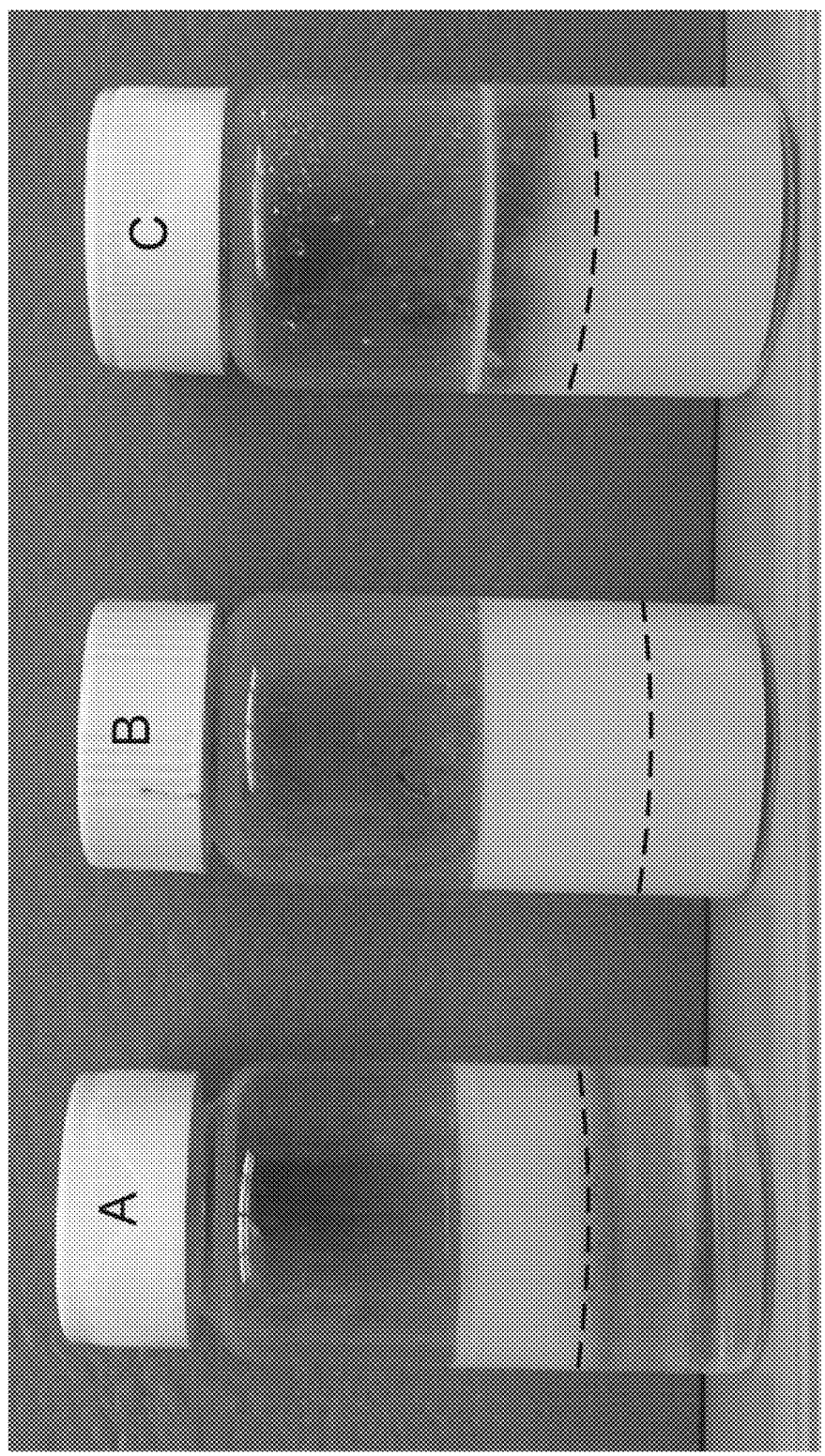
FIG. 8 shows photograph of solutions formed by agitating deionized water with (A) pristine SiO$_2$ NPs, (B) amphiphilic F—SiO$_2$ NPs, and (C) fluorophilic F—SiO$_2$ NPs respectively. The degree of fluorophilicity on the NPs was controlled by varying the initial concentration of 1H-1H-2H-2H perfluorooctyl triethoxysilane (FAS). Amphiphilic F—SiO$_2$ NPs produced stable emulsions, while other particles did not produce stable emulsions. Dashed lines indicate the interface between different phases.
Figure 9:
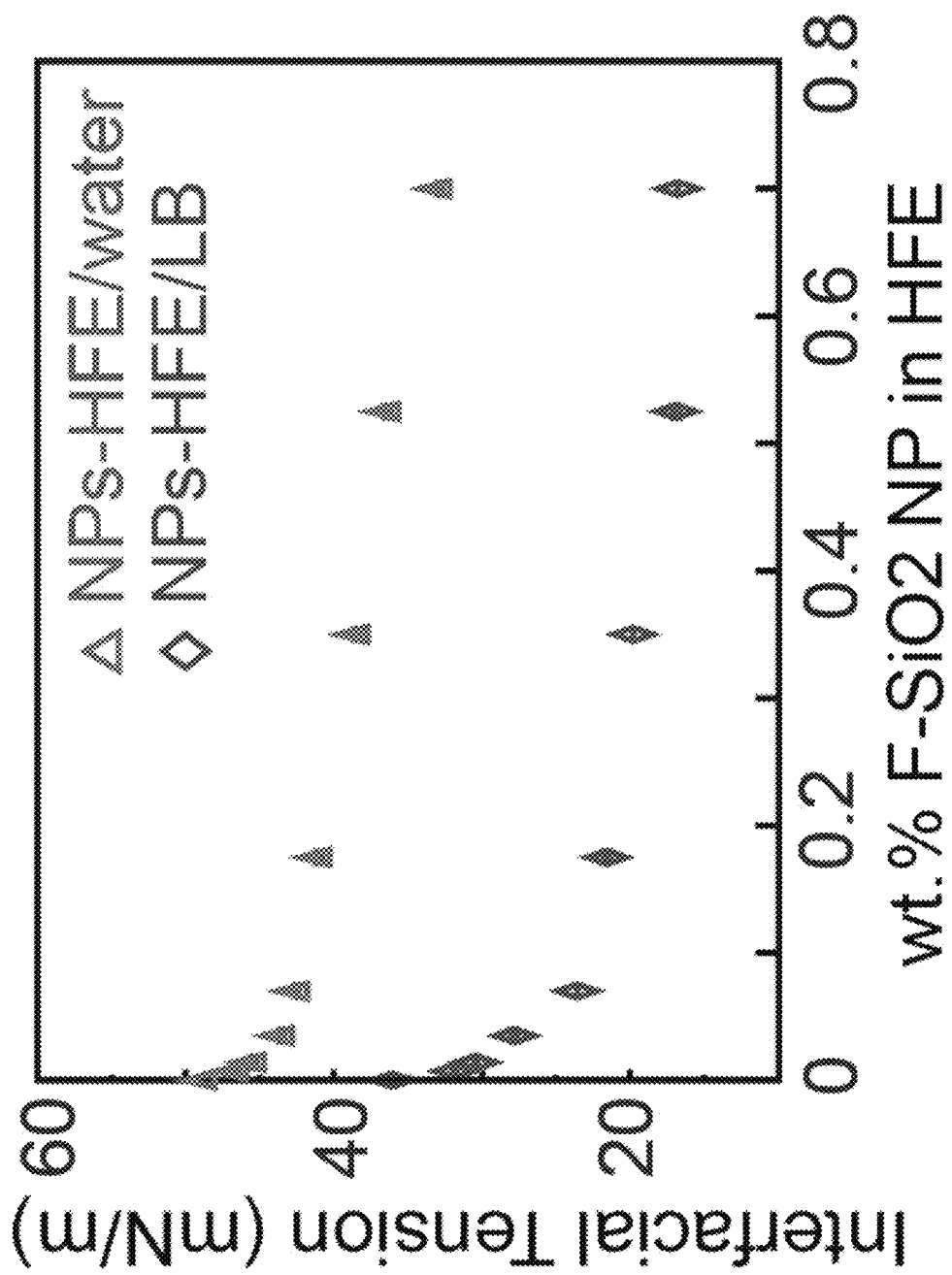
FIG. 9 shows interfacial tension between water (or LB) and HFE-7500 containing various concentrations of F—SiO$_2$ NPs. The NPs were dispersed in the fluorous phase, and the plateau indicates adsorbed NPs were likely to be saturated at interface.

To identify particles that could stabilize aqueous drops in various fluorinated oils, the particles were sampled at different times after the fluorination process started. The particles were dispersed in fluorinated oils, and agitated the dispersion with deionized water or Lysogeny Broth (LB), a growth media for bacteria, to form water-in-oil emulsions. After an optimal duration of fluorination (see Table 1 for details), the particles were partially wetted by both the aqueous phase and the fluorous phase. They spontaneously adsorbed to the aqueous-fluorous interface and generated stable emulsions for over 24 hours (FIG. 8). The stability of these emulsions formed by agitation was a good indicator of the stability of drops formed by microfluidic flow-focusing nozzles in subsequent experiments. Using a Wilhelmy balance (KSV NIMA, Espoo, Finland), the interfacial tension between water or LB and HFE-7500 containing various concentrations of F—SiO$_2$ NPs having a diameter of 52.1±10 nm (from dynamic light scattering) were measured. The particles were effective in decreasing the interfacial tension between the aqueous and the fluorous phases (FIG. 9). The plateau in the interfacial tension values above a concentration of about 0.5% (w/w) F—SiO$_2$ NPs in HFE-7500 indicates that the aqueous-fluorous interface was likely to be approaching complete coverage by nanoparticles. Based on the decrease in interfacial tension and an assumption that the particles at the interface were close-packed, it was estimated the adsorption energy of the particles to be ~$10^4$ k$_B$T. This large value indicates that particles were likely to be irreversibly adsorbed at the interface.

TABLE 1

Optimization of 1H-1H-2H-2H perfluorooctyl triethoxysilane (FAS) concentration and fluorination time to generate stable emulsions.

| Volume of 60 nm silica solution (mL) | Volume of FAS added (µL) | Time of particle isolation (min) | Stable water/HFE-7500 emulsion formed? |
|---|---|---|---|
| 5.25 | 50 | 60 | No |
| 5.25 | 250 | 60 | Yes (Sample B in FIG. 8) |
| 5.25 | 1250 | 60 | No (Sample C in FIG. 8) |
| 5.25 | 250 | 5 | No |
| 5.25 | 250 | 240 | No |

Figure 2:
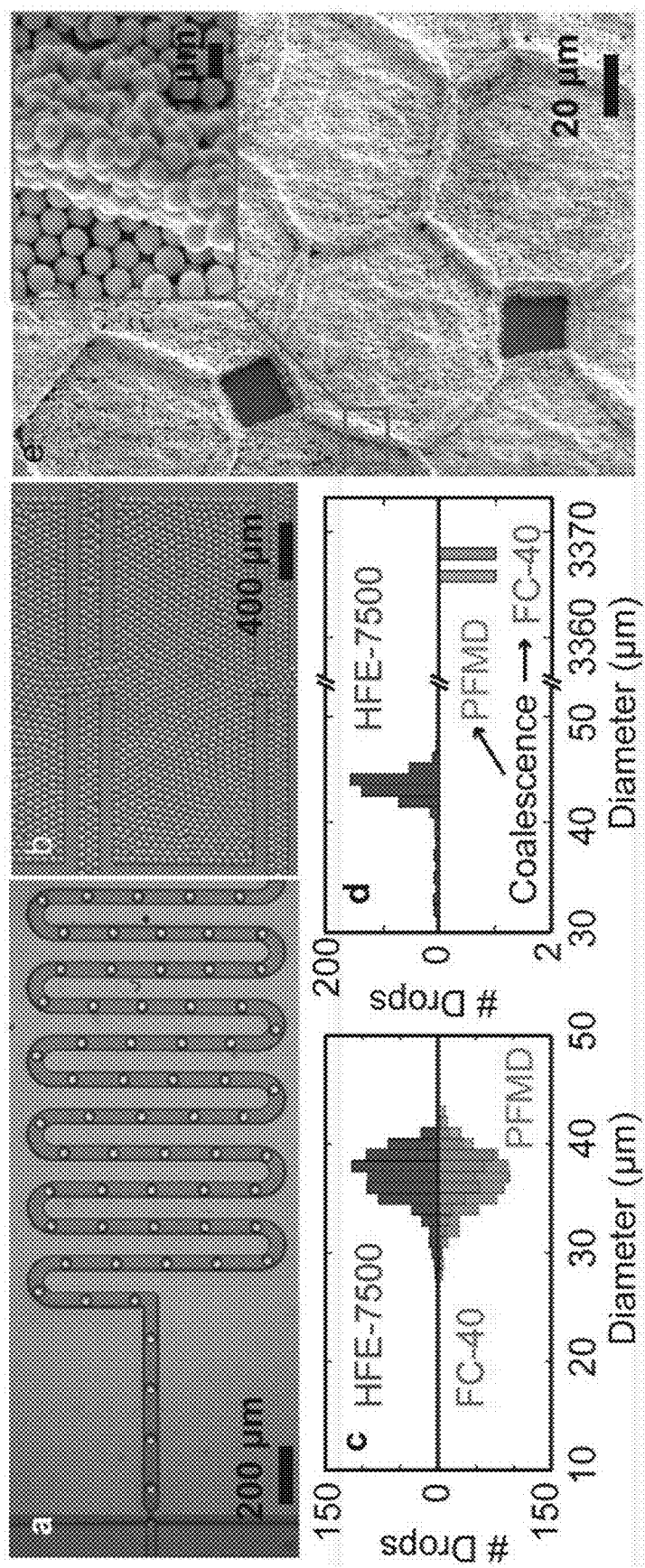
FIG. 2 shows: (a) A snapshot of drops of deionized (DI) water being generating from a flow-focusing device. The continuous phase contained 4.0% (w/w) of F—$SiO_2$ NPs in HFE-7500. (b) Optical image of DI water drops, stabilized by F—$SiO_2$ NPs, being reinjected into a 55 μm-tall microchannel. (c)-(d) Histograms of drop size distribution of DI water drops before and after the continuous phase was replaced by FC-40 and perfluoromethyldecalin (PFMD), where the drops were initially stabilized by a continuous phase of (c) F—$SiO_2$ NPs in HFE-7500 and (d) EA-surfactant in HFE-7500 respectively. Drops stabilized by EA-surfactants coalesced into single bulk aqueous phase when re-suspended in FC-40 and PFMD. (e) SEM image of nanoparticle-stabilized drops after excess particles were washed off from the continuous phase and the fluids were evaporated. The drops were stabilized by 780 nm F—$SiO_2$ NPs. The inset was SEM image taken from the box.
Figure 10:
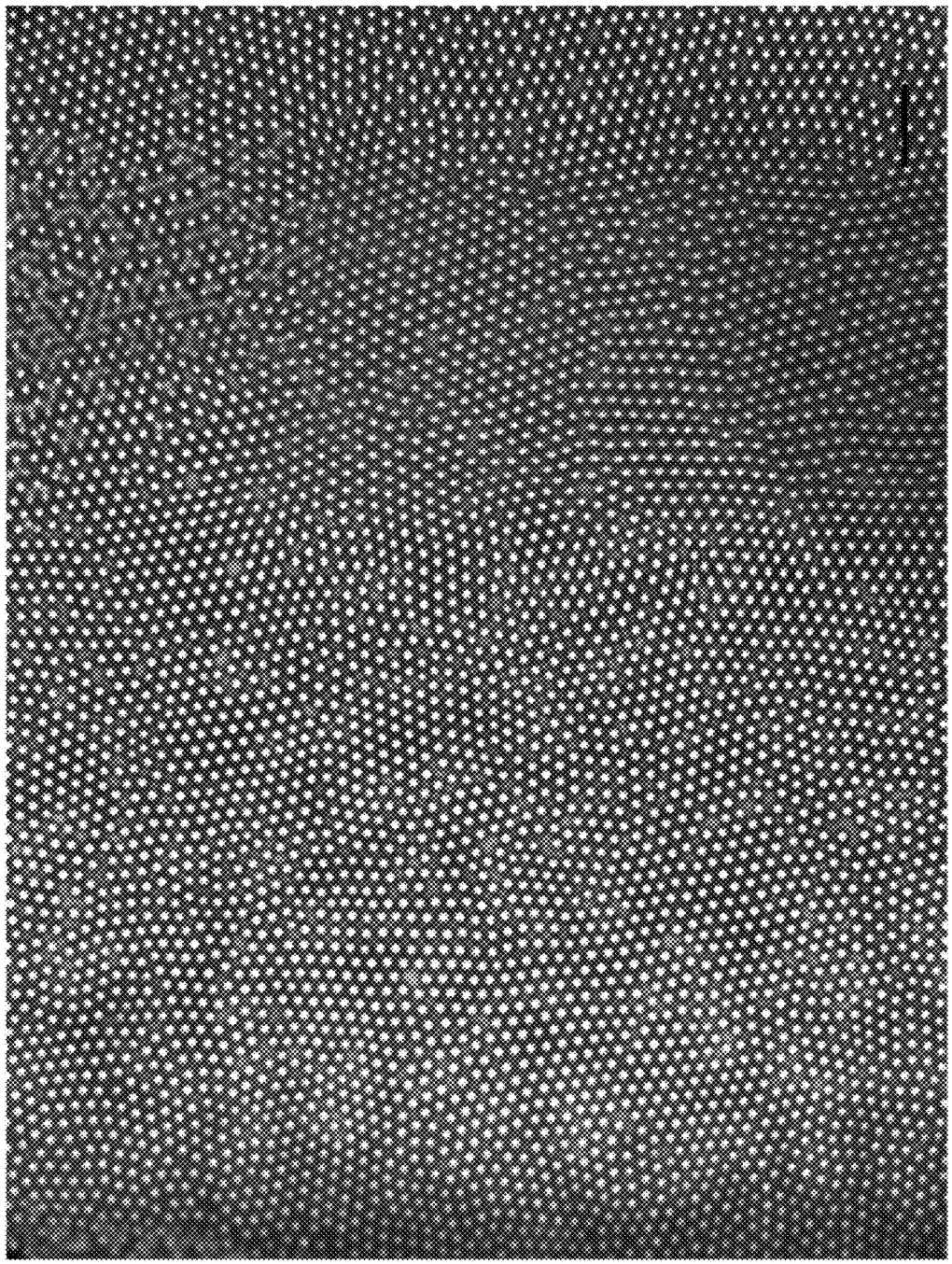
FIG. 10 shows optical image of close-packed 40 µm DI-water drops stabilized by 780 nm F—SiO$_2$ NPs in HFE-7500. Scale bar: 200 µm.
Figure 11:
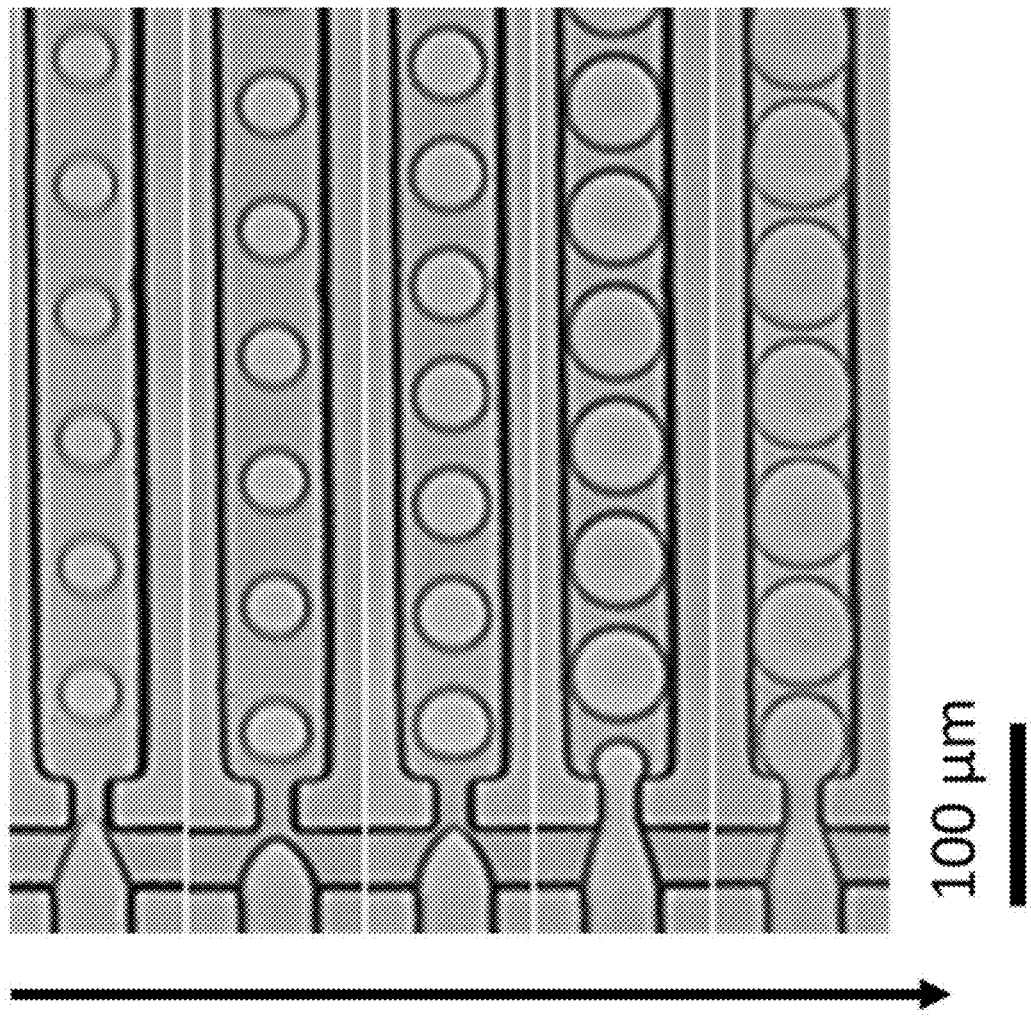
FIG. 11 shows drop size was controlled by varying the flow rate of the continuous phase containing nanoparticles with a diameter of 80 nm. The flow rate of dispersed phase was fixed at 0.5 mL/hr, and the flow rate of the continuous phase varied (top to bottom) from 2.0 mL/hr, 1.5 mL/hr, 1.0 mL/hr, 0.5 mL/hr, 0.4 mL/hr.
Figure 12:
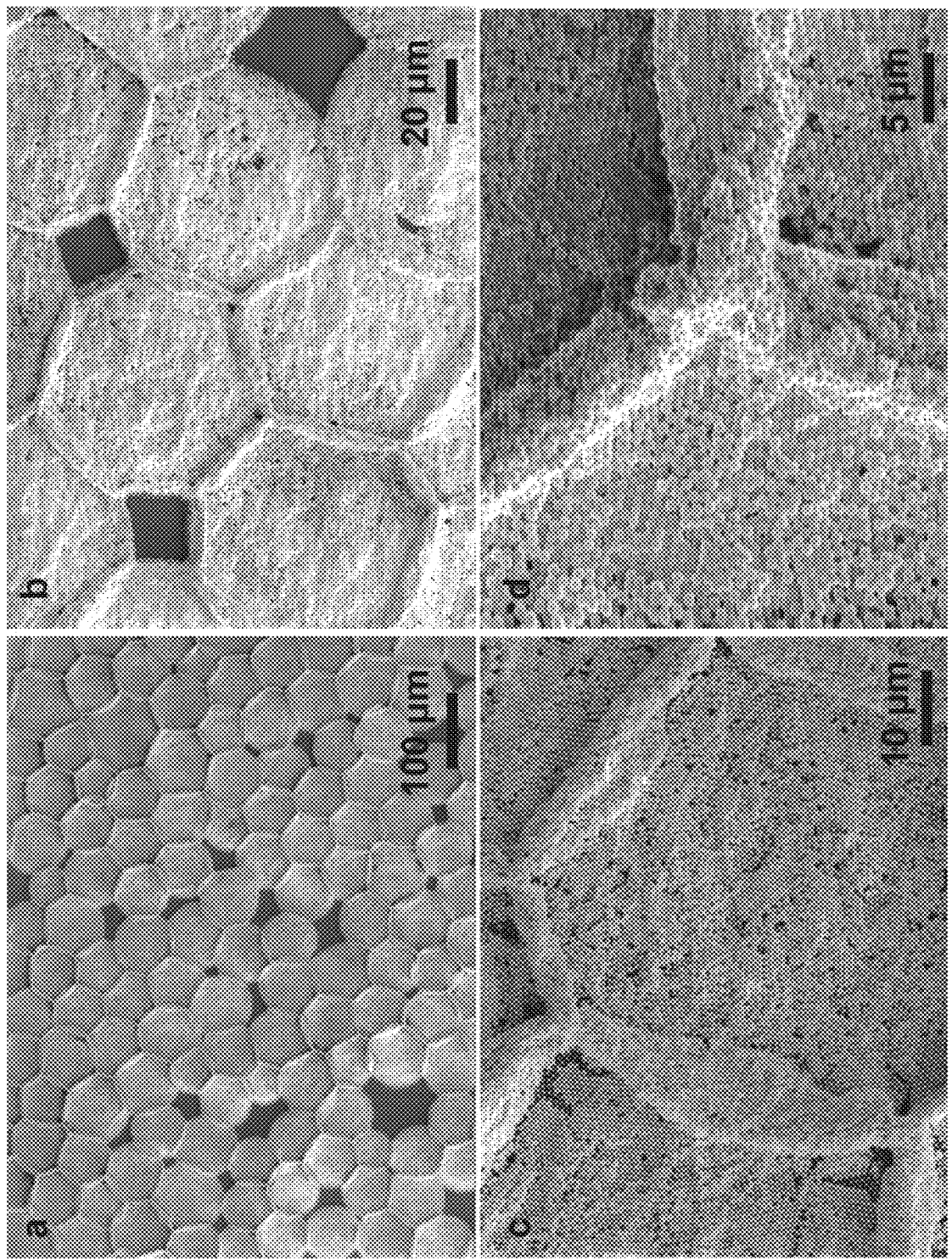
FIG. 12 shows SEM images of drops stabilized by F—SiO$_2$ NPs after excess particles from the continuous phase were washed off and after the fluids evaporated.
Figure 13:
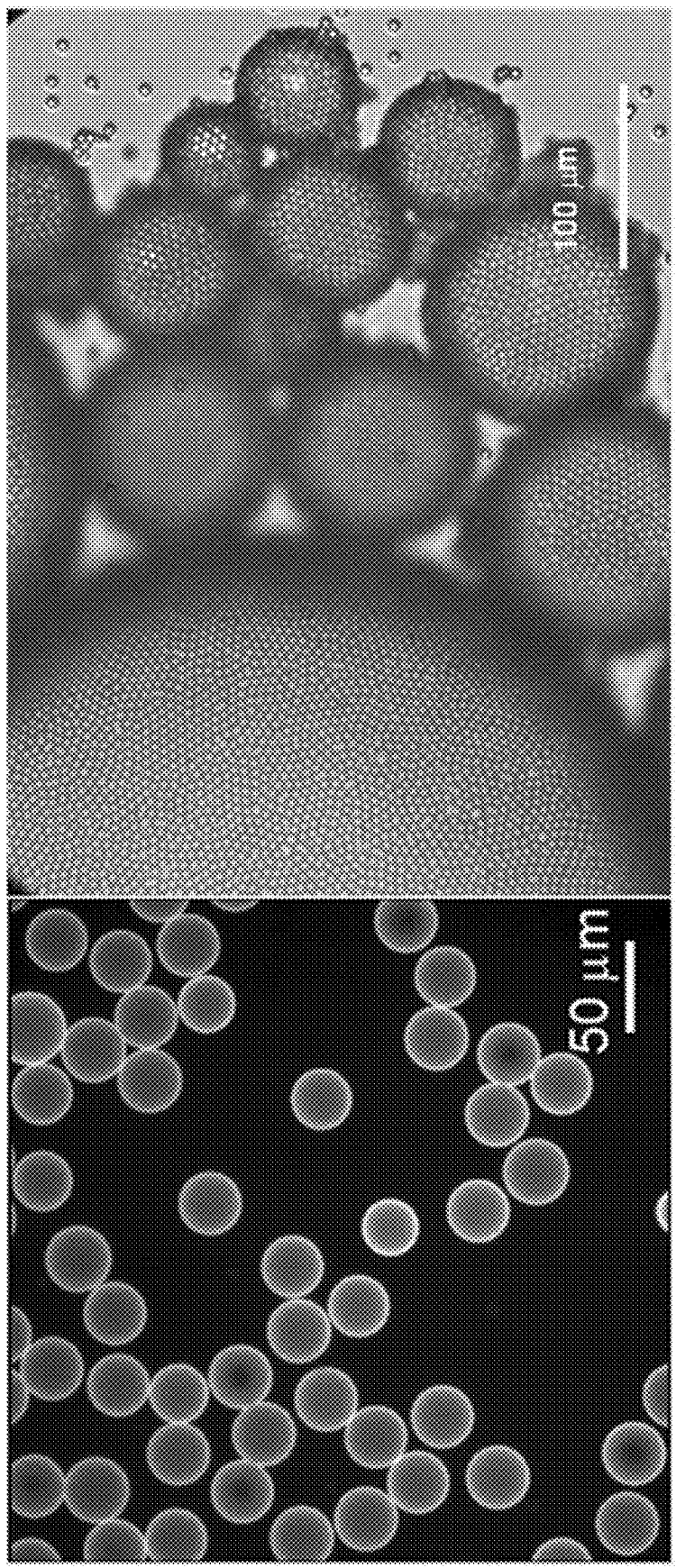
FIG. 13 shows: (a) Fluorescence image of drops stabilized by 80 nm F—SiO$_2$ NPs loaded with Rhodamine B. (b) Optical image of droplets stabilized by 5.20 µm F—SiO$_2$ microparticles (MP). The droplet surface was fully covered with a monolayer of MPs.

Based on the stability of emulsions formed by agitation (Table 1), particles that generated the most stable emulsions were identified, and their compatibility with microfluidics was demonstrated. Similar to surfactant systems, monodisperse drops stabilized by F—SiO$_2$ NPs can be generated using microfluidic flow-focusing nozzles. Here a single size of particles (780 nm) was investigated. The use of particles of other sizes did not change the results. Particles larger than 1 µm were increasingly likely to clog the channels after prolonged operation, however. FIG. 2a shows that drops generated from a flow-focusing nozzle were monodisperse with a coefficient of variance CV≈0.8%. This value is comparable with the typical value of CV for drops stabilized by surfactants (typically smaller than 3%). Using a single flow-focusing nozzle (nozzle dimensions: 40 µm×30 µm), droplet volume was tunable from 22.4 pL to 127 pL by changing the flow rate (from 0.4 mL/hr to 2 mL/hr) of the continuous phase containing 2% (w/w) of particles in HFE-7500 (also see FIG. 11). A serpentine channel with a length of 10 cm to 20 cm downstream of the nozzle was used to ensure sufficient time for particles to adsorb to the droplet interface. These particle-stabilized drops were stable upon incubation and shaking at 100 rpm in bulk in an Eppendorf tube at 37° C., and upon reinjection into a microchannel (FIGS. 2b and 10). Furthermore, these drops remained intact and did not coalesce when re-suspended in neat HFE-7500, as well as perfluorinated solvents FC-40 and PFMD (FIG. 2c). Such observations were consistent with the expectation that the particles were irreversibly adsorbed at the liquid-liquid interface, as the adsorption energy was estimated to be ~$10^6$ k$_B$T for particle diameter of 780 nm. On the other hand, the adsorption energy of surfactants is typically on the order of a few k$_B$T. Drops stabilized by surfactants coalesced readily upon re-suspension in perfluorinated solvents (FIG. 2d). As particle-stabilized drops were stable upon re-suspension in neat solvents, it was possible to wash off excess particles in the continuous phase and selectively image the particles that were adsorbed at the aqueous-fluorous interface. SEM images of the drops, after the aqueous and fluorous phases evaporated, show that the drops were fully covered by particles (FIG. 2e, also see FIG. 12-13).

Figure 3:
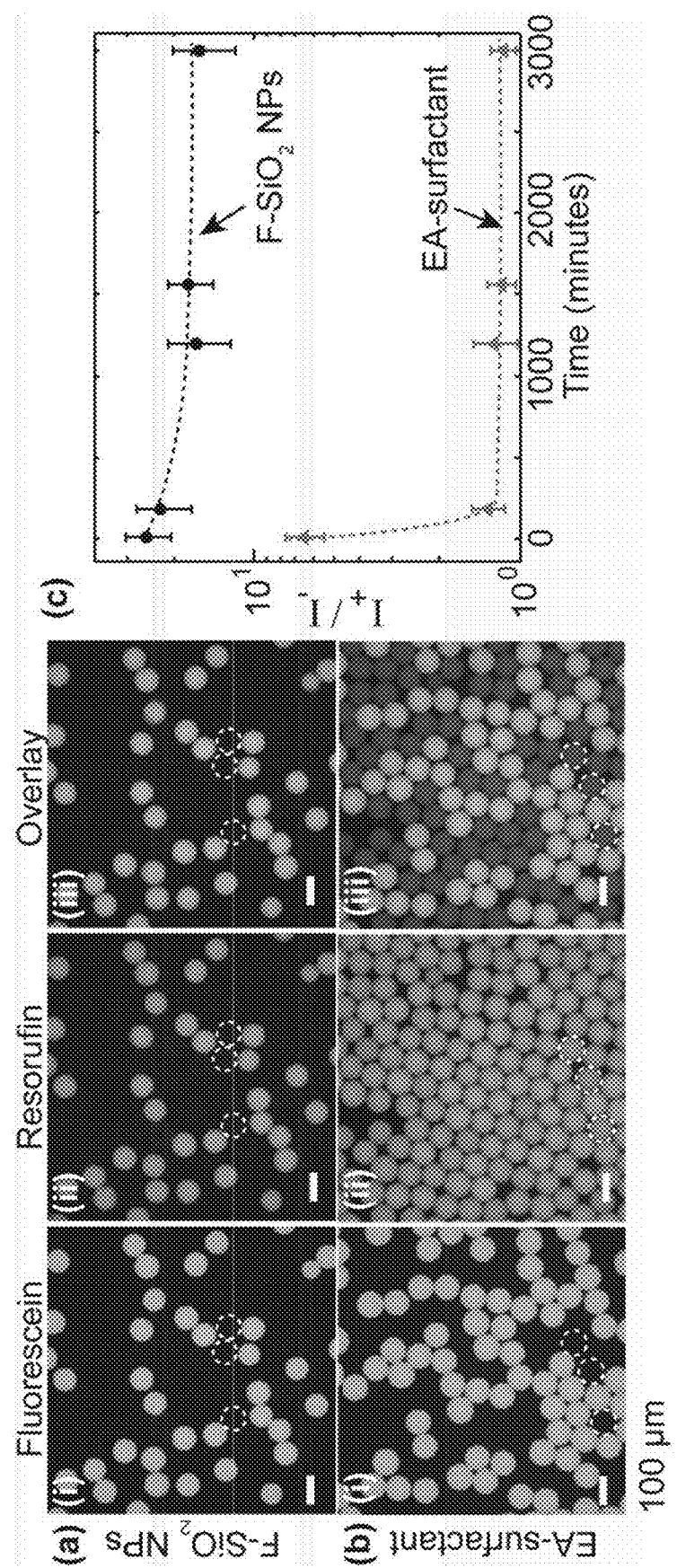
FIG. 3 shows: (a) Fluorescence images of "positive" and "negative" drops stabilized by F—$SiO_2$ NPs after mixing for 26 hrs. The emulsion contained a 1:1 mixture of "positive" drops containing fluorescein (10 μM) and resorufin (220 μM), and "negative" drops containing PBS buffer only. Fluorescein was used to tag the positive drops. Fluorescence image of (i) fluorescein, (ii) resorufin, and (iii) an overlay of fluorescein and resorufin, respectively. If there was no leakage, the fluorescein and resorufin drops should overlap in (iii) and should appear yellow. Three negative drops are outlined in dashed circles. The colors were added during post-processing of data. (b) Fluorescence images of drops stabilized by EA-surfactant after mixing for 26 hrs. All conditions are identical to (a) except F—$SiO_2$ NPs are replaced by EA-surfactants. Three negative drops are outlined in dashed circles. All scale bars in (a) and (b) are 100 μm. (c) Plots of the time evolution of the ratio of resorufin fluorescence intensity of positive drops ($I_+$) versus that of negative drops (I_), for drops stabilized by F—SiO$_2$ NPs and EA-surfactants respectively. The mean value is calculated from 1191 F—SiO$_2$ NPs stabilized drops and 1064 EA-surfactant stabilized drops respectively, and the height of the error bars represents one standard deviation from the mean. Dashed lines are fitted curves to the data.
Figure 14:
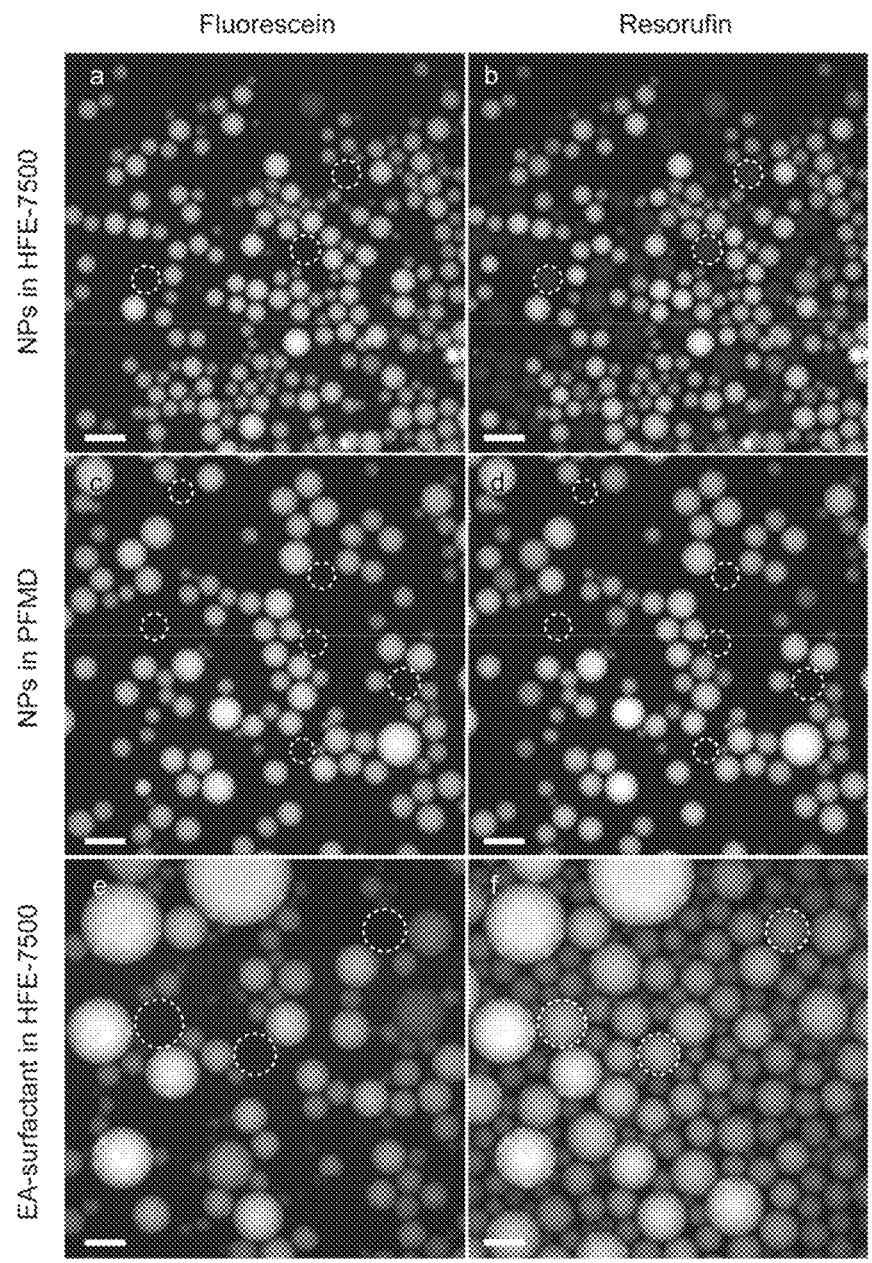
FIG. 14 shows fluorescence images showing the results of the leakage test of resorufin from droplets that are stabilized by (a-b) 780 nm F—SiO$_2$ NPs in HFE-7500, (c-d) 780 nm F—SiO$_2$ NPs in PFMD and (e-f) EA-surfactant in HFE-7500 after incubating for 44 hours. The procedures were the same as that in FIG. 3, except that these drops were produced by vortexing. Some of the negative drops were indicated by dashed circles. Scale bars: 100 µm.

F—SiO$_2$ NPs were effective in preventing the leakage of resorufin, a model dye that can leak from drops stabilized by EA-surfactant. In an assay to measure leakage, two types of drops were generated. "Positive" drops contained a mixture of resorufin and fluorescein. Fluorescein does not leak in drops stabilized by surfactants for at least 36 hours, and was thus used to tag the positive drops. "Negative" drops contained buffer only. By mixing the positive and negative drops, the leakage of resorufin can be characterized by measuring the time evolution of resorufin fluorescence intensity among positive and negative drops. FIG. 3 shows that after 26 hours of incubation at 20° C., the resorufin fluorescence intensity became homogenized in drops that were stabilized by surfactants, indicating leakage of the dye. The resorufin intensity in positive drops decreased almost immediately upon mixing (FIG. 3c), explaining the small ratio of resorufin fluorescence intensity of positive drops (I$_+$) versus that of negative drops (I$_-$) at the first time point. This ratio (I$_+$/I$_-$) decreased to a value of about 1 in less than 180 minutes (FIG. 3c). On the contrary, the leakage of resorufin was insignificant in drops stabilized by F—SiO$_2$ NPs in FC-40. The value of I$_+$/I$_-$ remained >15 even after 50 hours of mixing. Since nanoparticles do not form surfactant micelles, the primary role of the F—SiO$_2$ NPs was the elimination of such micelles which had been reported to increase the leakage rate among aqueous droplets. FC-40 was used instead of HFE-7500 to suspend the particles here, as slow leakage of resorufin was observed when the drops were stabilized by F—SiO$_2$ NPs in HFE-7500, though this leakage was significantly slower than that in surfactant system (FIG. 14). It could be that resorufin directly partition more readily into HFE-7500 (which contained an aliphatic ether group) than into FC-40 and PFMD which are completely fluorinated. F—SiO$_2$ NPs could also be effective in preventing the leakage of other fluorophores.

Figure 4:
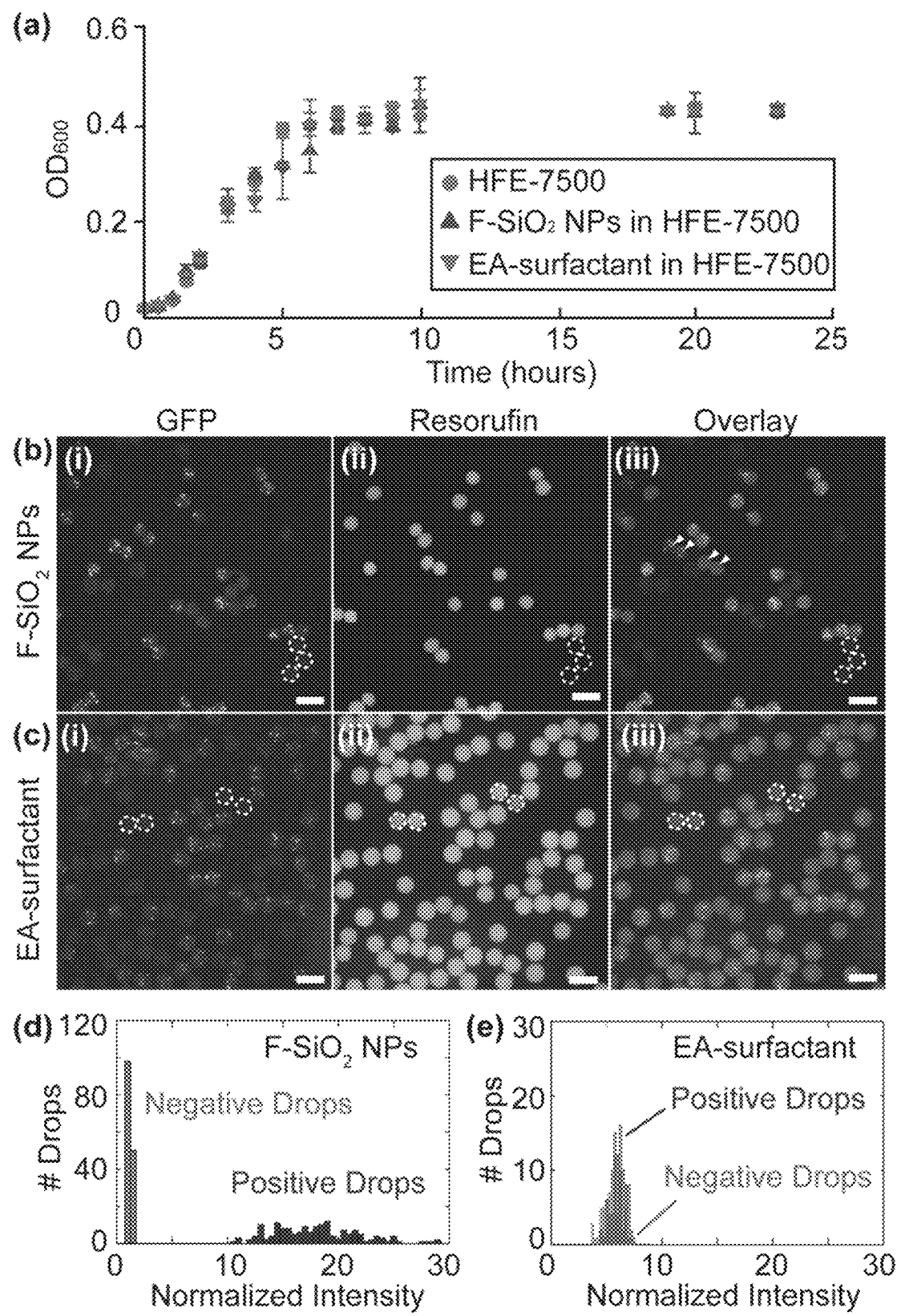
FIG. 4 shows: (a) Bacteria growth curve when the culture was suspended on top of HFE-7500, in drops stabilized by F—SiO$_2$ NPs in HFE-7500, and in drops stabilized by EA-surfactants in HFE-7500 respectively. The initial OD$_{600}$ value was about 0.001, and each drop contained, on average, less than one cell. The cell suspensions were incubated in a shaker-incubator at 37° C. and 250 rpm for 24 hours. To measure the OD$_{600}$ from drops stabilized by F—SiO$_2$ NPs, the emulsion was destabilized by adding mineral oil to the emulsion followed by agitation and centrifugation to separate the aqueous phase from the fluorous phase. (b-c) Drops stabilized by (b) 780 nm F—SiO$_2$ NPs and (c) EA-surfactants respectively. Fluorescence images of (i) E. coli expressing green fluorescent protein (GFP), (ii) resorufin, and (iii) an overlay of resorufin and GFP, respectively. Positive drops containing E. coli expressing GFP and resazurin (60 µM) were mixed with negative drops containing buffer for 2 hours. Several negative drops are outlined in dashed circles. The colors were added during post-processing of data. The 4 arrows indicate drops that shifted in position between imaging of the resorufin and GFP. (d-e) Histograms of resorufin fluorescence intensity distribution for positive and negative drops.

As a first test of biocompatibility of the nanoparticles, the growth rate of E. coli were compared, as measured by an increase in the optical density of cell suspension at 600 nm (OD$_{600}$), when the cells grew: i) in contact with HFE-7500 without any surfactants or nanoparticles, ii) inside drops stabilized by the biocompatible EA-surfactant in HFE-7500, and iii) inside drops stabilized by F—SiO$_2$ NPs in HFE-7500. Both HFE-7500 and EA-surfactant have been shown previously to be biocompatible. FIG. 4a shows that the growth curves of E. coli in all cases were indistinguishable within experimental error. This observation indicates that F—SiO$_2$ NPs did not affect the division of E. coli. In addition, FIG. 4b shows that F—SiO$_2$ NPs did not interfere with a standard cell viability assay based on the metabolic reduction of resazurin (barely fluorescent) to resorufin (fluorescent), and that the presence of growth media and high concentrations of E. coli did not cause dye leakage. E. coli expressing green fluorescent protein (GFP) were used such that "positive" drops that contained E. coli and resazurin can be identified from "negative" drops that contained buffer only. Initially, all drops were dark as resazurin had low fluorescence levels. At time t=120 min, the fluorescence intensity from positive drops stabilized by F—$SiO_2$ NPs increased significantly and were distinguishable from the negative drops with no E. coli. For drops stabilized by EA-surfactant, fluorescence intensity of all drops increased due to the leakage of resorufin.

Figure 15:
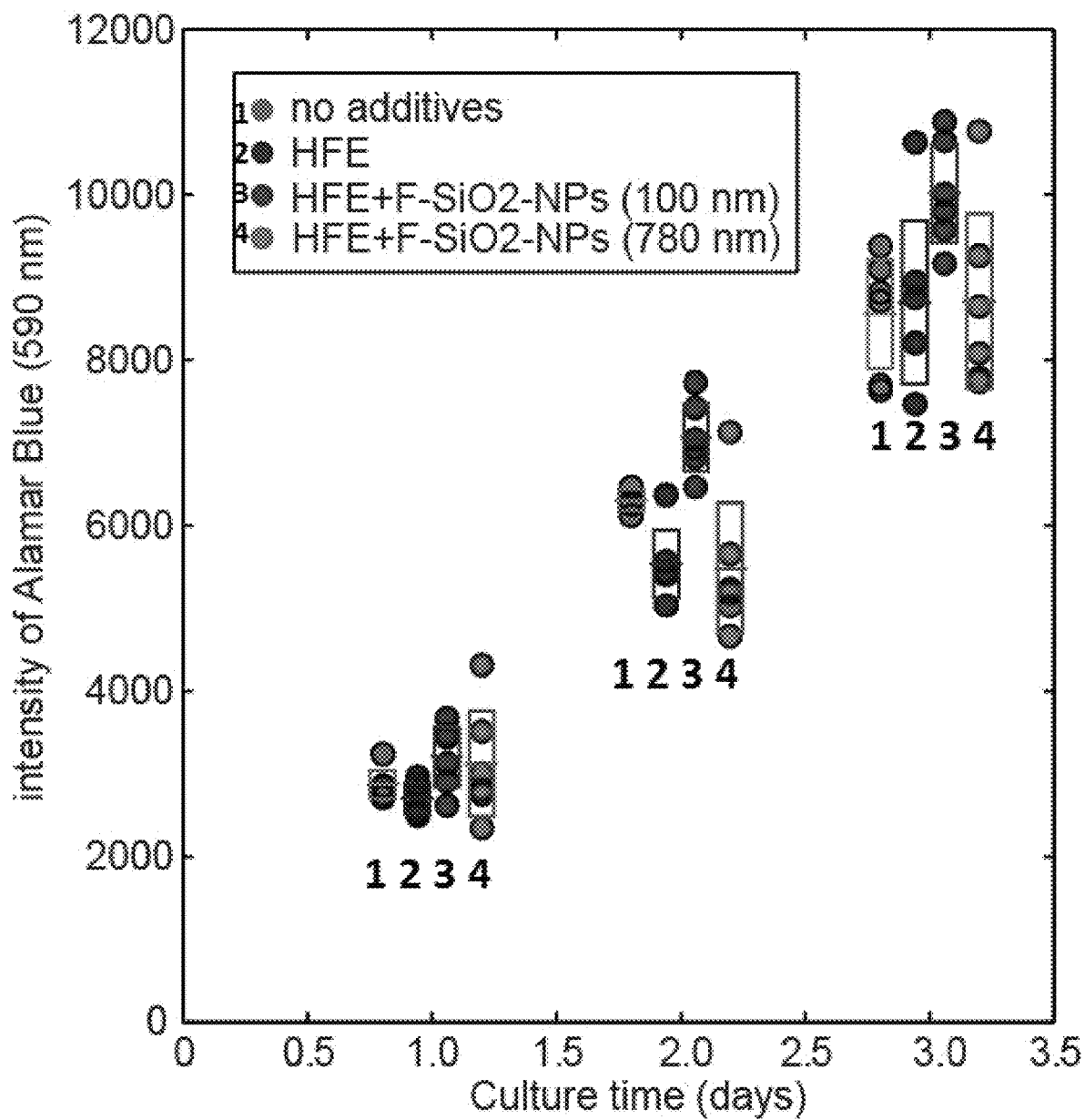
FIG. 15 shows nanoparticle suspension in HFE-7500 has no effect on the rate of proliferation of 3T3 Fibroblasts cells. The cells were seeded in 96-well plate at the density of 5000 cells per well in 200 µL of complete growth medium (MEM+10% CBS). After adhesion for 24 hours, each well was supplemented with 5 µL of HFE-7500 or 5 µL of 1% w/v suspension of F—SiO$_2$ NPs in HFE-7500. In each case, a coarse emulsion of fluorous drops was formed at the bottom of the well. Control wells were not supplemented with any fluorous oils. After 1, 2, or 3 days of culture, the culture media was removed, and a 200 µL of solution of commercial Presto Blue (PB) reagent in complete growth medium (1:10 w/w PB:medium) was immediately added. After 3 hours, 100 µL of supernatant was transferred and measured the evolved fluorescence in the solution using fluorescent plate reader (560 nm excitation/590 nm emission). The number of cells on days 1-3, as measured by turnover of PB, was indistinguishable in all four treatment groups (with or without HFE or nanoparticles). The data represent measurement from 6 independent wells; all data points are shows; rectangles are centered on population average and have the height equal to 2× (standard deviation). The data series were offset along the x-axis to ease avoid extensive overlap of data and simplify the visualization.

It was demonstrated that F—$SiO_2$ NPs were not toxic to mammalian cells, and could provide a solid-like interface for the adhesion and growth of these cells. Guided by the studies with E. coli, a toxicity assay was designed using cells cultured in 96-well plate in the presence of 5% (v/v) of HFE-7500 that contained F—$SiO_2$ NPs. 3T3 fibroblasts cultured in the presence of F—$SiO_2$ NPs exhibited the same growth rate over three days as cells cultured on polystyrene without the nanoparticles (FIG. 15). Neither 100 nm nor 780 nm nanoparticles had any effect on the rate of growth of these cells.

Figure 5:
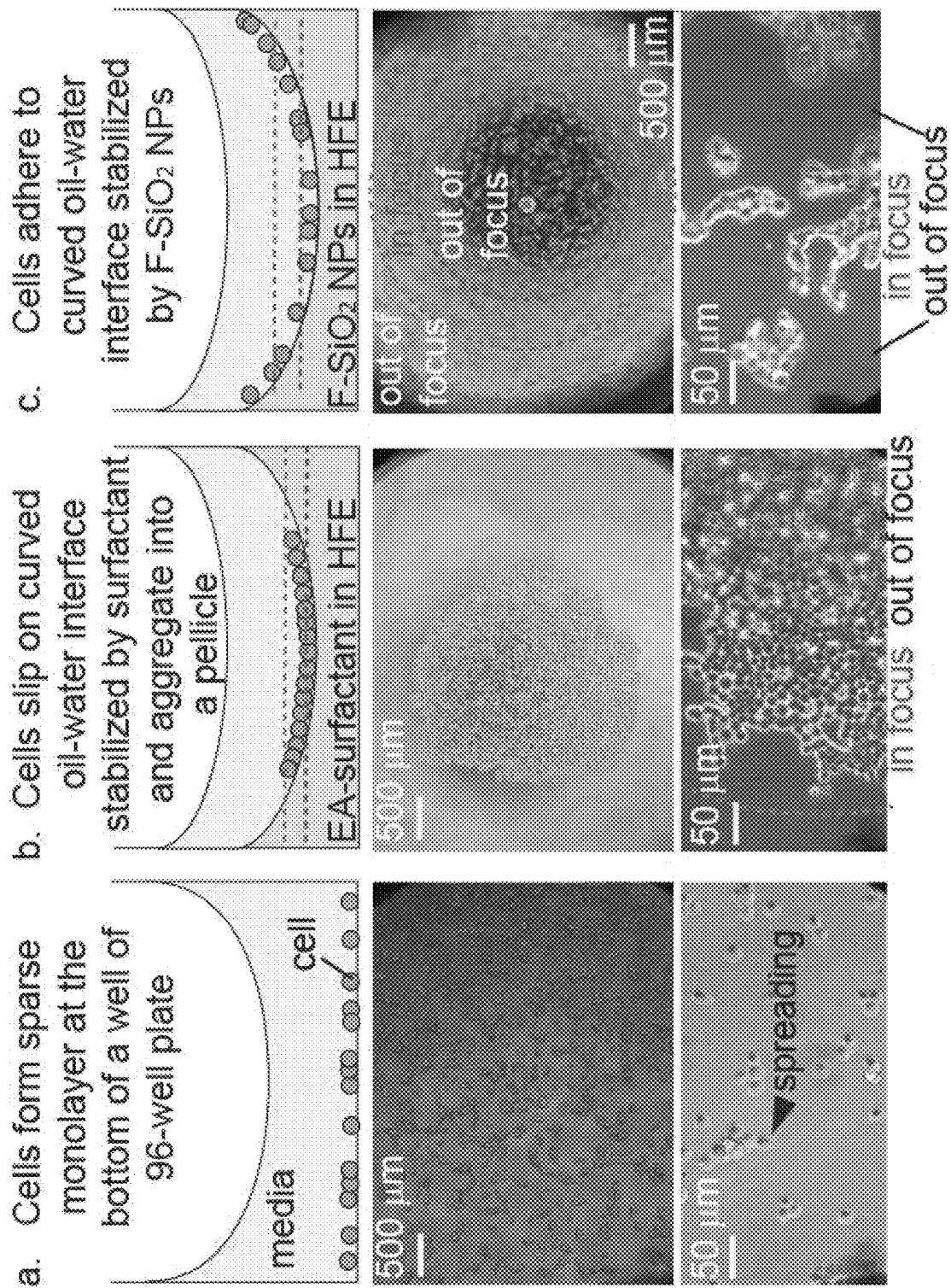
FIG. 5 shows adhesion or slipping of mammalian cells on curved water-oil interface. (a) Short term adhesion of MCF-7 cells to solid surface (hydrophobic polystyrene). (b) Same number of cells plated in a well that contains curved water-oil interface. The oil composed of EA-surfactant in HFE-7500. The cells cannot be retained on the interface and they slip and form a curved 2D aggregate in the center of the well. (c) Same cells adhering to curved water-oil interface stabilized by F—SiO$_2$ NPs. The cells adhere across the entire interface and do not slip. The edge and the center of curved water-oil interface are in different focal planes. The green and red dashed lines indicated approximate borders of areas that are in focus.

In addition, it was observed that anchorage-dependent cells, such as fibroblasts and luminal breast carcinoma MCF-7, attached to an inclined fluorinated water-oil interface stabilized by F—$SiO_2$ NPs. This finding would be surprising according to previous work which showed that the interface between fluorinated oil or air and water was non-fouled by biological contaminants such as serum, blood, and biofilm-promoting bacteria cells. The water-oil interface is "slippery" and such interfaces, when inclined, should not retain cells or serum proteins to which cells adhere. To investigate both adhesion and slipping, a curved aqueous-fluorous interface was formed inside individual wells in a 96-well plate by placing 100 µL of cell suspension on top of 100 µL of HFE-7500 containing EA-surfactant or F—$SiO_2$ NPs (FIG. 5). The fluorous phase preferentially wets the well surface to generate a concave aqueous-fluorous interface. Droplets were not used here to facilitate imaging of cell morphology at the interface; however, similar cell behavior on curved water-oil interfaces inside aqueous drops was anticipated.

Figure 6:
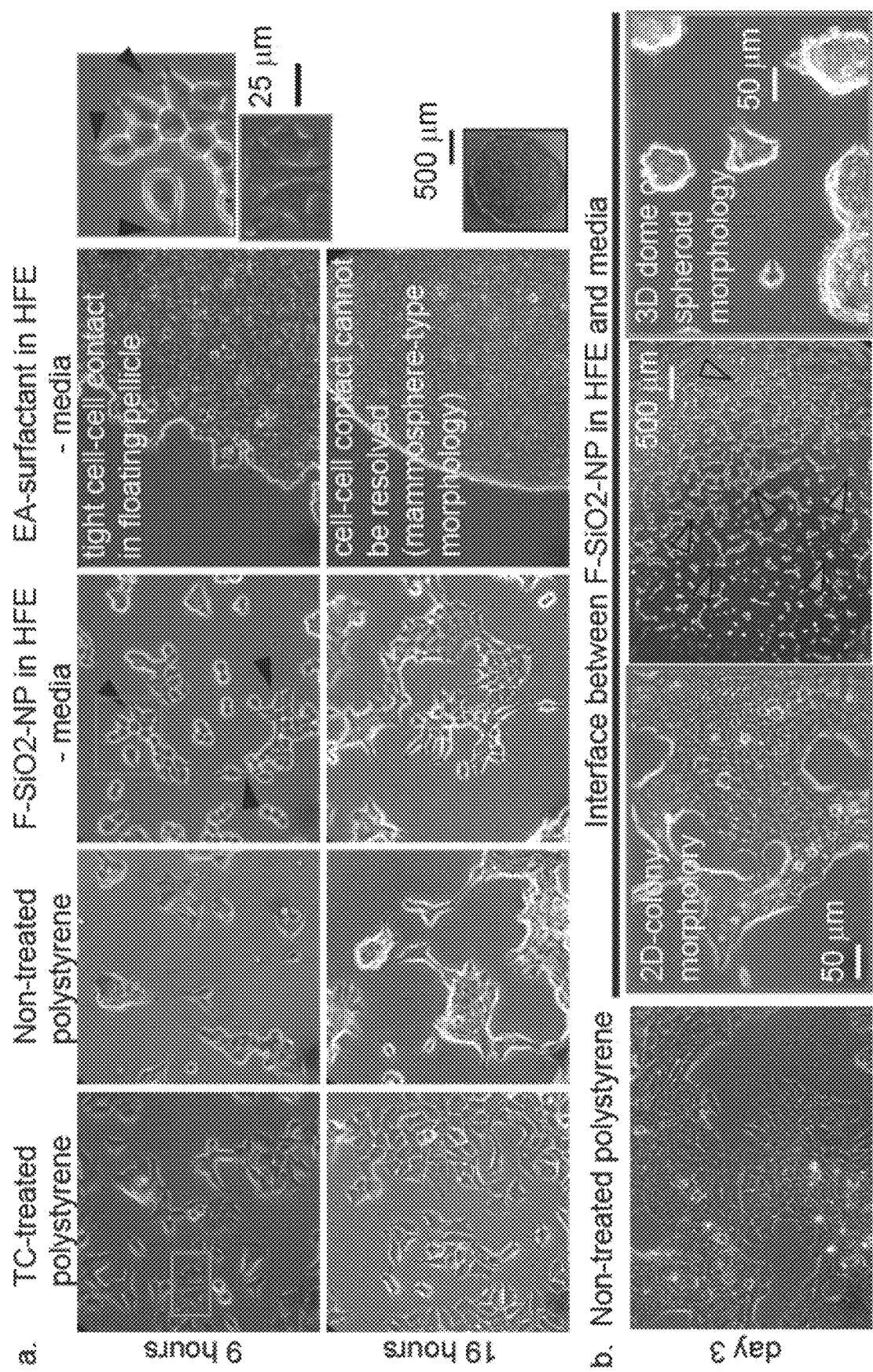
FIG. 6 shows short-term spreading and growth of cells on solid and liquid interfaces. (a) Dynamics of short term spreading (19 hours) of breast cancer MCF7 cells on liquid-solid and liquid-liquid interfaces in serum-containing media. On tissue-culture treated (TC) polystyrene, cells form filopodia within 3 hours and spread after 5 hours. Spreading is delayed on hydrophobic non-treated polystyrene with cells starting to spread at 5 hours and complete spreading by 19 hours. Similar spreading behaviour is observed on the interface of HFE-7500 stabilized by 100 nm nanoparticles. In contrast, the same liquid-liquid interface stabilized by EA-surfactant cannot support adhesion of cells; instead, cells aggregate and compact into an ellipsoid-shaped mammosphere. (b) Over the course of 3 days, cells fully-spread and proliferate on polystyrene. Cells on nanoparticle-stabilized interface exhibit mixed morphology: they form two-dimensional colonies composed of spread-out cells or compact 3D colonies.
Figure 16:
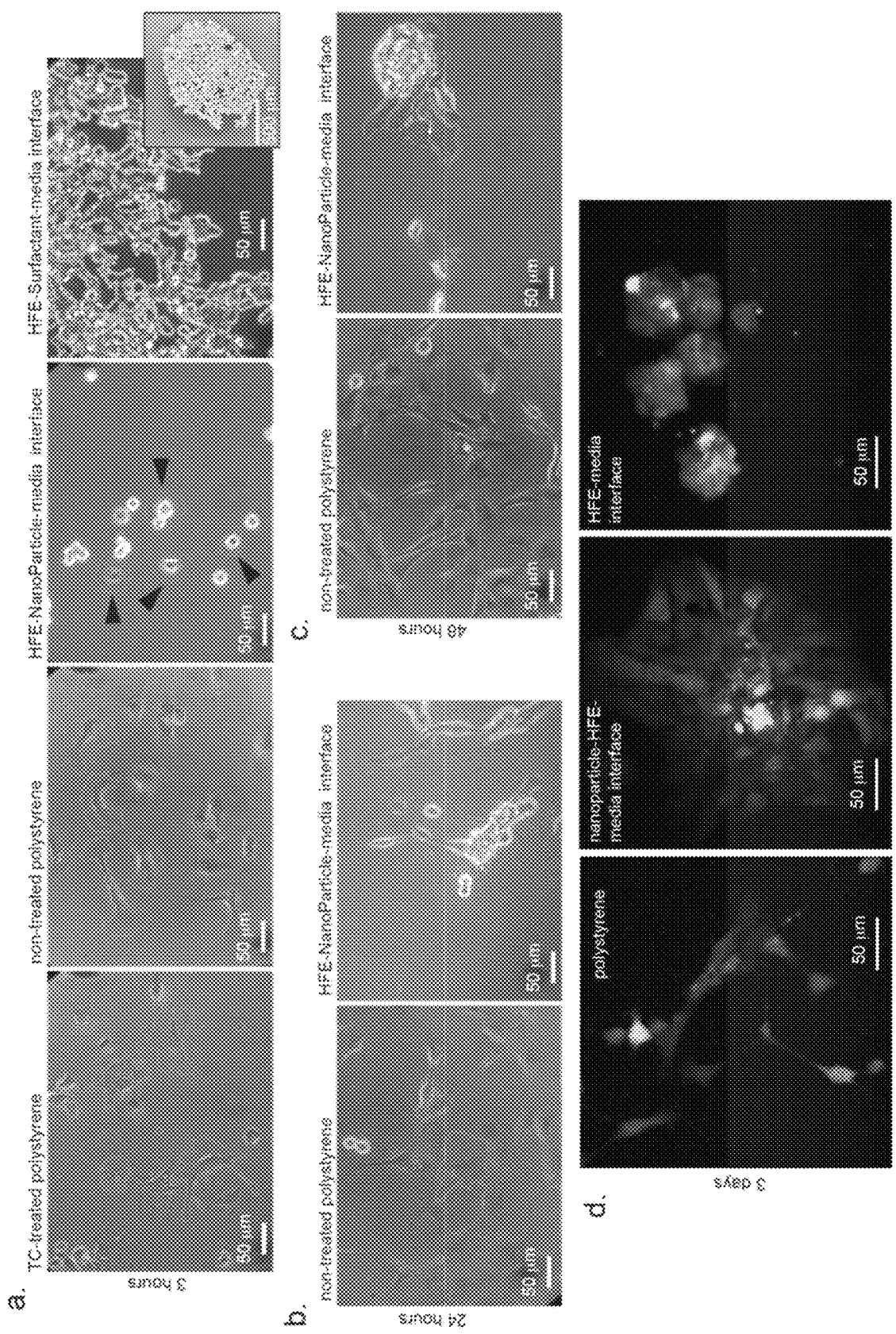
FIG. 16 shows anchorage-dependent 3T3 fibroblasts cells on solid-liquid and liquid-liquid interfaces in serum-containing media. (a) After 3 hours adhesion, cells spread completely on polystyrene surface (treated or non-treated). About 20-30% of cells also spread out on NP-stabilized oil-water interface although the spreading area is significantly lower than on polystyrene. In contrast, surfactant-stabilized interface cannot support cell adhesion or spreading and cells aggregate into a lose cell cluster in the middle of the well (see low-resolution inset). Images describe seeding of 5000 cells in well of 96-well plate. (b-c) Over the course of 1-2 days, cells fully spread and grow on polystyrene. On NP-interface, they exhibit mixed morphology of spread-out and aggregated cells. (d) Fluorescence image of 3T3 fibroblasts stained using carboxyfluorescein succinimidyl ester (CFSE). Cells were stained on day 0, seeded on polystyrene or interface of HFE-nanoparticle-media or HFE-media and allowed to grow for 3 days. Cells were then imaged using laser-scanning confocal microscope. Spreading area of cell on nanoparticle-reinforced interface and polystyrene is similar. In contrast, cell on HFE do not spread and form aggregates instead.
Figure 17:
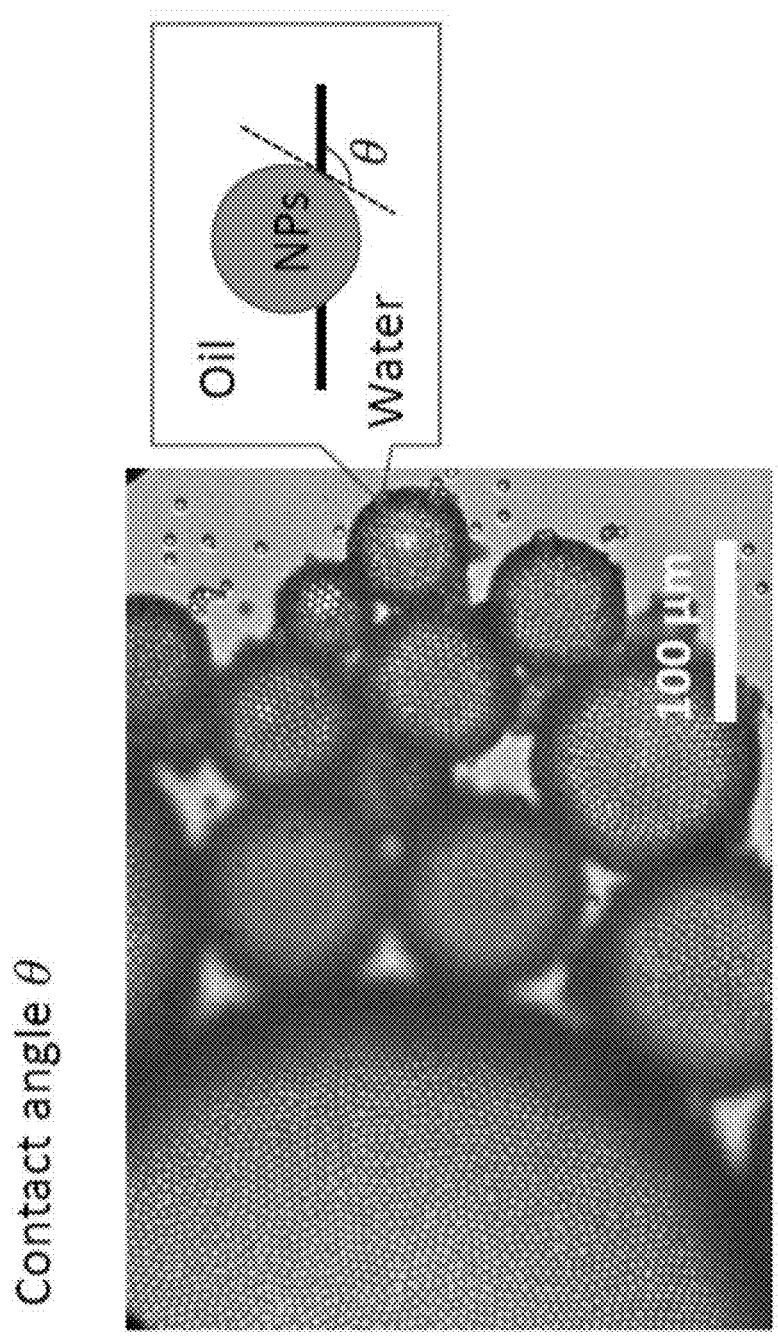
FIG. 17 shows the three phase contact angle θ of solid particles at the liquid-liquid interface, which is the angle between the tangents to the solid surface and the liquid-liquid interface measured through one of the liquids in each point of the three-phase contact line where the solid and two fluids meet.
Figure 18:
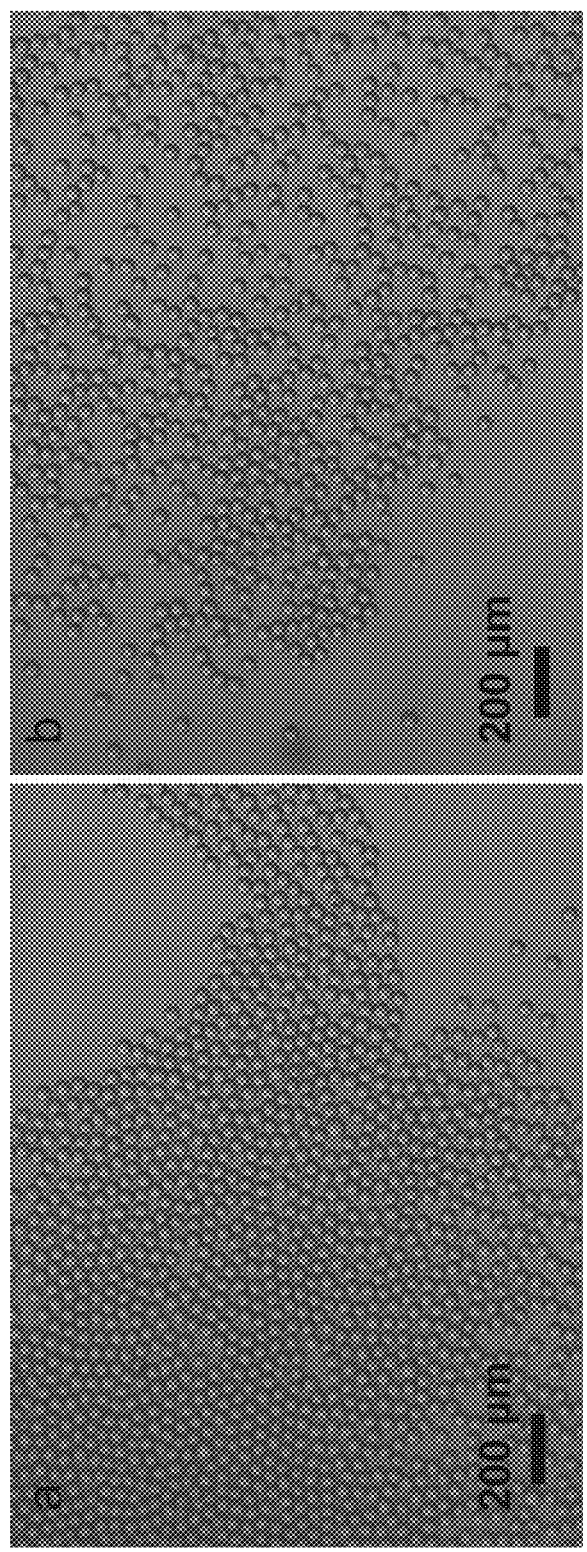
FIG. 18 shows optical images of NPs stabilized PCR buffer droplets stored in Eppendorf tube (a) before and (b) after heating at 95° C. for 20 min.

As expected, cells failed to adhere to an interface stabilized by EA-surfactant. In contrast, cells adhered to F—$SiO_2$ NPs-stabilized interface (FIG. 5). Importantly, it was observed that adherent cells spread and divided on F—$SiO_2$ NPs-stabilized interface (FIG. 6). Cells exert contractive forces on substrates. Cell adhesion and spreading typically requires solid surfaces that can sustain pushing and pulling by the cells. Fluid-fluid interfaces, including those stabilized by surfactants, cannot withstand such forces. Anchorage-dependent cells are generally not viable when suspended in a fluid. FIG. 6 confirm the presence of lamelopodia and filopodia in MCF-7 cells and 3T3 fibroblasts, suggesting that the nanoparticles have formed stable solid-like sheets that can withstand traction forces generated by cells. These sheets were stable for multiple days as spread-out cells multiplied and created extended colonies (FIGS. 6 and 16). While water-oil interfaces stabilized by hydrophobic particles can form a solid-like rigid substrate that could support the attachment of anchorage-dependent cells, provided here is the first concrete evidence that such interfaces could in fact allow the adhesion, spreading, and growth of canonical anchorage-dependent fibroblasts lines. For cancer cells MCF-7 which could switch between anchorage-dependent colonies or suspended spheroids (mammospheres), nanoparticle-stabilized interface promoted the formation of adherent colonies. On the other hand, only floating-colony phenotype was observed on nanoparticle-free interfaces (FIGS. 6 and 16). Due to the low rigidity of surfactant-stabilized interfaces, the majority of previous research that combined water-oil emulsion and cell culture mandated the use of non-adherent cell lines, or cells lines capable of aggregating into floating spheroid cultures. The rigid solid-like interfaces described herein thus open up new applications of nanoparticle-stabilized droplets for the culture of anchorage dependent cells.

In conclusion, described herein includes a method for the synthesis of amphiphilic silica nanoparticles for the generation of stable aqueous droplets in a range of fluorinated oils. The particles effectively prevented the leakage of resorufin, a model dye that can leak in surfactant-stabilized drops. It was also showed the particles were compatible with microfluidic flow-focusing devices. The presence of the particles did not affect the growth of E. coli compared with biocompatible EA-surfactant. Importantly, the particles were compatible with the growth and spreading of adherent mammalian cells, a capability not easily achievable in surfactant systems. These particles should complement surfactants in the stabilization of droplets and open up new applications in droplet microfluidics.

Fluorinated Pickering Emulsion with Non-Adsorbing Interfaces

Described here is the use of fluorinated Pickering emulsions with non-adsorbing interfaces in droplet-based protein assays such as enzymatic assays. Nanoparticle and microparticle surface can be rendered non-adsorbing to proteins (e.g., enzymes) by in-situ adsorption of hydrophilic polymers such as polyethylene glycol (PEG) on particle surfaces. Enzyme activities are preserved in droplets stabilized by PEG-adsorbed nanoparticles and microparticles, and are comparable with those in drops stabilized by PFPE-PEG surfactants. In addition, the non-adsorbing Pickering emulsions successfully prevent inter-drop molecular transport, thereby maintaining the accuracy of droplet assays. The particles can be synthesized according to economical and scalable procedures. The PEG adsorbed nanoparticles and microparticles described herein are thus a competitive alternative to the current surfactant-based system. Alternatively, particles covalently grafted with hydrophilic polymers can be dispersed into the continuous phase to stabilize enzyme activities in the dispersed phase.

Droplet Stability.

Figure 19:
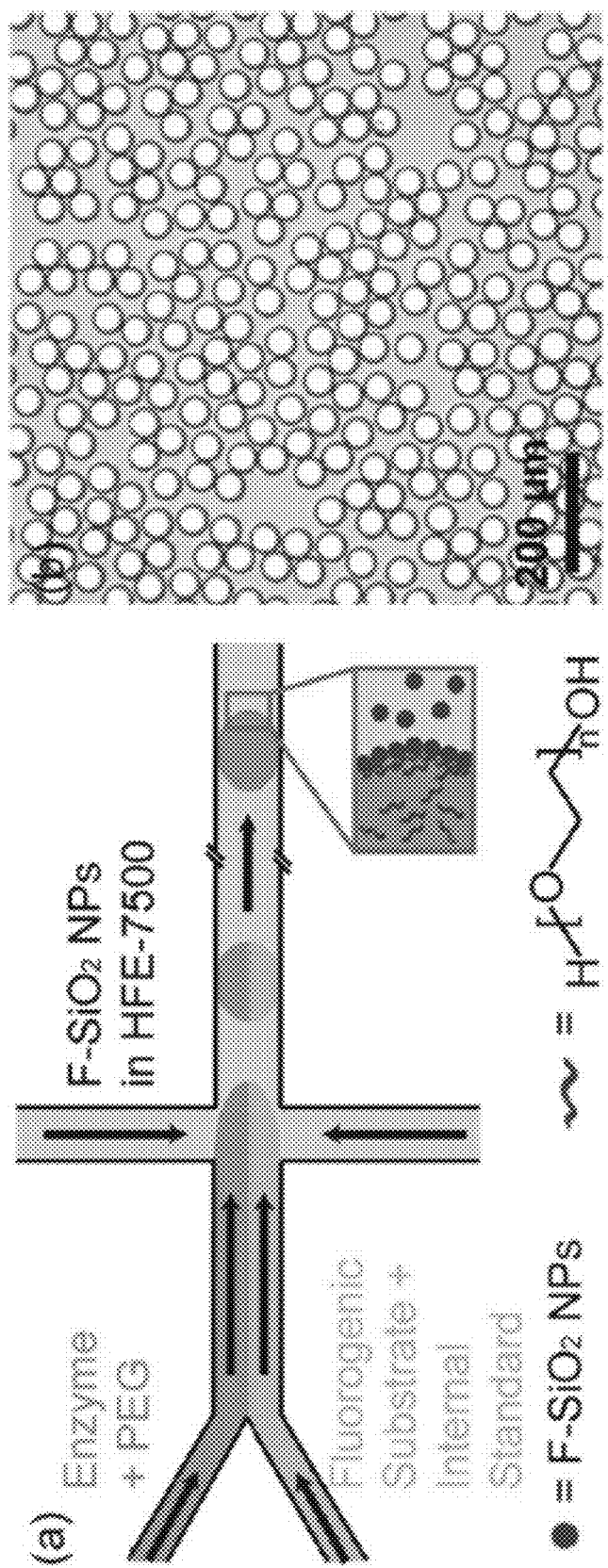
FIG. 19: (a) Scheme illustrating droplet generation and reagent encapsulation. (b) Optical image of drops stabilized by 100 nm $PEG_{ads}$-F—$SiO_2$NPs collected from the droplet generator.
Figure 23:
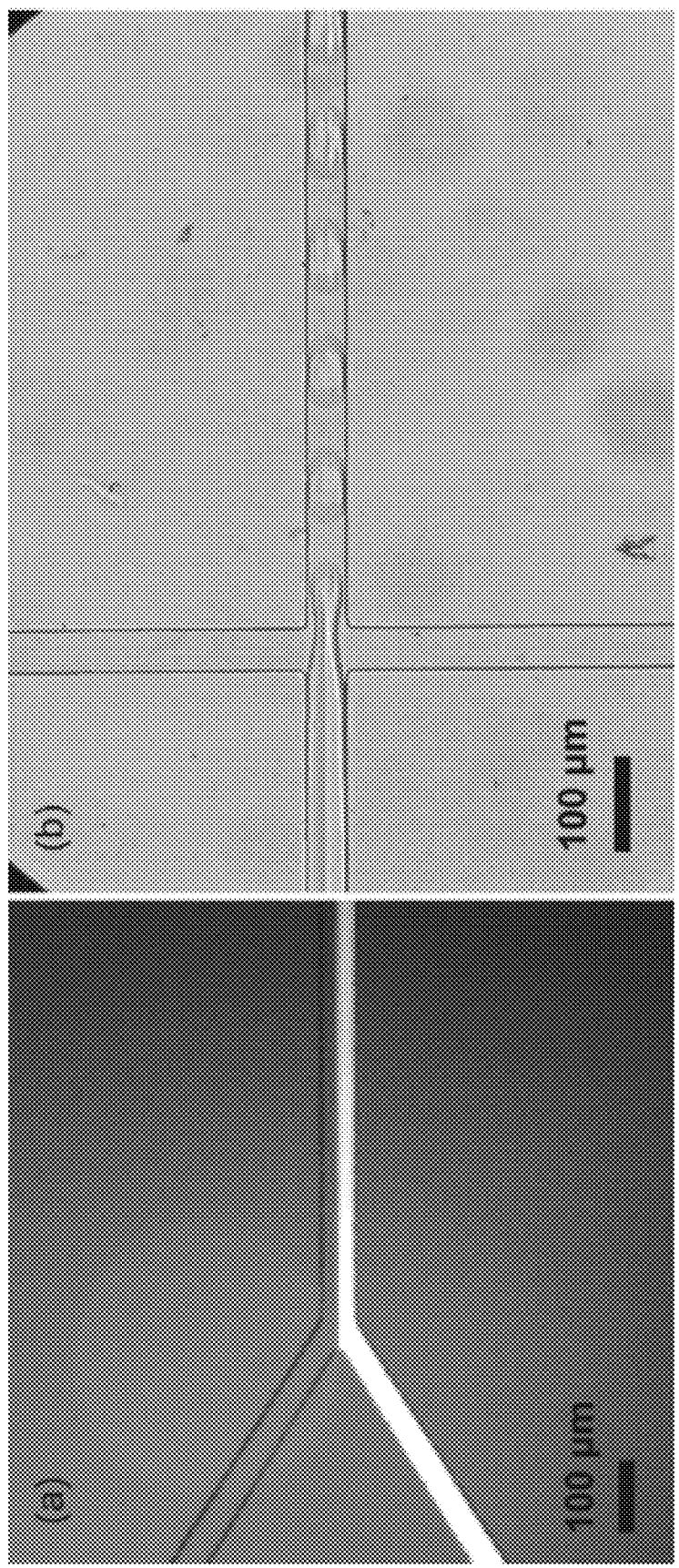
FIG. 23: (a) Fluorescence images showing laminar flow between the two streams of the dispersed phase upstream of the flow-focusing nozzle. The brighter stream (substrate stream) contains fluorescein diphosphate (FDP), which is weakly fluorescent compared with the background. The darker stream (enzyme stream) contains Bacteria Alkaline Phosphotase (BAP). The flow rate for each stream was at 0.1 mL/hr. The mixing ratio of the contents from the two streams inside the drops was 1:1. (b) Optical image showing the droplets generated at the flow-focusing nozzle.

Drops were generated using a flow-focusing nozzle with one inlet for the continuous phase and two inlets for the dispersed phase (FIG. 19). The continuous phase contained 1.5% (w/w) of 100-nm F—SiO2 NPs dispersed in fluorinated solvent HFE-7500. For the dispersed phase, one inlet was used for introducing an aqueous stream containing enzyme and PEG, and the other inlet was used for introducing an aqueous stream containing a fluorogenic substrate and an internal standard for subsequent fluorescence quantification. The two streams came into contact ~850 µm upstream of the flow-focusing nozzle. At the flow rates used, the contact time was approximately 18 milliseconds, ~105 times shorter than that needed for the completion of the enzymatic reactions used in this work (~1 hour). The contents of these two streams were thoroughly mixed after being selectively encapsulated into droplets (FIG. 23). This on-chip mixing ensured that the enzymatic reactions took place primarily within the droplet. The final concentration of PEG in the drops was fixed at 0.4% (w/v).

Figure 24:
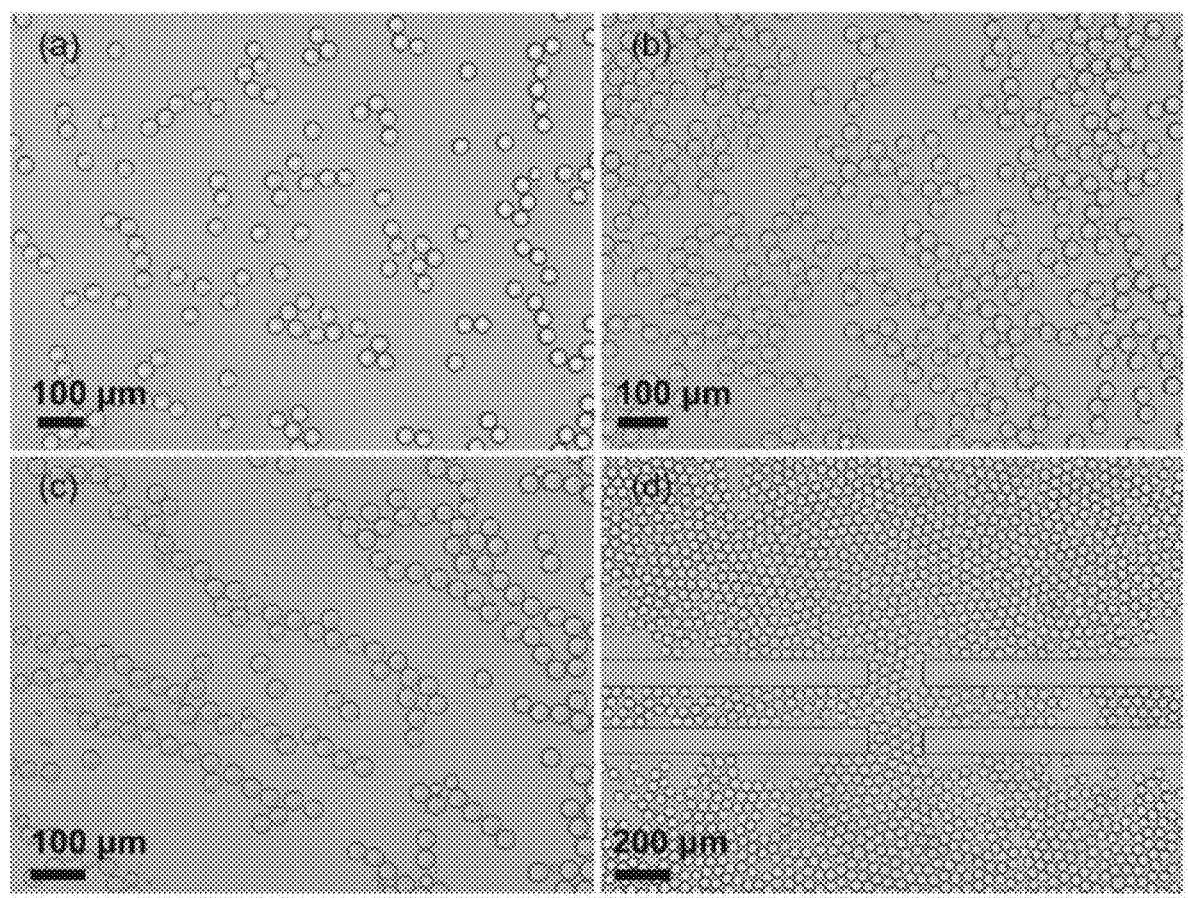
FIG. 24: Optical images of $PEG_{ads}$-F—$SiO_2$NPs stabilized droplets containing 4 mg/mL PEG (a) before and (b) after washing with FC-40 for three times; (c) after heating at 90° C. for 10 mins; (d) after reinjection into 55 μm-tall PDMS channel. The presence of PEG did not destabilize the drops. These drops showed mechanical and thermal stability against coalescence.

FIG. 19b shows that the drops formed were monodisperse and stable against coalescence. The presence of enzyme and PEG in the disperse phase did not destabilize the drops. They were stable against coalescence under typical droplet manipulation conditions, such as washing and dilution with another fluorinated solvent FC-40, reinjection into narrow channels, and heating at 90° C. for 10 minutes (FIG. 24). These droplets were highly stable because the nanoparticles and PEG were pre-dispersed in different phases before droplet generation, and they interacted after the formation of drops. The presence of PEG in the drops did not affect the amphiphilicity of the particles, as PEG could not interact with the portion of the particles exposed to the continuous phase. The concentration of PEG in the aqueous phase also did not affect the irreversible adsorption of F—SiO2 NPs to the water-oil interface.

PEG Adsorption onto Particle Surface.

Figure 20:
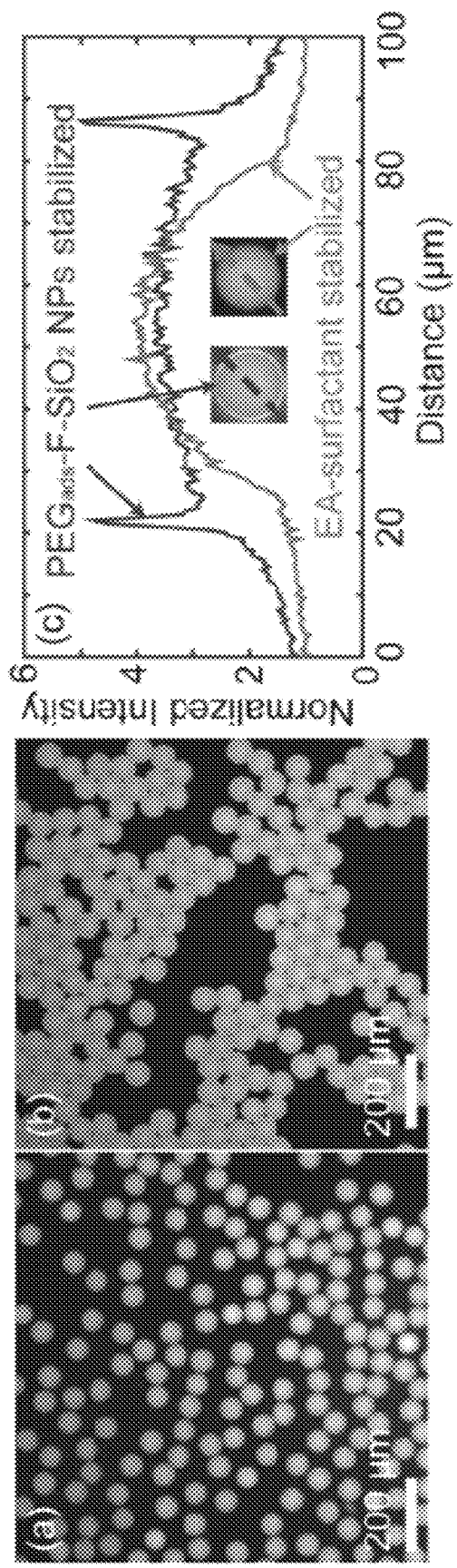
FIG. 20: Fluorescence image of aqueous drops containing fluorescein-linked PEG (MW=5000, 0.04 mg/mL) that are stabilized by (a) EA-surfactant and (b) 100 nm $PEG_{ads}$-F—$SiO_2$ NPs, respectively. Note the adsorbed PEG here is fluorescein-linked PEG. (c) Line scans of fluorescence intensity profile across the droplets shown in FIGS. 20a and 20b. The scan started and ended around 10-20 μm away from the droplet boundary. Fluorescence intensity was normalized to the background continuous phase. Arrows indicate the direction of the line scan along which brightness was measured using ImageJ.
Figure 25:
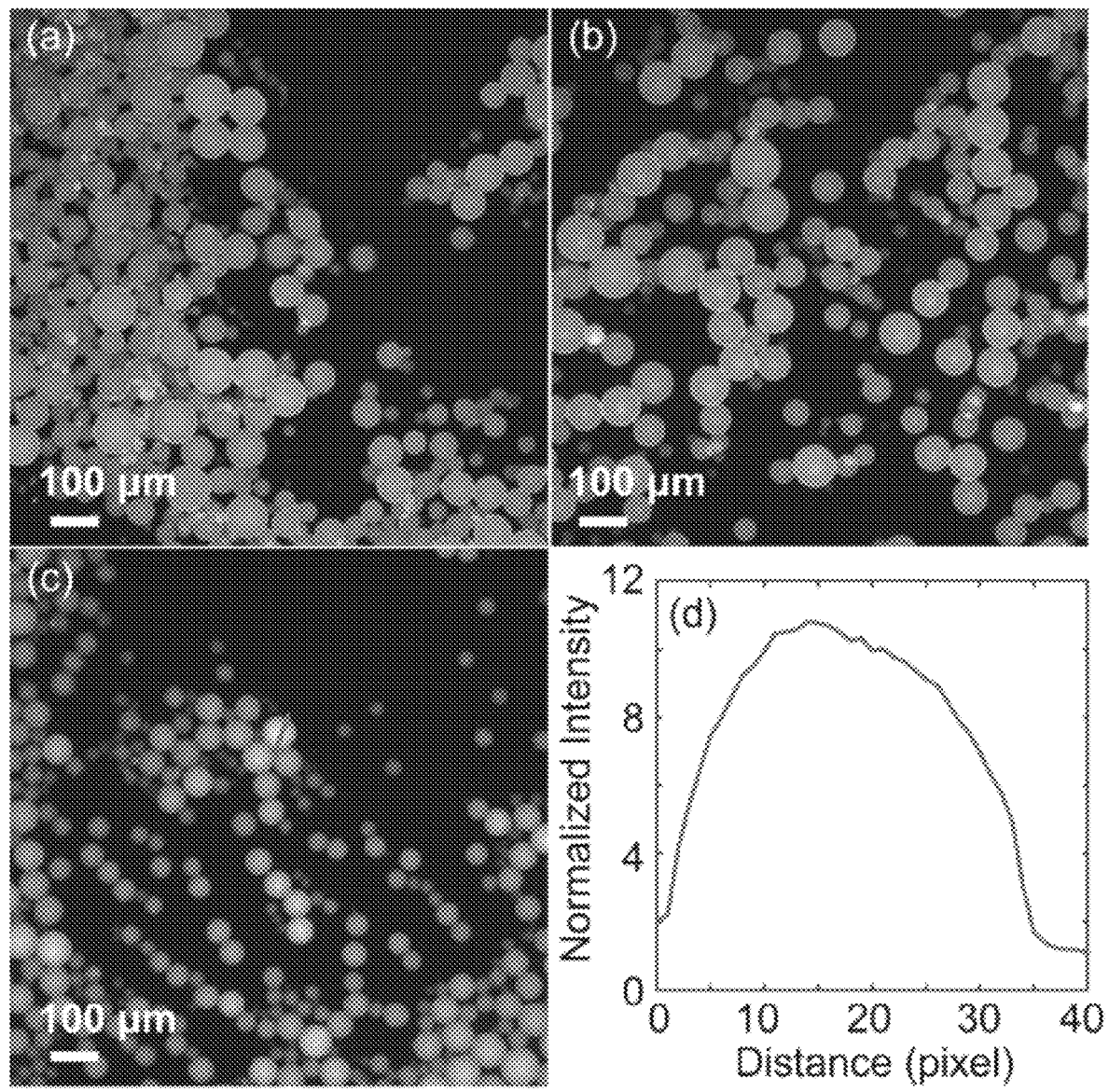
FIG. 25: (a-b) Fluorescence image of polydisperse aqueous drops stabilized by 100 nm $PEG_{ads}$-F—$SiO_2$ NPs, where dispersed phase contained (a) 0.04 mg/mL mPEG-fluorescein, (b) 0.04 mg/mL mPEG-fluorescein and 33.75 U/mL BAP, respectively. (c) Fluorescence image of polydisperse aqueous drops stabilized by F—$SiO_2$ NPs where dispersed phase contained 8 μM fluorescein. (d) Fluorescence intensity profile of a typical drop in (c). The scanning direction is indicated by the arrow. The formation of fluorescent rim was not dependent on the size of the droplet, nor the presence of enzyme. Fluorescein has no affinity to nanoparticle surface, and the nanoparticles did not increase scattering of light and thus no rim formation was observed.

To probe the adsorption of PEG onto particle surface, the spatial distribution of PEG within the droplets stabilized by F—SiO2 NPs and EA-surfactants respectively were measured (FIG. 20). Here, fluorescein-tagged PEG (mPEG-fluorescein, MW=5000) was used in the dispersed phase. Since fluorescein was covalently linked to PEG, the concentration of PEG at a given region can be estimated by measuring the fluorescence intensity distribution. When the droplets were stabilized by EA-surfactant, the fluorescence intensity was maximum in the center of the drops due to their spherical shape (FIG. 20c), suggesting that PEG molecules were uniformly distributed inside the drop. This distribution was expected as the head group of the EA-surfactant already contained PEG, which prevented further adsorption and concentration of PEG at droplet interface. When the drops were stabilized by F—SiO2 NPs, the fluorescence intensity was maximum at the droplet interface forming fluorescent rims. A line scan across the image of a drop shows two intensity peaks which were separated by a distance equal to the droplet diameter (~65 µm, FIG. 20c). Such intensity profile indicates that PEG molecules were concentrated at the droplet interface. It was not due to the increased scattering of light by the particles as a drop containing fluorescein only did not produce such fluorescent rims (FIG. 25c). The presence of enzymes did not affect the rim formation in nanoparticle-stabilized drops, even at high enzyme concentrations (~33.75 U/mL) (FIG. 25b). It indicates that the adsorbed PEG could not be displaced by enzyme molecules, as the PEG would be distributed uniformly within the droplet otherwise.

Since the molecular weight of the PEG (MW~5000-8000) was smaller than that of the enzymes used (MW~89000 for bacterial alkaline phosphatase and MW~44000 for horseradish peroxidase), the diffusion and adsorption of PEG onto nanoparticle surfaces should be faster than that of the enzymes. In addition, the adsorption of PEG can be driven by the formation of hydrogen bonds in the presence of polar groups such as silanol groups on surfaces. Formation of hydrogen bond between PEG chains and silanol groups occurred since the silica nanoparticles were partially fluorinated. Subsequent enzyme adsorption on particle surface is prevented due to steric repulsions between the PEG chains and enzymes. Such repulsions can predominate over attractive interactions between enzymes and nanoparticle surface.

Restoration of Enzymatic Activities.

To test if the presence of PEG would preserve enzymatic activity, two representative assays involving enzymes alkaline phosphatase and horseradish peroxidase respectively were investigated. In the first assay, Bacterial Alkaline Phosphatase (BAP) was used to catalyze the hydrolysis of fluorescein diphosphate (FDP) to produce a green fluorescent product fluorescein. Resorufin (0.01 mg/mL, 42.5 µM) was introduced to each drop as an internal standard to normalize the fluorescence intensity of fluorescein. Fluorescence intensity was normalized by calculating the fluorescence intensity ratio between fluorescein and resorufin. Due to the non-overlapping excitation/emission wavelengths between fluorescein (494 nm/521 nm) and resorufin (571 nm/585 nm), the presence of resorufin did not interfere with the fluorescence of fluorescein.

Figure 21:
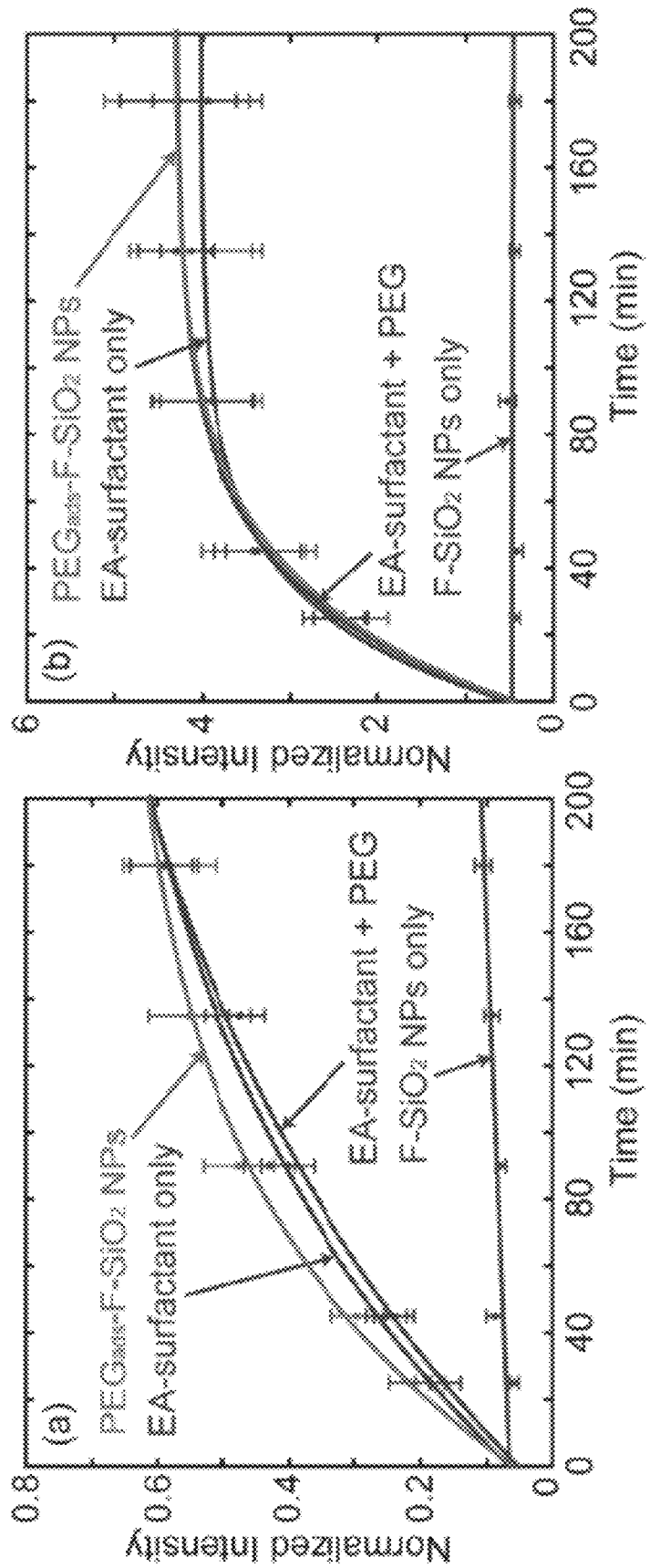
FIG. 21: Fluorescence intensity evolution of two representative enzymatic assays. (a) Hydrolysis of fluorescein diphosphate (FDP, 20 μM) in the presence of bacteria alkaline phosphatase (BAP, 9.375 U/mL), and (b) oxidation of Amplex Red (50 μM) by excess hydrogen peroxide (1 mM) catalyzed by horseradish peroxidase (HRP, 5 mU/mL). The lines are guides to the eye. The intensity values were normalized to an internal standard.
Figure 26:
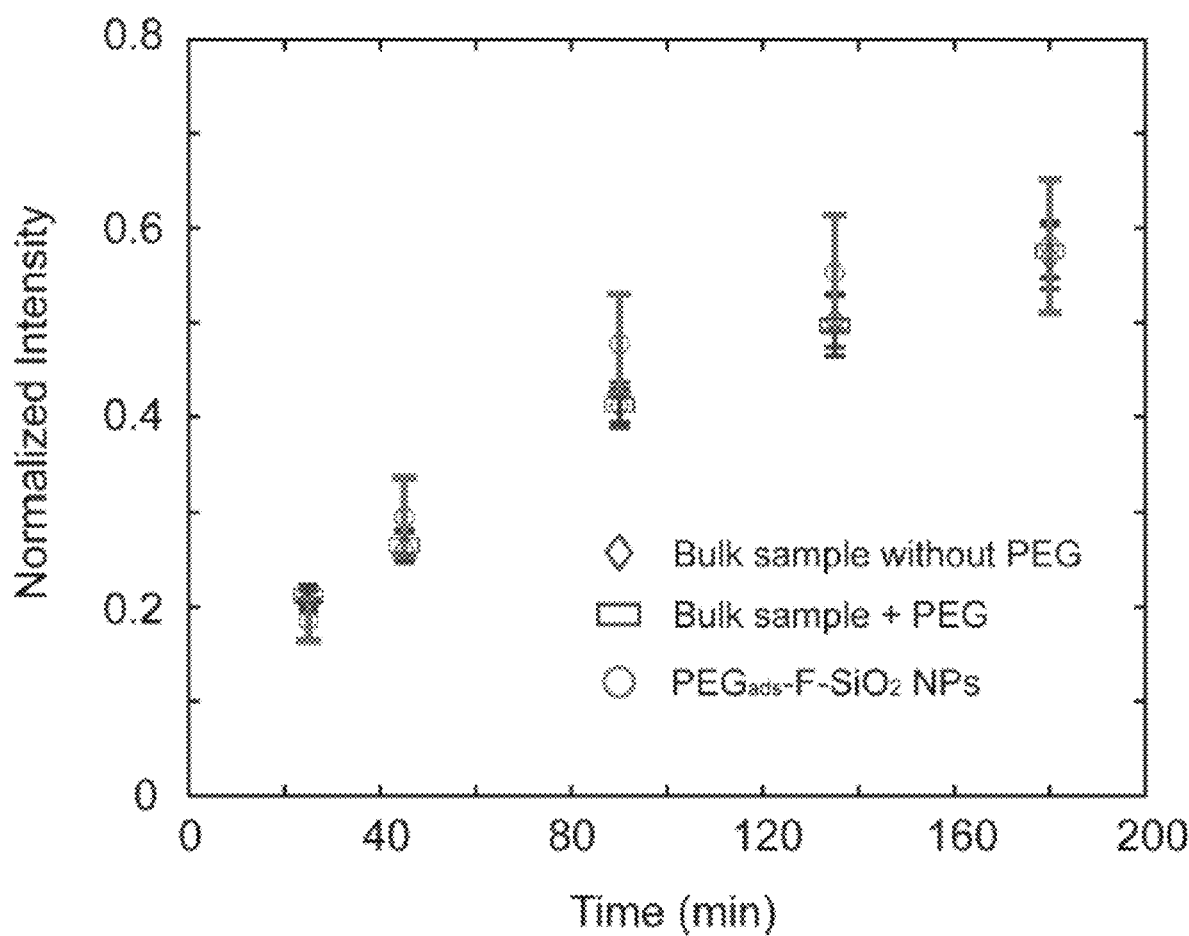
FIG. 26: Fluorescence intensity evolution of bulk FDP/BAP assays performed in a 96-well plate (diamonds: bulk sample without PEG; rectangles: bulk sample with 4 mg/mL PEG). The reaction condition is the same as the one shown in FIG. 21a. 20 μL of the reaction mixture was extracted at every time point and injected into a microchannel with the same height as all other microchannels used in droplet experiments to ensure the same path length in the measurement of fluorescence intensities using an epifluorescence microscope. The same normalization method was used as in droplet experiments. For comparison, the plot for droplet assay stabilized by PEGads-F—SiO2 NPs is also included below (circles).

FIG. 21a shows the time evolution of fluorescence signal for fluorescein from F—SiO2 NPs-stabilized droplets with or without PEG. In the absence of PEG, the fluorescence intensity of fluorescein did not increase over time, indicating the possible deactivation of BAP. The addition of PEG into F—SiO2 NPs-stabilized drops greatly enhanced the fluorescence turn-on rate, which was comparable with the rates in drops stabilized by EA-surfactant and in bulk assays performed in a 96-well-plate (FIG. 26). The addition of PEG did not have significant effect on the reaction rate in both surfactant-stabilized drops and in bulk samples (FIG. 26). Similar results were observed for horseradish peroxidase (HRP) where Amplex Red reagent ((10-acetyl-3,7-dihydroxyphenoxazine) was oxidized to resorufin in the presence of hydrogen peroxide and HRP (FIG. 21b). 10 µM fluorescein was used as an internal standard here. Although HRP was generally believed to be an efficient enzyme, its activity in F—SiO2 NPs-stabilized droplets was lost in the absence of PEG. The addition of PEG in F—SiO2 NPs-stabilized droplets was effective in restoring enzyme activity to a level comparable with state-of-the-art EA-surfactant systems. These results are consistent with the observation that coating solid surfaces with PEG prevents undesirable non-specific adsorption of proteins and subsequent degradation of their structures and/or functions.

Covalent Grafting and Chemisorption of PEG.

To coat the nanoparticles with PEG, there are two options: 1) covalent grafting of PEG onto nanoparticles prior to droplet generation, followed by the dispersion of these particles into the continuous phase, and 2) chemisorption of free PEG molecules from the dispersed phase onto F—SiO2 NPs originally dispersed in the continuous phase after droplet formation.

Figure 27:
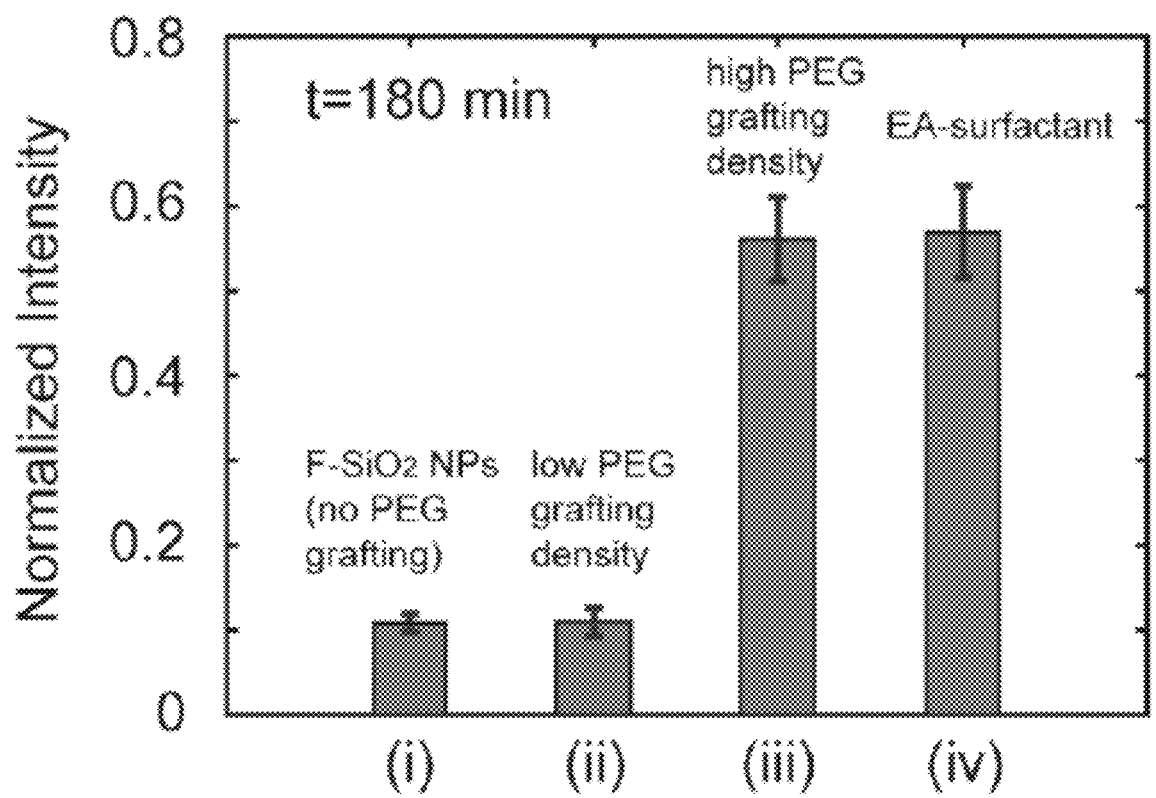
FIG. 27: Bar chart showing the mean values of normalized fluorescence intensity of FDP/BAP droplet assays after 3 hour of incubation. The mean was calculated from ~600 drops for each sample. The height of the error bars represents two standard deviations from the mean. In (i), the droplets were stabilized by F—SiO2 NPs without PEG coating. In (ii)-(iii), the droplets were stabilized by PEGcovalent-F—SiO2 NPs with different surface PEG grafting densities. PEG density was controlled by varying the concentration of m-PEG silane during synthesis, where (ii) [PEGylated silane]=0.237 mg/mL and (iii) [PEGylated silane]=1.85 mg/mL. High [PEGylated silane] yielded particles that restored BAP activity. In (iv), the droplets were stabilized by EA-surfactants.

In the first approach, dispersion of particles in the continuous phase can avoid undesirable interactions between particles and droplet contents. PEG chains were grafted on the surface of F—SiO2 NPs with different coating densities by the hydrolysis of PEG linked silane (mPEG-silane). The PEG density at the interface was adjusted by varying the concentration of precursor mPEG-silane in the synthesis of the F—SiO2 NPs. These PEGylated particles (referred to as "$PEG_{covalent}$-F—$SiO_2$ NPs") were used as droplet stabilizer to test BAP activity inside the drops (FIG. 27). Fluorescence measurement indicated that BAP activity was preserved when high concentrations of precursor mPEG-silane were used, which corresponded to a high PEG graft density on particle surfaces (FIG. 27(iii)).

Figure 28:
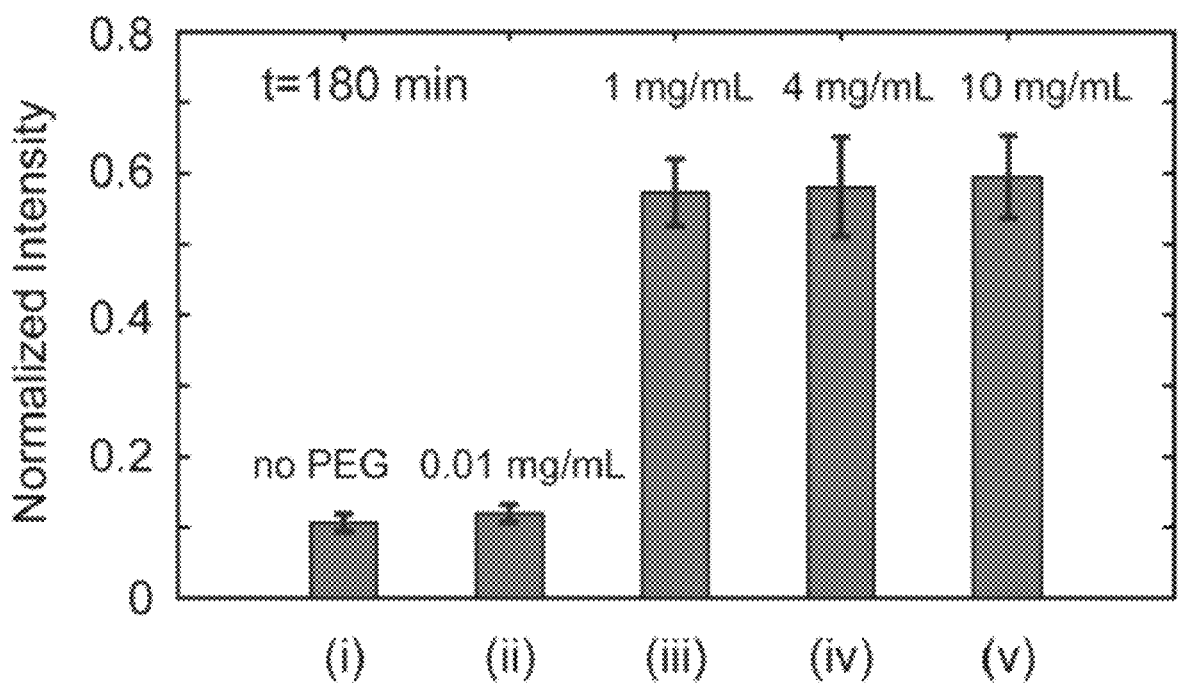
FIG. 28: Bar Chart showing the mean values of normalized fluorescence intensity of FDP/BAP droplet assays after 3 hour of incubation. The mean was calculated from ~600 drops for each sample. The height of the error bars represents two standard deviations from the mean. In (i), the droplets were stabilized by F—SiO2 NPs, and in (ii)-(v), the droplets were stabilized by PEGads-F—SiO2 NPs with different [PEG] in the dispersed phase (from 0.01 mg/mL to 10 mg/mL). [PEG] for each sample is specified in the figure.

In the second approach, PEG is introduced separately into the dispersed phase, while F—$SiO_2$ NPs are used in the continuous phase. The PEG coating/adsorption process took place after the particles adsorbed at the water-oil interface (to form "$PEG_{ads}$-F—$SiO_2$ NPs"). The PEG density at the interface was controlled independently by varying the concentration of PEG in the dispersed phase. The high solubility of PEG in aqueous solutions ensured sufficient coating density on particle surface to preserve enzyme activity. It was found that enzymatic activity was fully restored when sufficient amount of PEG (e.g., >~1 mg/mL) was present in the droplets; increasing PEG concentration beyond this value did not affect the reaction rate (FIG. 28). This result is consistent with the covalent coating of PEG on solid substrates, which specify the density of PEG chains to exceed a certain "threshold value" to retrieve full enzyme activity. Since PEG interacted with particles after droplet formation, this approach did not decrease the dispersibility of the particles in the continuous phase, nor the formation and the stability of the droplets.

Leakage Prevention for the Accurate Interrogation of Enzymatic Activities.

Figure 29:
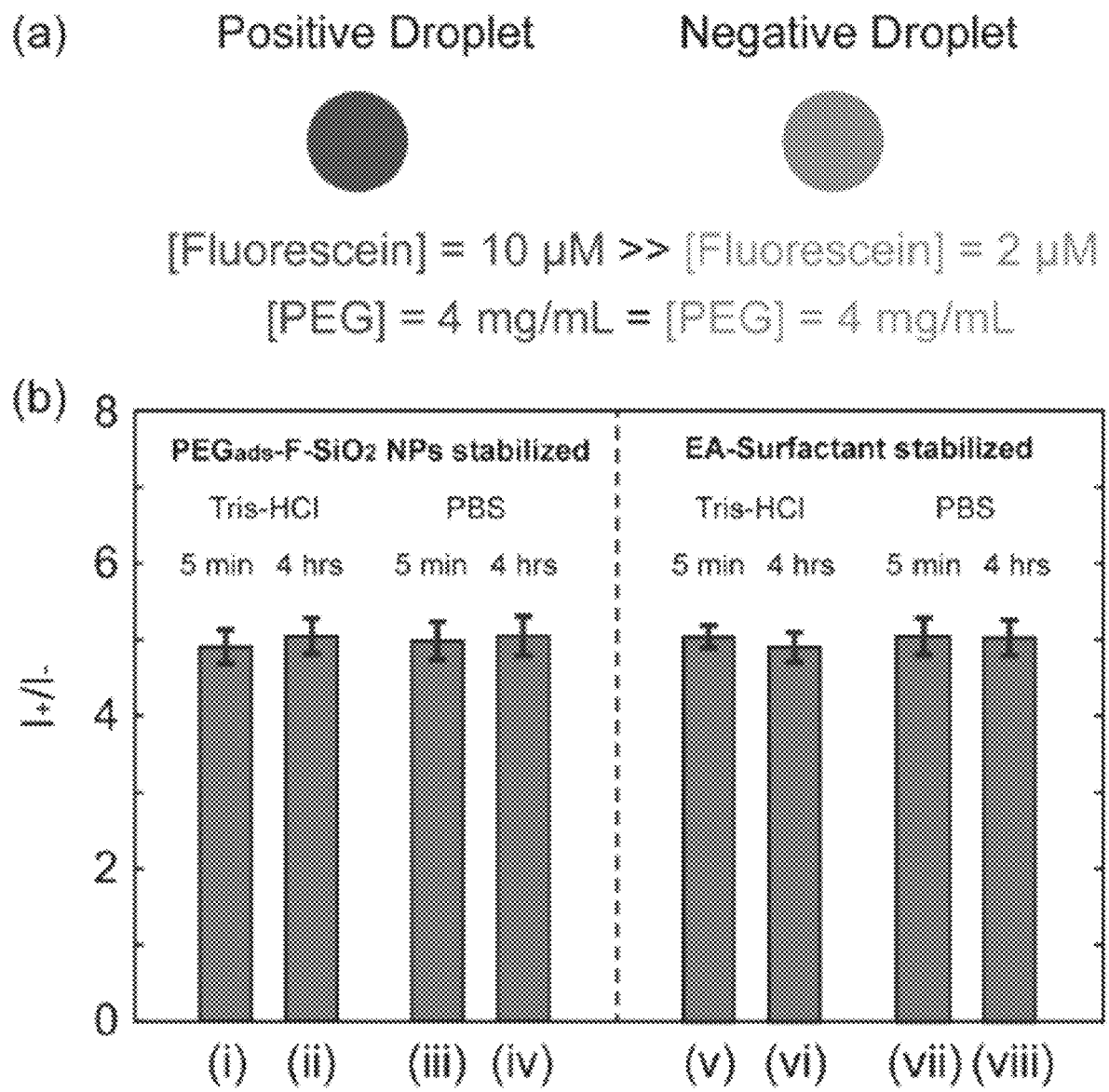
FIG. 29: Experimental verification that fluorescein does not leak and can be used as internal standard for leakage experiments. (a) Scheme showing the composition of positive and negative droplets. (b) Bar charts showing the mean values of fluorescence intensity ratio (I+/I−) between positive and negative droplets after 5 min and 4 hrs of incubation respectively. The droplet stabilizer (either PEGads-F—SiO2 NPs or EA-surfactant) and buffer used (either 50 mM Tris-HCl or 1×PBS) are specified in the figure. The mean was calculated from ~500 drops for each sample. The height of the error bars represents two standard deviations from the mean. The original droplet mixture contained positive and negative droplets at approximately 1:1 ratio. After 4 hours of incubation, the resulting droplet mixture still contained 1:1 mixture of bright droplets (from positive droplets) and dark droplets (from negative droplets). I+ and I− are defined as the mean fluorescence intensity of bright droplets and dark droplets, respectively. I+/I− was maintained at 5 throughout the whole incubation period (up to 4 hours), which is consistent with the molar ratio of fluorescein between the positive and negative droplets at t=0. These results indicate that fluorescein did not leak.
Figure 30:
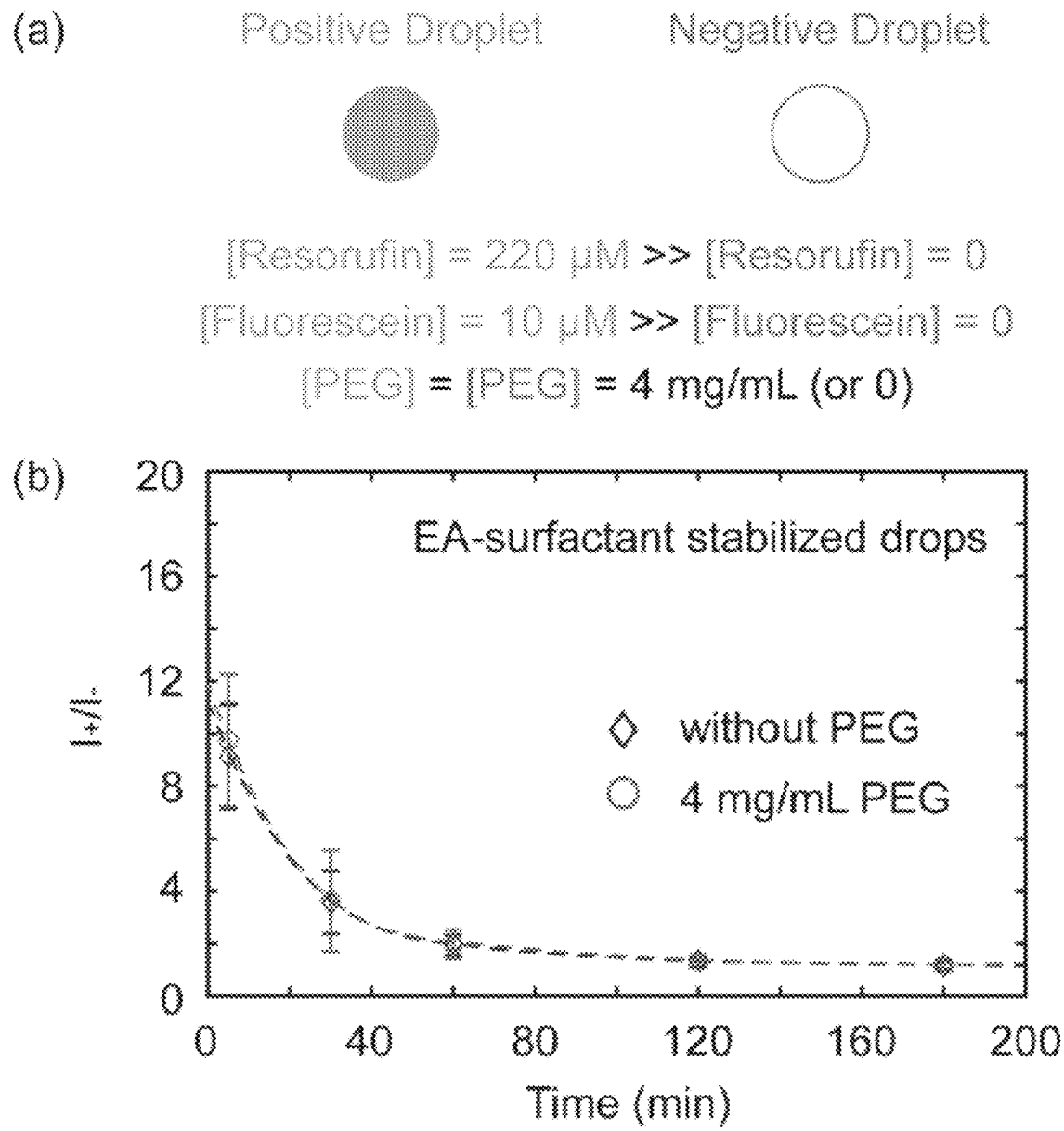
FIG. 30: Experimental verification that addition of PEG does not affect the leakage rate of a leaky fluorophore (resorufin). (a) Scheme showing the composition of positive and negative droplets. Fluorescein is used as a label for positive drops. (b) Plot showing the time evolution of resorufin fluorescence intensity ratio (I+/I−) between positive and negative droplets (diamonds: droplets without PEG; circles: droplets with 4 mg/mL PEG). The droplets were stabilized by EA-surfactant. The mean was calculated from ~500 drops for each sample at each time point. The height of the error bars represents two standard deviations from the mean. At t=120 min and 180 min, the height of the error bars is smaller than that of the markers. The lines are guides to the eye. The original droplet mixture contained positive and negative droplets at approximately 1:1 ratio. In both cases, fluorescence intensity ratio (I+/I−) decreased rapidly and reached 1 (i.e., complete homogenization of fluorescence signals) in about 3 hours. The overlap of the two curves indicates that the presence of PEG in the dispersed phase does not affect the leakage rate of resorufin.

In many assays such as the directed evolution of enzymes, a fraction of the drops would contain enzymes with desired levels of activities. In order to quantify the variation in enzymatic activities from drop to drop accurately, it is important that the contents of the drops—including the fluorophores used in fluorogenic substrates—do not leak and cause cross-contamination. To show that the drops described herein did not leak, a model system was constructed with Amplex Red assay, where two populations of droplets with different enzymatic reaction rates were mixed. The different reaction rates were achieved by using different enzyme concentrations ([HRP]=0.1 mU/mL and 5 mU/mL, respectively) in the two populations of drops, while the substrate concentration was fixed ([Amplex Red reagent]=75 µM, [H2O2]=1 mM). The population of drops with high HRP concentration ([HRP]=5 mU/mL) was also labelled with fluorescein at a high concentration ([fluorescein]=10 µM). The population with low HRP concentration ([HRP]=0.1 mU/mL) was labelled with fluorescein at a low concentration ([fluorescein]=2 µM). Fluorescein was chosen to label the droplets since it is non-leaky even in drops stabilized by EA-surfactants (FIG. 29). Drops that contained high concentrations of HRP and fluorescein were referred to as "positive drops". Drops that contained low concentrations of HRP and fluorescein were referred to as "negative drops."

Figure 22:
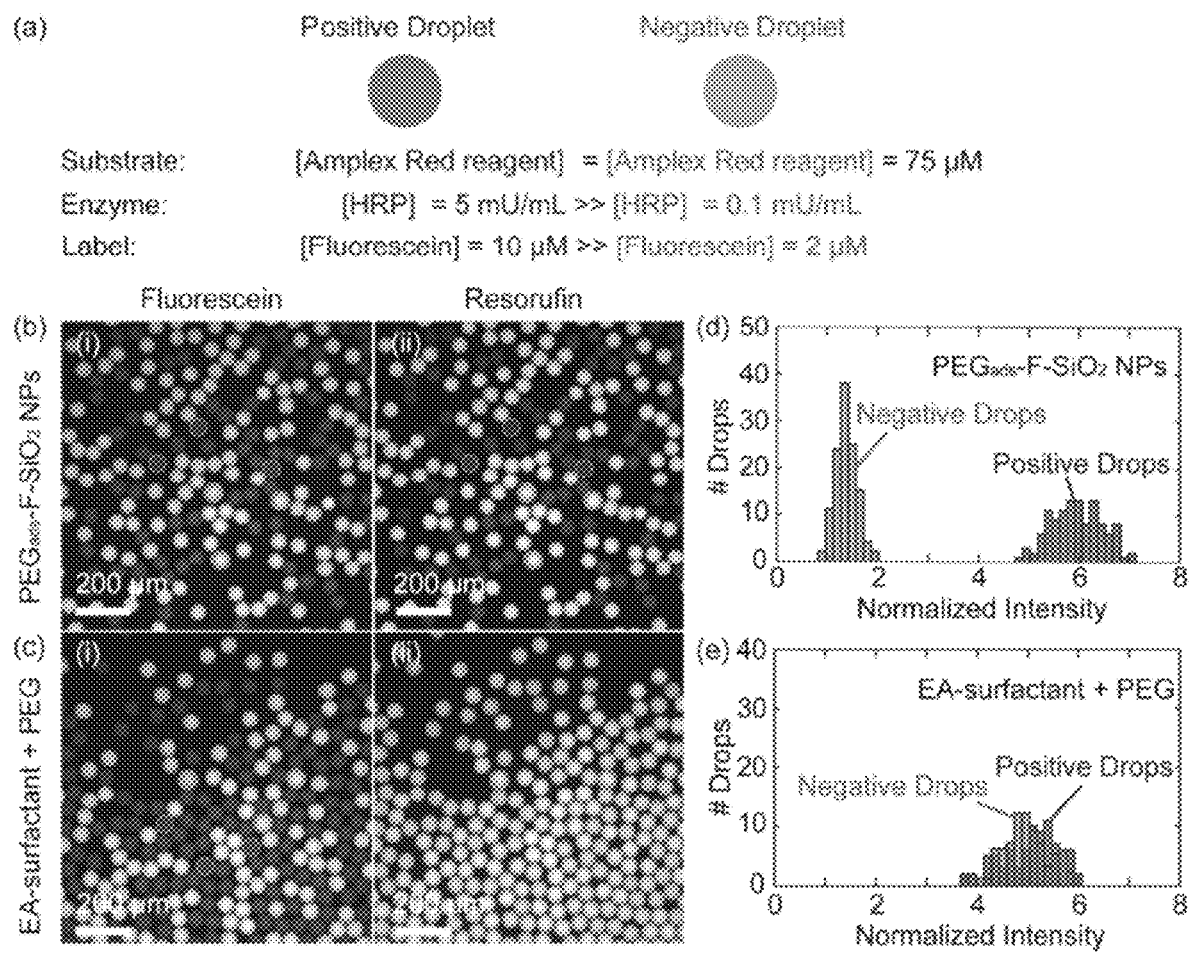
FIG. 22: (a) Scheme showing the composition of positive and negative droplets. (b-c) Fluorescence images of the droplet mixture containing different [HRP] after 4 hours of incubation, where droplets were stabilized by (b) 100 nm $PEG_{ads}$-F—$SiO_2$ and (c) EA-surfactants, respectively. All droplets contained 4 mg/mL PEG, 75 μM Amplex Red reagent, and fluorescein as a label for positive and negative drops at t=0. A few representative positive and negative drops are marked with circles. (d-e) Histograms showing resorufin fluorescence intensity distributions of the droplet mixture after 4 hours of incubation. The intensity values were normalized to an internal standard (fluorescein at 10 μM in positive drops).

FIG. 22 shows the results for the assay performed in drops stabilized by $PEG_{ads}$-F—$SiO_2$ NPs and EA-surfactants respectively. After 4 hours of incubation, the $PEG_{ads}$-F—$SiO_2$NPs system produced two populations of droplets with distinct fluorescence intensities. The positive drops had stronger fluorescence signal than the negative drops. This result was consistent with the fact that the reaction rate was faster in drops containing high [HRP] than in drops containing low [HRP]. The concentration and intensity from the reaction product resorufin were both higher in these drops than in drops with low [HRP]. In contrast, in the surfactant system, the fluorescence signal was homogenized due to the leakage of resorufin from positive drops to negative drops. It was difficult to distinguish positive drops from negative drops based on resorufin fluorescence signal. The total fluorescence count of resorufin in the surfactant system was higher than that in the particle system. This fact indicates the leakage of Amplex Red substrate from negative drops to positive drops. At t=0, no leakage of the substrate was expected due to the constant initial substrate concentration among all droplets. After some incubation, however, the substrate molecules were consumed faster in positive drops than in negative drops leading to a substrate concentration gradient. Excess substrate molecules remaining in negative drops diffused into positive drops. They became oxidized to form resorufin and generated additional fluorescence signal.

Advantages Compared to State-of the-Art Droplet Stabilizers.

Table 2 summarizes the advantages of some embodiments of the invention described herein compared with other state-of-the-art droplet stabilizers: 1) The particles described herein are economical to synthesize and characterize. They do not require extra synthesis and purification steps to graft PEG onto particles. 2) They are effective in preserving enzyme activity. 3) They are effective in preventing the leakage of small molecules. Embodiments of the invention described herein demonstrate the ability to prevent both enzyme deactivation and molecular leakage. Combined with the biocompatibility with the attachment and growth of anchorage-dependent cells, the particles described herein fulfill criteria needed for the success of droplet assays. The Pickering system presented here offers a straightforward, flexible and economical platform for enzymatic studies in droplets, as well as new opportunities for a large range of biochemical assays.

TABLE 2

| | Simplicity of synthesis | Estimated Cost ($/mL)[a] | Enzyme activity | Accuracy (no leakage) |
|---|---|---|---|---|
| EA-surfactant | Complicated | ~$18 | High | Low |
| Electrostatically modified surfactant | Scalable | ~$0.16 | High | Low[b] |
| F—$SiO_2$NPs | Scalable | ~$0.9 | Low | High |
| $PEG_{ads}$-F—$SiO_2$ NPs (this work) | Scalable | ~$0.9 | High | High |

Figure 31:
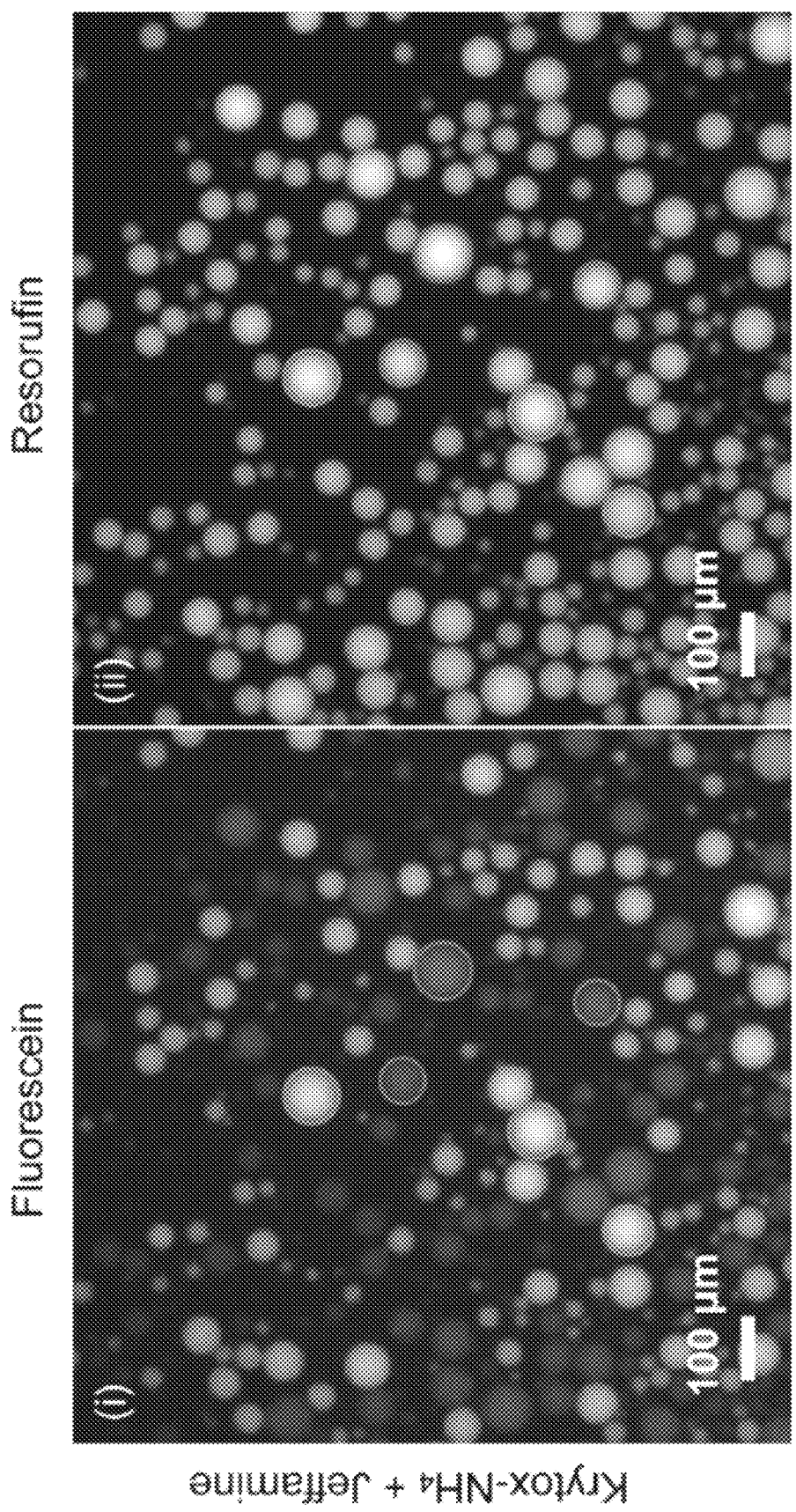
FIG. 31: Fluorescence images of a mixture of polydisperse droplets containing different [HRP] after 4 hours of incubation, where droplets were stabilized by 2% Krytox-NH$_4$. The drops were produced by vortexing a mixture of the disperse phase and the continuous phases. All droplets contained 75 μM Amplex Red reagent and 1.0% (w/v) Jeffamine ED-2001 at t=0. Droplets with high [HRP] (5 mU/mL) was defined as positive drops and labelled with 10 μM fluorescein. Droplets with low [HRP] (0.1 mU/mL) were defined as negative drops and labelled with 2 μM fluorescein. A few representative positive and negative droplets are marked with circles. Fluorescence intensity was completely homogenized after 4 hours of incubation indicating leakage of Amplex Red products.
Figure 32:
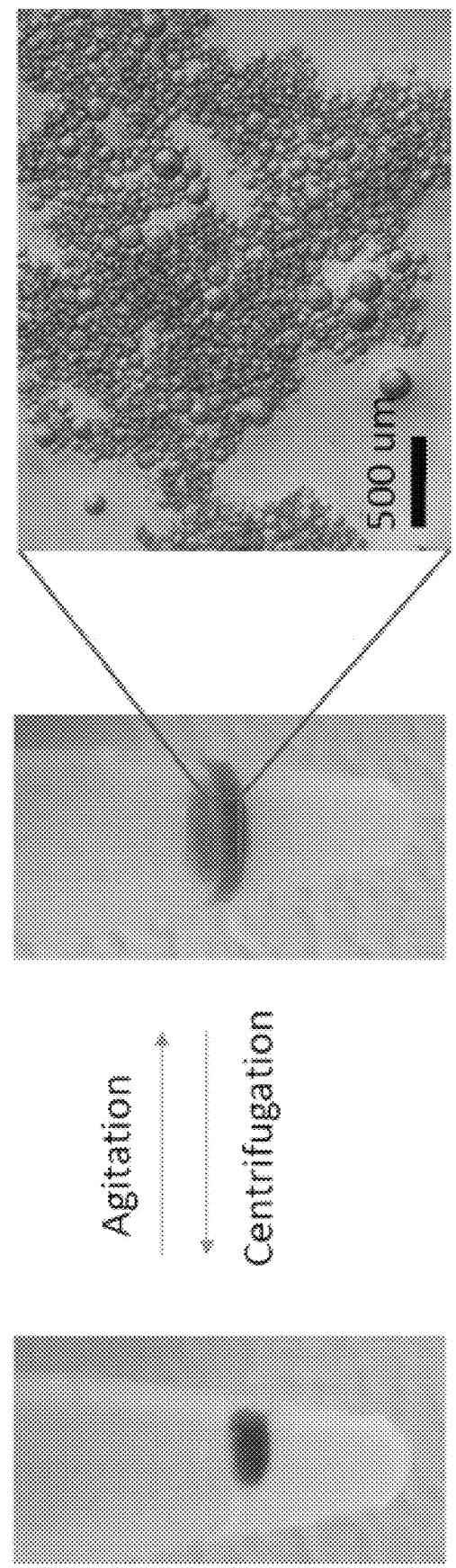
FIG. 32: Recycling of NPs for repeated emulsification. First, 20 μL of 1 mg/mL aqueous resorufin solution was added to 150 μL of 1% F—SiO$_2$ NPs in HFE-7500. Emulsion was produced by shaking Droplets were destabilized by centrifugation at 13,000 rpm for 15 min. After centrifugation, the NPs precipitates were re-dispersed in HFE-7500 by sonication. The emulsification process was repeated by shaking the mixture, which contained the re-dispersed F—SiO$_2$ NPs dispersion and the destabilized resorufin drop. Repeated emulsification was successful for up to three cycles. The recycling process can be further optimized by fine-tuning the NPs size and/or the spin rate and time.

[a]denotes cost (in USD) per mL of 2% (w/w) surfactant solution or nanoparticle suspension in HFE-7500.
[b]see FIG. 31.

WORKING EXAMPLES

Example 1.1

Two-Step Synthesis of Fluorinated Silica Nanoparticles (F—$SiO_2$ NPs)

3.57 mL of tetraethyl orthosilicate (TEOS) was added to a solution containing 50 mL of ethanol (EtOH), 1 mL of deionized water and 1.43 mL of $NH_4OH$ (28 wt. %). The reaction mixture was then stirred vigorously at room temperature for 12 hours to yield pristine $SiO_2$ NPs with a diameter of about 60 nm. 250 µL of 1H, 1H, 2H, 2H-perfluorooctyltriethoxysilane (FAS) was added directly to every 5.25 mL of the synthesized $SiO_2$ NPs solution obtained above, followed by vigorous stirring at room temperature for 60 min. To terminate the reaction, 22 mL of EtOH was added to dilute the reacting solution, and the particles were washed by centrifugation at 10,000 rpm for 20 min. After 3 cycles of washing, the supernatant was removed and the resulting particles were desiccated overnight. The mass of the solid was weighed and the solid was then re-dispersed in fluorinated solvent (HFE7500™ (3M), FC-40 or perfluoromethyldecalin). After fluorination, the resulting particles were dispersible in fluorinated oil. Syringe filter (polytetrafluoroethylene (PTFE) membrane, pore size 450 nm, VWR) were used to remove the dust and aggregates present in the suspension.

In a pilot scale-up test, up to 3 grams of F—$SiO_2$ NPs were synthesized in a single batch. 10 mL of 1H, 1H, 2H, 2H-perfluorooctyltriethoxysilane (FAS) was added directly to 100 mL of the synthesized SiO2 NPs solution obtained above, followed by vigorous stirring at room temperature for 40 min. To terminate the reaction, every 10 mL of the reaction mixture was diluted with 40 mL EtOH, centrifuged at 5000 rpm (~4700×g, Sorvall LEGEND X1R). After 3 cycles of washing, the supernatant was removed and the resulting particles were desiccated overnight. The scales can be further increased to at least tens of grams per synthesis.

Example 1.2

Fluorination of Commercially Available Silica Particles

Silica nano- or micro-particles from Bangs Lab were concentrated from the original aqueous suspension by centrifugation at 1000 rpm. After removing the supernatant, 5.36 mL of EtOH and 153.6 µL of $NH_4OH$ were added to 10 µL of the concentrated particle suspension. Appropriate amount of FAS was added under vigorous stirring (see Table 3 for details). After 40 min of reaction, the particles were isolated by centrifugation at 1000 rpm. Such particles were highly dispersible in fluorinated solvents and concentrations of 5% (w/w) in HFE-7500 can be obtained.

TABLE 3

For each experiment, 400 µL of silica particles suspension was centrifuged at 1000 rpm for 5 min. The supernatant was discarded and the particles were concentrated to a volume of approximately 10 µL. This concentrated particle suspension was then redispersed to a solution containing 5.36 mL EtOH and 153.6 µL $NH_4OH$. After that, various volumes of neat 1H-1H-2H-2H perfluorooctyl triethoxysilane (FAS) were added to the above solution mixture under vigorous stirring at room temperature. All the fluorinated particles were isolated at 40 min.

| Type of pristine silica spheres | wt. % in original suspension | Volume of neat FAS added (µL) |
|---|---|---|
| 150 nm silica nanosphere | 9.8 | 800 |
| 780 nm silica nanosphere | 10.0 | 600 |
| 1.01 µm silica microsphere | 9.95 | 450 |
| 2.01 µm silica microsphere | 9.8 | 120 |
| 5.2 µm silica microsphere | 10.09 | 40 |

Example 1.3

E. coli Cell Culture

K12 E. coli and E. coli expressing Green Fluorescent Protein (GFP) (abbreviated as "GFP E. coli") were obtained from the laboratory of Jianghong Rao at the Department of Radiology, School of Medicine, Stanford University. Liquid cultures of E. Coli were grown by picking a colony from the agar plate, and dipping into a growth media which contained autoclaved LB Broth with 20 µg/mL of tetracycline (for K12 E. coli) or 50 µg/mL of kanamycin and 0.1 mM Isopropyl β-D-1-thiogalactopyranoside (IPTG) (for GFP E. coli). To measure the growth rate of K12 E. Coli inside droplets stabilized by F—$SiO_2$ NPs, emulsions of E. coli culture were formed by vortex-mixing 1 mL of the liquid culture ($10^5$ cells/mL) with 6 mL of HFE-7500 containing either F—$SiO_2$ NPs or biocompatible EA surfactant (Raindance Technologies). The polydispersity of the drops here did not affect the measurements of cell growth. The resulting emulsions were incubated in a shaker-incubator at 37° C. and at 250 rpm. At different time points, 20 µL, of the emulsions were extracted and destabilized to measure cell concentrations. The concentration of cells was measured using Thermo Scientific NanoDrop™ 1000 Spectrophotometer, which reports the optical density at 600 nm. The optical densities to cell concentration for E. coli have been calibrated by other groups.

Example 1.4

Resorufin Leakage Test

Positive and negative drops were generated from flow-focusing device with serpentine channel separately. The continuous phase contained 4% (w/w) 780 nm F—$SiO2$ NPs in HFE-7500. Positive drops contained 220 µM resorufin and 10 µM fluorescein in 1×PBS, and negative drops contained 1×PBS. The drops were collected separately in two Eppendorf tubes. For F—$SiO_2$ NPs-stabilized drops, the un-adsorbed NPs in continuous phase was removed by washing with FC-40 three times before the positive and negative drops were mixed at 1:1 ratio. EA-surfactant stabilized positive and negative drops were mixed at 1:1 ratio. The mixed drops were incubated at room temperature (293 K) and the fluorescence intensity of the droplet mixture was surveyed at different times.

Example 1.5

Mammalian Cell Culture

MCF-7 breast carcinoma and 3T3 fibroblasts were acquired from American Tissue Culture Collection (ATCC). Cells were propagated in minimal essential medium (MEM) supplemented with 10% of Fetal Bovine Serum (FBS for MCF7) or 10% Calf Bovine Serum (CBS for 3T3) and passaged when cells reached ~80% confluence. For seeding on water-oil interfaces or nanoparticle-laded water-oil interfaces, the cells were detached using trypsin-EDTA for 5 minutes, neutralized with serum-containing medium, rinsed and resuspended in growth medium at 25,000 cell/mL. The suspension (200 µL, 5000 cells per well) was dispensed into a well of 96-well plate (hydrophobic polystyrene), which contained 100 µL of HFE or HFE-surfactant suspension. A two-layered system with significant curvature on the liquid-liquid interface was formed spontaneously. The suspension has to be dispensed rapidly along the wall of the well as one continuous stream to avoid formation of segregated aqueous droplets. The cells were allowed to sediment onto the water-oil interface for at least 1-2 hours prior to examining the cells by phase-contrast microscope (Leica) equipped with Phantom V7.3 camera (Vision Research). Experiments that used fluorescently labeled 3T3 cells were conducted similarly with one exception: the cells were incubated with 1 µg/mL solution of carboxyfluorescein succinimidyl ester (CFSE) in growth medium for 10 minutes, rinsed with CFSE-free medium and allowed to recover in growth medium for 15 minutes prior to detachment with trypsin and seeding. The CFSE-label was stable over 3-4 days; the intensity decreased as the amount of CFSE per cell was halved at each cell division. Cells were imaged using Zeiss LSM-700 laser-scanning confocal microscope equipped with 480 nm solid-state lasers, 10× or 20× objective, and the Zen software.

Example 2.1

Materials

All chemicals were used as purchased without purification Absolute ethanol (99%), tetraethyl orthosilicate (TEOS)

(98%), ammonium hydroxide solution (28%), poly-ethylene glycol (PEG, MW=8000), fluorescein, sodium salts of resazurin and resorufin were purchased from Sigma-Aldrich. 1H, 1H, 2H, 2H-perfluorooctyltriethoxysilane (FAS) (97%) was purchased from Fisher Scientific. Methoxyl PEG fluorescein (mPEG-Fluorescein, MW=5000) was purchased from Nanocs Inc. Methoxyl PEG silane (MW=1000) was purchased from Laysan Bio. Inc. Fluorescein diphosphate (FDP), bacterial alkaline phosphatase (BAP), and Amplex Red enzyme kit were purchased from Life Technologies.

Example 2.2

Synthesis of 100 nm F—SiO$_2$ NPs 100 nm F—SiO$_2$ NPs were synthesized according to the method disclosed in U.S. Prov. Appl. No. 62/068,510 filed Oct. 24, 2014. 3.57 mL of TEOS was added to a solution mixture containing 50 mL of ethanol (EtOH), 1 mL of deionized water, and 1.43 mL of NH$_4$OH (28 wt %). The solution was stirred vigorously at room temperature for 12 hours. 100 μL of FAS was then added directly to every 3 mL of the synthesized SiO$_2$ NPs solution obtained above, followed by vigorous stirring at room temperature for 60 min. EtOH was added to dilute the reacting solution to terminate the reaction, and the particles were washed by centrifugation at 10,000 rpm for 20 min. After three cycles of washing, the supernatant was removed and the resulting particles were desiccated overnight.

Example 2.3

Functionalization of F—SiO$_2$ NPs with PEGylated Silane

300 μL of FAS and either 80 μL or 750 μL of mPEG-silane in EtOH (10 mg/mL) were mixed and then added to 3 mL of synthesized SiO$_2$ NPs. The resulting mixture was stirred at room temperature for 30 min and the PEGylated NPs were isolated following the same procedure as that described for F—SiO$_2$ NPs.

Example 2.4

Droplet Generation

Monodisperse microdroplets were generated from flow-focusing devices. The continuous phase contains either 1.5% (w/w) 100-nm F—SiO$_2$ NPs dispersed in HFE-7500 or 2% (w/w) EA-surfactant in HFE-7500. For the dispersed phase, the composition is listed in Table 4. The flow rate of the continuous phase and the two streams of dispersed phase were fixed at 1.0 mL/hr, 0.1 mL/hr and 0.1 mL/hr respectively.

TABLE 4

| Assay | Aqueous stream 1 (lower stream in FIG. 19) | Aqueous stream 2 (upper stream in FIG. 19) | Final concentration in droplet |
|---|---|---|---|
| FDP/BAP (with PEG)[a] | 40 μL 1 mM FDP + 20 μL 1 mg/mL resorufin + 940 μL 50 mM Tris-HCl | 500 μL 37.5 U/mL BAP[c] + 400 μL 20 mg/mL PEG + 100 μL 50 mM Tris-HCl | [FDP] = 20 μM, [BAP] = 9.375 U/mL [PEG] = 4 mg/mL [resorufin] = 0.01 mg/mL[e] |
| FDP/BAP (without PEG)[a] | 40 μL 1 mM FDP + 20 μL 1 mg/mL resorufin + 940 μL 50 mM Tris-HCl | 500 μL 37.5 U/mL BAP + 500 μL 50 mM Tris-HCl | [FDP] = 20 μM, [BAP] = 9.375 U/mL [resorufin] = 0.01 mg/mL |
| Amplex red/HRP (with PEG)[b] | 10 μL 10 mM Amplex Red in DMSO + 200 μL 0.1 mM fluorescein + 790 μL 50 mM sodium phosphate buffer | 100 μL 100 mU/mL HRP[d] + 100 μL 20 mM H$_2$O$_2$ + 400 μL 20 mg/mL PEG + 400 μL 50 mM sodium phosphate buffer | [Amplex Red] = 50 μM, [HRP] = 5 mU/mL, [H$_2$O$_2$] = 1 mM, [PEG] = 4 mg/mL, [fluorescein] = 10 μM |
| Amplex red/HRP (without PEG)[b] | 10 μL 10 mM Amplex Red in DMSO + 200 μL 0.1 mM fluorescein + 790 μL 50 mM sodium phosphate buffer | 100 μL100 mU/mL HRP + 100 μL 20 mM H$_2$O$_2$ + 800 μL 50 mM sodium phosphate buffer | [Amplex Red] = 50 μM, [HRP] = 5 mU/mL, [H$_2$O$_2$] = 1 mM, [fluorescein] = 10 μM |

[a]Unless otherwise specified, all reagents were dissolved in 50 mM Tris-HCl
[b]Unless otherwise specified, all reagents were dissolved in 50 mM sodium phosphate buffer
[c]1 Unit is defined as the amount of BAP required to hydrolyze 1 nmol of ATP in 30 min at 37° C.
[d]1 Unit is defined as the amount of HRP required to form 1.0 mg purpurogallin from pyrogallol in 20 seconds at pH 6.0 and 20° C.
[e]Resorufin is an appropriate choice of internal standard, since resorufin leaks in drops stabilized by EA-surfactants when there is a concentration difference among the drops, here leakage is not observed since all drops contained equal concentrations of resorufin.

Example 2.5

Leakage Test for Amplex Red Assay with Different [HRP]

Positive and negative droplets were generated separately. Continuous phase contained 1.5% (w/w) 100 nm F—SiO2 NPs dispersed in HFE-7500. Positive droplets contained 75 μM Amplex Red reagent, 5 mU/mL HRP, 4 mg/mL PEG, 1 mM H$_2$O$_2$ and 10 μM fluorescein. Negative droplets contained 75 μM Amplex Red reagent, 0.1 mU/mL HRP, 4 mg/mL PEG, 1 mM H$_2$O$_2$ and 2 μM fluorescein. The droplets were collected in two Eppendorf tubes. Excess NPs in continuous phase was removed by washing with FC-40 three times. FC-40 was used instead of HFE-7500 to minimize partitioning of resorufin into the continuous phase, which was observed for fluorinated solvents that contained aliphatic ether groups. The positive droplets and negative droplets were then mixed at 1:1 ratio. The droplet mixture was incubated at room temperature (293 K) for 4 hours. In a separate control experiment, positive and negative droplets stabilized by EA-surfactant were mixed. The procedures were identical to that for NPs stabilized droplets except the continuous phase contained 2% EA-surfactant in HFE-7500, and no washing step was involved before the droplets were mixed.

Example 3.1

Use of Amphiphilic Silica Nanoparticles for Antibiotic Resistance Studies

Amphiphilic silica nanoparticles were applied to study single-cell level variability in antibiotic resistance when the microbial population is subject to temporal variations in drug dosage (e.g., uniform drug dosage v. increasing dosage over time) and different drug combinations. Because of leakage problem in surfactant droplets, the standard alamarBlue method could not be used for live or resistant E. coli detection in droplets. By using droplets stabilized by amphiphilic silica nanoparticles, the concentration of live E. coli can be detected in droplets, which enables the detection of antibiotic resistance. Previously, it was found that stronger resistance evolved with increasing dosage over time, but all time points were identified by peaks in bulk optical density measurements which can only detect cell concentrations>$10^6$ cfu/mL. As such, the details of exactly when the mutations started and how much of the subpopulation acquired such mutations were unknown. Using droplet microfluidics, better statistics were obtained on the composition of resistant subpopulations with enhanced time resolution. With established dielectrophoresis-based droplet sorting technology, the drops containing resistant cells can be sorted for subsequent sequencing to identify the genes responsible for the antibiotic resistance.

Additional Embodiments

Embodiment 1

A composition comprising at least one amphiphilic nanoparticle, wherein the nanoparticle is partially fluorinated, and wherein the nanoparticle has a contact angle θ of 90° to 135° when placed at an interface of a fluorous phase and an aqueous phase.

Embodiment 2

The composition of Embodiment 1, wherein the nanoparticle is a silica nanoparticle.

Embodiment 3

The composition of Embodiment 2, comprising a fluorous phase comprising at least one fluorinated solvent, wherein the silica nanoparticle is dispersed in the fluorinated solvent.

Embodiment 4

The composition of Embodiment 2, comprising a fluorous phase comprising at least one fluorinated solvent and an aqueous phase, wherein the silica nanoparticle is absorbed to the interface of the fluorous phase and the aqueous phase.

Embodiment 5

The composition of Embodiment 2, wherein the silica nanoparticle has at least one lateral dimension of 10-950 nm.

Embodiment 6

The composition of Embodiment 2, wherein the silica nanoparticle comprises fluorinated alkyl groups on the surface.

Embodiment 7

The composition of Embodiment 2, wherein the silica nanoparticle is partially derivatized with 1H, 1H, 2H, 2H-perfluorooctyltriethoxysilane (FAS) on the surface.

Embodiment 8

The composition of Embodiment 4, comprising an emulsion comprising (a) a continuous fluorous phase, and (b) at least one aqueous phase droplet dispersed in said continuous fluorous phase.

Embodiment 9

The composition of Embodiment 4, wherein the fluorous phase comprises at least one of HFE-7500, FC-40, and PFMD.

Embodiment 10

The composition of Embodiment 4, wherein the aqueous phase comprises at least one fluorescent molecule.

Embodiment 11

The composition of Embodiment 4, wherein the aqueous phase comprises at least one cell.

Embodiment 12

The composition of Embodiment 4, wherein the aqueous phase comprises at least one cell anchored to the silica nanoparticle at the interface of the fluorous phase and the aqueous phase.

Embodiment 13

A droplet microfluidic device comprising the composition of Embodiment 1.

Embodiment 14

A method for droplet-based assay, comprising dispersing at least one aqueous phase droplet in a continuous fluorous phase in a microfluidic channel, wherein at least one amphiphilic nanoparticle is absorbed to the interface of the continuous fluorous phase and the aqueous phase droplet, and wherein the nanoparticle is partially fluorinated.

Embodiment 15

The method of Embodiment 14, wherein the nanoparticle is a silica nanoparticle.

Embodiment 16

The method of Embodiment 15, wherein the silica nanoparticle has at least one lateral dimension of 10-950 nm.

Embodiment 17

The method of Embodiment 15, wherein the silica nanoparticle comprises fluorinated alkyl groups on the surface.

Embodiment 18

The method of Embodiment 15, wherein the silica nanoparticle is partially derivatized with 1H, 1H, 2H, 2H-perfluorooctyltriethoxysilane (FAS) on the surface.

Embodiment 19

The method of Embodiment 15, wherein the fluorous phase comprises at least one fluorinated solvent.

Embodiment 20

The method of Embodiment 15, wherein the fluorous phase comprises at least one of HFE-7500, FC-40, and PFMD.

Embodiment 21

The method of Embodiment 15, wherein the aqueous phase comprises at least one fluorescent molecule.

Embodiment 22

The method of Embodiment 15, wherein the aqueous phase comprises at least one cell.

Embodiment 23

A method for making the composition of Embodiment 2, comprising reacting silica nanoparticles with at least one fluorinating agent to obtain a composition comprising amphiphilic silica nanoparticles, wherein at least 50% of the silica nanoparticles in the composition obtained have a contact angle θ of about 90° to 135° when placed at an interface of a fluorous oil phase and a water phase.

Embodiment 24

A method for droplet-based assay, comprising dispersing at least one aqueous phase droplet in a continuous fluorous phase in a microfluidic channel, wherein the continuous fluorous phase comprises at least one partially fluorinated amphiphilic particle adsorbed to an interface of the continuous fluorous phase and the aqueous phase droplet, and wherein: (a) the aqueous phase droplet comprises at least one hydrophilic polymer adsorbed to the amphiphilic particle at the interface or (b) the amphiphilic particle is covalently grafted with at least one hydrophilic polymer.

Embodiment 25

The method of Embodiment 24, wherein the aqueous phase droplet comprises at least one hydrophilic polymer adsorbed to the amphiphilic particle at the interface.

Embodiment 26

The method of Embodiment 24, wherein the hydrophilic polymer comprises at least one of polyethylene glycol (PEG), polyethers, polyacrylamide (PAM), polyethylenimine (PEI), poly(acrylic acid), polymethacrylate, poly(vinyl alcohol) (PVA), and poly(vinylpyrrolidone) (PVP).

Embodiment 27

The method of Embodiment 24, wherein the amphiphilic particle is a nanoparticle or a microparticle.

Embodiment 28

The method of Embodiment 24, wherein the amphiphilic particle is a silica particle.

Embodiment 29

The method of Embodiment 24, wherein the amphiphilic particle is functionalized with fluorinated alkyl groups on the surface.

Embodiment 30

The method of Embodiment 24, wherein the fluorous phase further comprises at least one fluorinated solvent.

Embodiment 31

The method of Embodiment 24, wherein the fluorous phase comprises at least one of HFE-7500, HFE-7600, FC-40, and PFMD.

Embodiment 32

The method of Embodiment 24, wherein the aqueous phase further comprises at least one protein selected from the group consisting of enzymes, antibodies, hormones, structural proteins, and membrane proteins.

Embodiment 33

The method of Embodiment 24, wherein the aqueous phase further comprises at least one fluorescent molecule.

Embodiment 34

The method of Embodiment 24, wherein the amphiphilic particle is a silica nanoparticle, wherein the hydrophilic polymer comprises polyethylene glycol (PEG), and wherein the aqueous phase comprises at least one enzyme.

Embodiment 35

A Pickering emulsion comprising a continuous fluorous phase and at least one aqueous phase droplet dispersed therein, wherein the continuous fluorous phase comprises at least one partially fluorinated amphiphilic particle adsorbed to an interface of the continuous fluorous phase and the aqueous phase droplet, and wherein: (a) the aqueous phase droplet comprises at least one hydrophilic polymer adsorbed to the amphiphilic particle at the interface or (b) the amphiphilic particle is covalently grafted with at least one hydrophilic polymer

Embodiment 36

The Pickering emulsion of Embodiment 35, wherein the aqueous phase droplet comprises at least one hydrophilic polymer adsorbed to the amphiphilic particle at the interface.

Embodiment 37

The Pickering emulsion of Embodiment 35, wherein the hydrophilic polymer comprises at least one of polyethylene glycol (PEG), polyethers, polyacrylamide (PAM), polyethylenimine (PEI), poly(acrylic acid), polymethacrylate, poly(vinyl alcohol) (PVA), and poly(vinylpyrrolidone) (PVP).

Embodiment 38

The Pickering emulsion of Embodiment 35, wherein the amphiphilic particle is a nanoparticle or a microparticle.

Embodiment 39

The Pickering emulsion of Embodiment 35, wherein the amphiphilic particle is a silica particle.

Embodiment 40

The Pickering emulsion of Embodiment 35, wherein the amphiphilic particle is functionalized with fluorinated alkyl groups on the surface.

Embodiment 41

The Pickering emulsion of Embodiment 35, wherein the fluorous phase further comprises at least one fluorinated solvent.

Embodiment 42

The Pickering emulsion of Embodiment 35, wherein the fluorous phase comprises at least one of HFE-7500, HFE-7600, FC-40, and PFMD.

Embodiment 43

The Pickering emulsion of Embodiment 35, wherein the aqueous phase further comprises at least one protein selected from the group consisting of enzymes, antibodies, hormones, structural proteins, and membrane proteins.

Embodiment 44

The Pickering emulsion of Embodiment 35, wherein the aqueous phase further comprises at least one fluorescent molecule.

Embodiment 45

The Pickering emulsion of Embodiment 35, wherein the amphiphilic particle is a silica nanoparticle, wherein the hydrophilic polymer comprises polyethylene glycol (PEG), and wherein the aqueous phase comprises at least one enzyme.

Embodiment 46

A droplet microfluidic device comprising a microfluidic channel, wherein microfluidic channel comprises a continuous fluorous phase and at least one aqueous phase droplet dispersed therein, wherein the continuous fluorous phase comprises at least one partially fluorinated amphiphilic nanoparticle adsorbed to an interface of the continuous fluorous phase and the aqueous phase droplet, and wherein: (a) the aqueous phase droplet comprises at least one hydrophilic polymer adsorbed to the amphiphilic nanoparticle at the interface or (b) the amphiphilic particle is covalently grafted with at least one hydrophilic polymer.

Embodiment 47

The method of Embodiment 14, wherein the aqueous phase droplet comprises prokaryotic cells (e.g., bacteria) and/or eukaryotic cells (e.g., yeast, mammalian cells), and wherein the method comprises growing/fermenting the cells in the aqueous phase.

Embodiment 48

The method of Embodiment 47, wherein the cells produce at least one biofuel.

Embodiment 49

The method of Embodiment 24, wherein the aqueous phase droplet comprises prokaryotic cells (e.g., bacteria) and/or eukaryotic cells (e.g., yeast, mammalian cells), and wherein the method comprises growing/fermenting the cells in the aqueous phase.

Embodiment 50

The method of Embodiment 49, wherein the cells produce at least one biofuel.

Embodiment 51

The method of Embodiment 14, wherein the aqueous phase droplet comprises at least one cell and at least one antibiotic, and wherein the method comprises detecting the cell's antibiotic resistance.

Embodiment 52

The method of Embodiment 51, wherein the aqueous phase droplet further comprises at least one fluorophore or fluorogenic substrate, and wherein the method comprises detecting intensity of a fluorescence signal.

Embodiment 53

The method of Embodiment 51, wherein the method further comprises sorting an aqueous phase droplet comprising an antibiotic-resistant cell, and sequencing and/or genotyping the antibiotic-resistant cell.

Embodiment 54

The method of Embodiment 24, wherein the aqueous phase droplet comprises at least one cell and at least one antibiotic, and wherein the method comprises detecting the cell's antibiotic resistance.

Embodiment 55

The method of Embodiment 54, wherein the aqueous phase droplet further comprises at least one fluorophore or fluorogenic substrate, and wherein the method comprises detecting intensity of a fluorescence signal.

Embodiment 56

The method of Embodiment 54, wherein the method further comprises sorting an aqueous phase droplet comprising an antibiotic-resistant cell, and sequencing and/or genotyping the antibiotic-resistant cell.

Embodiment 57

The method of Embodiment 14, wherein the aqueous phase droplet comprises at least one cell and at least one drug, and wherein the method comprises detecting the cell's response to the drug.

Embodiment 58

The method of Embodiment 57, wherein the method further comprises determining toxicity, drug efficacy, drug resistance, and/or dose response.

Embodiment 59

The method of Embodiment 24, wherein the aqueous phase droplet comprises at least one cell and at least one drug, and wherein the method comprises detecting the cell's response to the drug.

Embodiment 60

The method of Embodiment 59, wherein the method further comprises determining toxicity, drug efficacy, drug resistance, and/or dose response.

As used herein, the singular terms "a," "an," and "the" include plural referents unless the context clearly dictates otherwise. Thus, for example, reference to a molecule can include multiple molecules unless the context clearly dictates otherwise.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scopes of this invention.

What is claimed is:

1. A composition comprising (a) a fluorous phase comprising at least one fluorinated solvent, (b) an aqueous phase, and (c) amphiphilic silica nanoparticles that are partially fluorinated such that the silica nanoparticles comprise fluorinated or partially fluorinated alkyl groups covalently bonded on the surface of the silica nanoparticles, wherein at least 50% of all silica nanoparticles in the composition have a contact angle $\theta$ of 90° to 135° at an interface of the fluorous phase and the aqueous phase and is absorbed to the interface of the fluorous phase and the aqueous phase, and wherein the contact angle is measured from the aqueous phase, and wherein the fluorous phase comprises at least one of 2-(trifluoromethyl)-3-ethoxydodecafluorohexane, 1,1,2,2,3,3,4,4,4-Nonafluoro-N,N-bis(1,1,2,2,3,3,4,4,4-nonafluorobutyl)butan-1-amine, 1,1,2,2,3,3,4,4,4-nonafluoro-N-(1,1,2,2,3,3,4,4,4-nonafluorobutyl)-N-(trifluoromethyl)butan-1-amine, perfluorohexane, or perfluoromethyldecalin.

2. The composition of claim 1, wherein the silica nanoparticle is partially derivatized with 1H, 1H, 2H, 2H-perfluorooctyltriethoxysilane covalently bonded on the surface.

3. The composition of claim 1, wherein the aqueous phase comprises at least one fluorescent molecule.

4. The composition of claim 1, wherein the aqueous phase comprises at least one cell.

5. The composition of claim 1, wherein the aqueous phase comprises at least one cell anchored to the silica nanoparticle at the interface of the fluorous phase and the aqueous phase.

6. The composition of claim 1, wherein the contact angle $\theta$ is 90° to 120°.

7. The composition of claim 1, wherein the contact angle $\theta$ is 100° to 110°.

8. The composition of claim 1, wherein the fluorinated or partially fluorinated alkyl groups comprise a partially fluorinated or perfluorinated alkyl-silane covalently bonded on the surface of the silica nanoparticle.

9. The composition of claim 1, wherein the fluorinated or partially fluorinated alkyl groups comprise 10 to 20 carbon atoms per alkyl group.

10. The composition of claim 1, wherein the fluorinated or partially fluorinated alkyl groups are substituted with 10 or more fluorine atoms per alkyl group.

11. The composition of claim 1, wherein at least 70% of all silica nanoparticles in the composition have a contact angle $\theta$ of 90° to 135°.

12. The composition of claim 1, wherein at least 90% of all silica nanoparticles in the composition have a contact angle $\theta$ of 90° to 135°.

13. The composition of claim 1, wherein the amphiphilic silica nanoparticles have at least one dimension in a range from 10 to 950 nm.

14. An emulsion composition comprising (a) a continuous fluorous phase, (b) at least one aqueous phase droplet dispersed in said continuous fluorous phase, and (c) amphiphilic silica nanoparticles that are partially fluorinated such that the silica nanoparticles comprise fluorinated or partially fluorinated alkyl groups covalently bonded on the surface of the silica nanoparticles, wherein at least 50% of all silica nanoparticles in the emulsion composition have a contact angle θ of 90° to 135° at an interface of the continuous fluorous phase and the aqueous phase droplet and is absorbed to the interface of the continuous fluorous phase and the aqueous phase droplet, and wherein the contact angle is measured from the aqueous phase droplet, and wherein the continuous fluorous phase comprises at least one of 2-(trifluoromethyl)-3-ethoxydodecafluorohexane, 1,1,2,2,3,3,4,4,4-nonafluoro-N,N-bis(1,1,2,2,3,3,4,4,4-nonafluorobutyl)butan-1-amine, 1,1,2,2,3,3,4,4,4-nonafluoro-N-(1,1,2,2,3,3,4,4,4-nonafluorobutyl)-N-(trifluoromethyl)butan-1-amine, perfluorohexane, or perfluoromethyldecalin.

\* \* \* \* \*